United States Patent
Dietrich et al.

(10) Patent No.: US 6,309,858 B1
(45) Date of Patent: Oct. 30, 2001

(54) T-TYPE CALCIUM CHANNEL VARIANTS; COMPOSITIONS THEREOF; AND USES

(75) Inventors: Paul Shartzer Dietrich, Palo Alto; Joseph Gerard McGivern, Mountain View, both of CA (US)

(73) Assignee: Syntex (U.S.A.) LLC, Palo Alto, CA (US)

(*) Notice: Subject to any disclaimer, the term of this patent is extended or adjusted under 35 U.S.C. 154(b) by 0 days.

(21) Appl. No.: 09/404,650

(22) Filed: Sep. 23, 1999

Related U.S. Application Data

(60) Provisional application No. 60/102,222, filed on Sep. 29, 1998.

(51) Int. Cl.[7] .............................. C12P 21/02; C12N 5/00; C12N 15/00; C07H 21/02; C07H 21/04
(52) U.S. Cl. ..................... 435/69.1; 435/320.1; 435/325; 435/335; 435/455; 536/23.1; 536/23.5
(58) Field of Search .................................. 530/23.1, 23.5; 435/320.1, 325, 69.1, 335

(56) References Cited

U.S. PATENT DOCUMENTS 5,475,021  12/1995  Marnett et al. ....................... 514/425

FOREIGN PATENT DOCUMENTS

| WO 98/07447 | 2/1998 | (WO) . |
| WO 98/38301 | 3/1998 | (WO) . |
| WO 99/29847 | 6/1999 | (WO) . |

OTHER PUBLICATIONS

Arner, S. And Myerson, B., "Opioids in Neuropathic Pain," *Pain Digest* 3:15–22 (1993).
Browne et al., "Ethosuximide in the Treatment of Absence (Petit Mal) Seizures," *Neurology* 25:515–524 (1975).
Campbell et al., "Clinical Trial of Carbazepine (Tegretol) in Trigeminal Neuralgia," *J. Neurol. Neurosurg. Psychiatry* 29:265–267 (1966).
Coulter et al., "Characterization of Ethousuxmide Reduction of Low–Threshold Calcium Current in Thalamic Neurons," *Annals of Neurology* 25(6):582–593 (1989).
Coulter et al., "Specific Petit Mal Anticonvulsants Reduce Calcium Currents in Thalamic Neurons," *Neuroscience Letters* 98:74–78 (1989).
Cribbs et al., "Cloning and Characterization of 1H From Human Heart, a Member of the T–Type $Ca^{2+}$ Channel Gene Family," *Circ. Res.* 83:103–109 (1998).
Ertel, S.I. and Ertel, E.A., "Low–Voltage–Active T–Type $Ca^{2+}$ Channels," *Trends Pharmacol Sci.* 18:37–42 (1997).
Hunter et al., "The Effect of Novel Anti–Epileptic Drugs in Rat Experimental Models of Acute and Chronic Pain," *European Journal of Pharmacology* 324:153–160 (1997).
Killian, J.M. and Fromm, G.H., "Carbamazepine in the Treatment of Neuralgia–Use and Side Effects," *Arch. Neurol.* 19:129–136 (1968).

Lenz, Fredrick A., Central Pain: Current Treatments, Future Prospects, *Neuropathic Pain: Progress and Prospects*, Jun. 4–6 p. 17 (1998).
Max et al. "Association of Pain Relief with Drug Side Effects in Postherpetic Neuralgia: A Single–Dose Study of Clonidine, Codeine, Ibuprofen, and Placebo," *Clin. Pharmacol. Ther.* 43:363–371 (1988).
McQuay et al., "Anticonvulsant Drugs for Management of Pain: A Systematic Review," *Br. Med. J.* 311:1047–1052 (1995).
Perez–Reyes, E., and Schneider, T., "Molecular Biology of Calcium Channels," *Kidney International* 48:1111–1124 (1995).
Perez–Reyes et al., "Molecular Characterization of a Neuronal Low–Voltage–Activated T–Type Calcium Channel," *Nature* 391:896–900 (1998).
Scroggs, R.S., and Fox, A.P., "Calcium Current Variation Between Acutely Isolated Adult Rat Dorsal Root Ganglion Neurons of Different Size," *J. Of Physiology* 445:639–658 (1992).
Suzuki, S., and Rogawski, M.A., "T–Type Calcium Channels Mediate the Transition Between Tonic and Phasic Firing in Thalamic Neurons," *Proc. Natl. Acad. Sci. USA* 86:7228–7232 (1989).
Swerdlow, M., "Anticonvulsant Drugs and Chronic Pain," *Clinical Neuropharmacology* 7(1):51–82 (1984).
Todorovic, S.L., and Lingle, C.J., "Pharmacological Properties of T–Type $CA^{2+}$ Current in Adult Rat Sensory Neurons: Effects of Anticonvulsant and Anesthetic Agents," *J. Neurophysiol* 79(1):240–252 (1998).
Upton, N., "Mechanisms of Action of New Antiepileptic Drugs: Rational Design and Serendipitous Finding," *Trends Pharmacol Sci.* 15:456–463 (1994).
White et al., "Transient Low–Threshold $Ca^{2+}$ Current Triggers Burst Firing Through an Afterdepolarizing Potential in an Adult Mammalian Neuron," *Proc. Natl. Acad. Sci. USA* 86:6802–6806 (1989).
Lee et al., Gen. Bank Accession No. AF086827, Bethesda, MD. Mar. 4, 1999.
Dzhura et al., "Characterization of Hypothalamic Low–Voltage–Activated Ca Channels Based On Their Functional Expression in Xenopus Oocytes," *Neuroscience* vol. 70, No. 3: 729–738 (1996).
Mittman et al., "Structure and Alternative Splicing of the Gene Encoding $α_{1I}$, A Human Brain T Calcium Channel $α_{1I}$ Subunit," *Neuroscience Letters* 269:121–124 (1999).
Jung–Ha Lee, et al. (1999) "Cloning and Expression of a Novel Member of the Low Voltage–Activated T–Type Calcium Channel Family," *J. Neurosci.* 19:1912–1921.

*Primary Examiner*—Scott D. Priebe
(74) *Attorney, Agent, or Firm*—Sheela Mohan-Peterson; Rohan Peries

(57) ABSTRACT

The invention provides TCCV-1 or TCCV-2 from human, reagents related thereto including polynucleotides encoding TCCV-1 or TCCV-2, purified polypeptides, and specific antibodies. Methods of making and using these reagents, in particular, methods for screening compounds which modulate TCCV-1 or TCCV-2 activity are provided. Also provided are methods of diagnosis and kits.

12 Claims, 10 Drawing Sheets

Figure 1A

```
SEQ ID NO:2    MAESASPPSSSAAAPAAEPGVTTEQPGPRSPPSSPPGLEEPLDGADPHVPHPDLAPIAFF    60
SEQ ID NO:4    MAESASPPSSSAAAPAAEPGVTTEQPGPRSPPSSPPGLEEPLDGADPHVPHPDLAPIAFF    60
SEQ ID NO:5    MADSNLPPSS.AAAPAPEPGI.TEQPGPRSPPSPPGLEEPLEGTNPDVPHPDLAPVAFF    58

SEQ ID NO:2    CLRQTTSPRNWCIKMVCNPWFECVSMLVILLNCVTLGMYQPCDDMDCLSDRCKILQVFDD   120
SEQ ID NO:4    CLRQTTSPRNWCIKMVCNPWFECVSMLVILLNCVTLGMYQPCDDMDCLSDRCKILQVFDD   120
SEQ ID NO:5    CLRQTTSPRNWCIKMVCNPWFECVSMLVILLNCVTLGMYQPCDDMECLSDRCKILQVFDD   118

SEQ ID NO:2    FIFIFFAMEMVLKMVALGIFGKKCYLGDTWNRLDFFIVMAGMVEYSLDLQNINLSAIRTV   180
SEQ ID NO:4    FIFIFFAMEMVLKMVALGIFGKKCYLGDTWNRLDFFIVMAGMVEYSLDLQNINLSAIRTV   180
SEQ ID NO:5    FIFIFFAMEMVLKMVALGIFGKKCYLGDTWNRLDFFIVMAGMVEYSLDLQNINLSAIRTV   178

SEQ ID NO:2    RVLRPLKAINRVPSMRILVNLLLDTLPMLGNVLLLCFFVFFIFGIIGVQLWAGLLRNRCF   240
SEQ ID NO:4    RVLRPLKAINRVPSMRILVNLLLDTLPMLGNVLLLCFFVFFIFGIIGVQLWAGLLRNRCF   240
SEQ ID NO:5    RVLRPLKAINRVPSMRILVNLLLDTLPMLGNVLLLCFFVFFIFGIIGVQLWAGLLRNRCF   238

SEQ ID NO:2    LEENFTIQGDVALPPYYQPEEDDEMPFICSLSGDNGIMGCHEIPPLKEQGRECCLSKDDV   300
SEQ ID NO:4    LEENFTIQGDVALPPYYQPEEDDEMPFICSLSGDNGIMGCHEIPPLKEQGRECCLSKDDV   300
SEQ ID NO:5    LEENFTIQGDVALPPYYQPEEDDEMPFICSLTGDNGIMGCHEIPPLKEQGRECCLSKDDV   298

SEQ ID NO:2    YDFGAGRQDLNASGLCVNMNRYYNVCRTGSANPHKGAINFDNIGYAWIVIFQVITLEGWV   360
SEQ ID NO:4    YDFGAGRQDLNASGLCVNMNRYYNVCRTGSANPHKGAINFDNIGYAWIVIFQVITLEGWV   360
SEQ ID NO:5    YDFGAGRQDLNASGLCVNMNRYYNVCRTGNANPHKGAINFDNIGYAGIVIFQVITLEGWV   358
```

Figure 1B

```
SEQ ID NO:2    EIMYYVMDAHSFYNFIYFILLIIVGSFFMINLCLVVIATQFSETKQREHRLMLEQRQRYL    420
SEQ ID NO:4    EIMYYVMDAHSFYNFIYFILLIIVGSFFMINLCLVVIATQFSETKQREHRLMLEQRQRYL    420
SEQ ID NO:5    EIMYYVMDAHSFYNFIYFILLIIVGSFFMINLCLVVIATQFSETKQREHRLMLEQRQRYL    418

SEQ ID NO:2    SSSTVASYAEPGDCYEEIFQYVCHILRKAKRRALGLYQALQSRRQALGPEAPAPAKPGPH    480
SEQ ID NO:4    SSSTVASYAEPGDCYEEIFQYVCHILRKAKRRALGLYQALQSRRQALGPEAPAPAKPGPH    480
SEQ ID NO:5    SSSTVASYAEPGDCYEEIFQYVCHILRKAKRRALGLYQALQNRRQAMGPGTPAPAKPGPH    478

SEQ ID NO:2    AKEPRHYQLCPQHSPLDATPHTLVQPIPATLASDPASCPCCQHEDGRRPSGLGSTDSGQE    540
SEQ ID NO:4    AKEPRHYQLCPQHSPLDATPHTLVQPIPATLASDPASCPCCQHEDGRRPSGLGSTDSGQE    540
SEQ ID NO:5    AKEPSHCKLCPRHSPLDPTPHTLVQPISAILASDPSSCPHCQHEAGRRPSGLGSTDSGQE    538

SEQ ID NO:2    GSGSGSSAGGEDEADGDGARSSEDGASSELGKEEEEEQADGAVWLCGDVWRETRAKLRG    600
SEQ ID NO:4    GSGSGSSAGGEDEADGDGARSSEDGASSELGKEEEEEQADGAVWLCGDVWRETRAKLRG    600
SEQ ID NO:5    GSGSGSGSA..EAEANGDGLQSSEDGVSSDLGKEE...EQEDGAARLCGDVWRETRKKLRG    593

SEQ ID NO:2    IVDSKYFNRGIMMAILVNTVSMGIEHHEQPEELTNILEICNVVFTSMFALEMILKLAAFG    660
SEQ ID NO:4    IVDSKYFNRGIMMAILVNTVSMGIEHHEQPEELTNILEICNVVFTSMFALEMILKLAAFG    660
SEQ ID NO:5    IVDSKYFNRGIMMAILVNTVSMGIEHHEQPEELTNILEICNVVFTSMFALEMILKLAAFG    653

SEQ ID NO:2    LFDYLRNPYNIFDSIIVIISIWEIVGQADGGLSVLRTFRLLKLVRFMPALRRQLVVL    720
SEQ ID NO:4    LFDYLRNPYNIFDSIIVIISIWEIVGQADGGLSVLRTFRLLRVLKLVRFMPALRRQLVVL    720
SEQ ID NO:5    LFDYLRNPYNIFDSIIVIISIWEIVGQADGGLSVLRTFRLLRVLKLVRFMPALRRQLVVL    713
```

Figure 1C

```
SEQ ID NO:2    MKTMDNVATFCMLLMLFIFIFSILGMHIFGCKFSLRTDTGDTVPDRKNFDSLLMAIVTVF    780
SEQ ID NO:4    MKTMDNVATFCMLLMLFIFIFSILGMHIFGCKFSLRTDTGDTVPDRKNFDSLLMAIVTVF    780
SEQ ID NO:5    MKTMDNVATFCMLLMLFIFIFSILGMHIFGCKFSLRTDTGDTVPDRKNFDSLLMAIVTVF    773

SEQ ID NO:2    QILTQEDWNVVLYNGMASTSPWASLYFVALMTFGNYVLFNLLVAILVEGFQAEGDANRSY    840
SEQ ID NO:4    QILTQEDWNVVLYNGMASTSPWASLYFVALMTFGNYVLFNLLVAILVEGFQAEGDANRSY    840
SEQ ID NO:5    QILTQEDWNVVLYNGMASTTPWASLYFVALMTFGNYVLFNLLVAILVEGFQAEGDANRSC    833

SEQ ID NO:2    SDEDQSSSNIEEFDKLQEGLDSSGDPKLCPIPMTPNGHLDPSLPLGGHLGPAGAAGPAPR    900
SEQ ID NO:4    SDEDQSSSNIEEFDKLQEGLDSSGDPKLCPIPMTPNGHLDPSLPLGGHLGPAGAAGPAPR    900
SEQ ID NO:5    SDEDQSSSNLEEFDKLPEGLDNSRDLKLCPIPMTPNGHLDPSLPLGAHLGPAGTMGTAPR    893

SEQ ID NO:2    LSLQPDPMLVALGSRKSSVMSLGRMSYDQRSLSSSRSSYYGPWGRSAAWASRRSSWNSLK    960
SEQ ID NO:4    LSLQPDPMLVALGSRKSSVMSLGRMSYDQRSLSSSRSSYYGPWGRSAAWASRRSSWNSLK    960
SEQ ID NO:5    LSLQPDPVLVALDSRKSSVMSLGRMSYDQRSLSSSRSSYYGPWGRSGTWASRRSSWNSLK    953

SEQ ID NO:2    HKPPSAEHESLLSAERGGG.ARVCEVAADEGPPRAAPLHTPHAHHIHHGPHLAHRHRHHR    1019
SEQ ID NO:4    HKPPSAEHESLLSAERGGG.ARVCEVAADEGPPRAAPLHTPHAHHIHHGPHLAHRHRHHR    1019
SEQ ID NO:5    HKPPSAEHESLLSGEGGGSCVRACEGAREEAPTRTAPLHAPHAHHAHHGPHLAHRHRHHR    1013

SEQ ID NO:2    RTLSLDNRDSVDLAELVPAVGAHPRAAWRAAGPAPGHEDCNGRMPSIAKDVFTKMGDRGD    1079
SEQ ID NO:4    RTLSLDNRDSVDLAELVPAVGAHPRAAWRAAGPAPGHEDCNGRMPSIAKDVFTKMGDRGD    1079
SEQ ID NO:5    RTLSLDTRDSVDLGELVPVVGAHSRAAWRGAGQAPGHEDCNGRMPNIAKDVFTKMDDRRD    1073
```

Figure 1D

```
SEQ ID NO:2   RGEDEEEIDYTLCFRVRKMIDVYKPDWCEVREDWSVYLFSPENRFRVLCQTIIAHKLFDY   1139
SEQ ID NO:4   RGEDEEEIDYTLCFRVRKMIDVYKPDWCEVREDWSVYLFSPENRFRVLCQTIIAHKLFDY   1139
SEQ ID NO:5   RGEDEEEIDYTLCFRVRKMIDVYKPDWCEVREDWSVYLFSPENKFRILCQTIIAHKLFDY   1133

SEQ ID NO:2   VVLAFIFLNCITIALERPQIEAGSTERIFLTVSNYIFTAIFVGEMTLKVVSLGLYFGEQA   1199
SEQ ID NO:4   VVLAFIFLNCITIALERPQIEAGSTERIFLTVSNYIFTAIFVGEMTLKVVSLGLYFGEQA   1199
SEQ ID NO:5   VVLAFIFLNCITIALERPQIEAGSTERIFLTVSNYIFTAIFVGEMTLKVVSLGLYFGEQA   1199

SEQ ID NO:2   YLRSSWNVLDGFLVFVSIIDIVVSLASAGGAKILGVLRVLRLLRTLRPLRVISRAPGLKL   1259
SEQ ID NO:4   YLRSSWNVLDGFLVFVSIIDIVVSLASAGGAKILGVLRVLRLLRTLRPLRVISRAPGLKL   1259
SEQ ID NO:5   YLRSSWNVLDGFLVFVSIIDIVVSVASAGGAKILGVLRVLRLLRTLRPLRVISRAPGLKL   1253

SEQ ID NO:2   VVETLISSLKPIGNIVLICCAFFIIFGILGVQLFKGKFYHCLGVDTRNITNRSDCMAANY   1319
SEQ ID NO:4   VVETLISSLKPIGNIVLICCAFFIIFGILGVQLFKGKFYHCLGVDTRNITNRSDCMAANY   1319
SEQ ID NO:5   VVETLISSLKPIGNIVLICCAFFIIFGILGVQLFKGKFYHCLGVDTRNITNRSDCVAANY   1313

SEQ ID NO:2   RWVHHKYNFDNLGQALMSLFVLASKDGWVNIMYNGLDAVAVDQQPVTNHNPWMLLYFISF   1379
SEQ ID NO:4   RWVHHKYNFDNLGQALMSLFVLASKDGWVNIMYNGLDAVAVDQQPVTNHNPWMLLYFISF   1379
SEQ ID NO:5   RWVHHKYNFDNLGQALMSLFVLASKDGWVNIMYNGLDAVAVDQQPVTNHNPWMLLYFISF   1373

SEQ ID NO:2   LLIVSFFVLNMFVGVVVENFHKCRQHQEAEEARRREEKRLRLEKKRRKAQRLPYYATYC   1439
SEQ ID NO:4   LLIVSFFVLNMFVGVVVENFHKCRQHQEAEEARRREEKRLRLEKKRRKAQRLPYYATYC   1439
SEQ ID NO:5   LLIVSFFVLNMFVGVVVENFHKCRQHQEAEEARRREEKRLRLEKKRRKAQRLPYYATYC   1433
```

Figure 1E

```
SEQ ID NO:2  HTRLLIHSMCTSHYLDIFITFIICLNVTMSLEHYNQPTSLETALKYCNYMFTTVFVLEA  1499
SEQ ID NO:4  HTRLLIHSMCTSHYLDIFITFIICLNVTMSLEHYNQPTSLETALKYCNYMFTTVFVLEA  1499
SEQ ID NO:5  PTRLLIHSMCTSHYLDIFITFIICLNVTMSLEHYNQPTSLETALKYCNYMFTTVFVLEA  1493

SEQ ID NO:2  VLKLVAFGLRRFFKDRWNQLDLAIVLLSVMGITLEEIEINAALPINPTIIRIMRVLRIAR  1559
SEQ ID NO:4  VLKLVAFGLRRFFKDRWNQLDLAIVLLSVMGITLEEIEINAALPINPTIIRIMRVLRIAR  1559
SEQ ID NO:5  VLKLVAFGLRRFFKDRWNQLDLAIVLLSVMGITLEEIEINAALPINPTIIRIMRVLRIAR  1553

SEQ ID NO:2  VLKLLKMATGMRALLDTVVQALPQVGNLGLLFMLLFFIYAALGVELFGKLVCNDENPCEG  1619
SEQ ID NO:4  VLKLLKMATGMRALLDTVVQALPQVGNLGLLFMLLFFIYAALGVELFGKLVCNDENPCEG  1619
SEQ ID NO:5  VLKLLKMATGMRALLDTVVQALPQVGNLGLLFMLLFFIYAALGVELFGKLVCNDENPCEG  1613

SEQ ID NO:2  MSRHATFENFGMAFLTLFQVSTGDNWNGIMKDTLRDCTHDERSCLSSLQFVSPLYFVSFV  1679
SEQ ID NO:4  MSRHATFENFGMAFLTLFQVSTGDNWNGIMKDTLRDCTHDERSCLSSLQFVSPLYFVSFV  1679
SEQ ID NO:5  MSRHATFENFGMAFLTLFQVSTGDNWNGIMKDTLRDCTHDERTCLSSLQFVSPLYFVSFV  1673

SEQ ID NO:2  LTAQFVLINVVVAVLMKHLDDSNKEAQEDAEMDAELELEMAHGLGP...............  1725
SEQ ID NO:4  LTAQFVLINVVVAVLMKHLDDSNKEAQEDAEMDAELELEMAHGLGP...............  1725
SEQ ID NO:5  LTAQFVLINVVVAVLMKHLDDSNKEAQEDAEMDAEIELEMAHGLGPCPGPCPGPCPCPCP  1733

SEQ ID NO:2  ....GPRLPTGSPGAPGRPGPGAGGGGDTEGGLCRRCYSPAQ........DSLEG  1768
SEQ ID NO:4  ....GPRLPTGSPGAPGRPGPGAGGGGDTEGGLCRRCYSPAQENLWLDSVSLIIKDSLEG  1781
SEQ ID NO:5  CPCAGPRLPTSSPGAPGRGSGGAGAGGDTESHLCRHCYSPAQETLWLDSVSLIIKDSLEG  1793
```

Figure 1F

```
SEQ ID NO:2   ELTIIDNLSGSIFHHYSSPAGCKKCHHDKQEVQLAEFTEAFSLNSDRSSSILLGDDLSLED  1828
SEQ ID NO:4   ELTIIDNLSGSIFHHYSSPAGCKKCHHDKQEVQLAEFTEAFSLNSDRSSSILLGDDLSLED  1841
SEQ ID NO:5   ELTIIDNLSGSVFHHYASPDGCGKCHHDKQETGLHPSCWGMT                    1835

SEQ ID NO:2   PTACPPGRKDSKGELDPPEPMRVGDLGECFFPLSSTAVSPDPENFLCEMEEIPFNPVRSW  1888
SEQ ID NO:4   PTACPPGRKDSKGELDPPEPMRVGDLGECFFPLSSTAVSPDPENFLCEMEEIPFNPVRSW  1901

SEQ ID NO:2   LKHDSSQAPPSPFSPDASSPLLPMPAEFFHPAVSASQKGPEKGTGTGTLPKIALQGSWAS  1948
SEQ ID NO:4   LKHDSSQAPPSPFSPDASSPLLPMPAEFFHPAVSASQKGPEKGTGTGTLPKIALQGSWAS  1961

SEQ ID NO:2   LRSPRVNCTLLRQATGSDTSLDASPSSSAGSLQTTLEDSLTLSDSPRRALGPPAPAPGPR  2008
SEQ ID NO:4   LRSPRVNCTLLRQATGSDTSLDASPSSSAGSLQTTLEDSLTLSDSPRRALGPPAPAPGPR  2021

SEQ ID NO:2   AGLSPAARRRLSLRGRGLFSLRGLRAHQRSHSSGGSTSPGCTHHDSMDPSDEEGRGGAGG  2068
SEQ ID NO:4   AGLSPAARRRLSLRGRGLFSLRGLRAHQRSHSSGGSTSPGCTHHDSMDPSDEEGRGGAGG  2081

SEQ ID NO:2   GGAGSEHSETLSSLSLSLTSLFCPPPPPAPGLTPARKFSSTSSLAAPGRPHAAALAHGLAR  2128
SEQ ID NO:4   GGAGSEHSETLSSLSLSLTSLFCPPPPPAPGLTPARKFSSTSSLAAPGRPHAAALAHGLAR  2141

SEQ ID NO:2   SPSWAADRSKDPPGRAPLPMGLGPLAPPPQPLPGELEPGDAASKRKR               2175
SEQ ID NO:4   SPSWAADRSKDPPGRAPLPMGLGPLAPPPQPLPGELEPGDAASKRKR               2188
```

Figure 2A

```
                           30 ↓ 31
SEQ ID NO:1     5148    ATGAAGGACACGCTGCGGGACTGCACCCACGACGAGCGCAGCTGCCTGAGCAGCCTGCAG
SEQ ID NO:3     5148    ATGAAGGACACGCTGCGGGACTGCACCCACGACGAGCGCAGCTGCCTGAGCAGCCTGCAG
SEQ ID NO:12    4927    ATGAAGGACACCCTGCGGAGACTGTACCCATGATGAGCGCACGTGCCTAAGCAGCCTGCAG
                                                                    CCTGAGCAGCCTGCAG

SEQ ID NO:1     5208    TTTGTGTCGCCCGCTGTACTTCGTGAGCTTCGTGTGCTCACCGGCAGTTCGTGTGCTCATCAAC
SEQ ID NO:3     5208    TTTGTGTCGCCCGCTGTACTTCGTGAGCTTCGTGTGCTCACCGGCAGTTCGTGTGCTCATCAAC
SEQ ID NO:12    4987    TTTGTGTCACCGCTCACTTTGTGAGCTTCGTGCTCACAGCTCAGTTCGTGTGCTCATCAAC
                        TTTGTGT→6066

SEQ ID NO:1     5268    GTGGTGGTGGCTGTGCTGCTCATGAAGCACCTGGACGACAGCAACAAGGAGGCGCAGGAGGAC
SEQ ID NO:3     5268    GTGGTGGTGGCTGTGCTGCTCATGAAGCACCTGGACGACAGCAACAAGGAGGCGCAGGAGGAC
SEQ ID NO:12    5047    GTGGTGGTGGCCGTGCTGCTGATGAAACATCTGGACGACAGCAACAAGGAGGCCCAGGAGGAT

SEQ ID NO:1     5328    GCCCGAGATGGATGCCGAGCTCGAGCTGGAGATGGCCCATGGCCCTGGGCCC------------
SEQ ID NO:3     5328    GCCCGAGATGGATGCCGAGCTCGAGCTGGAGATGGCCCATGGCCCTGGGCCC------------
SEQ ID NO:12    5107    GCAGAGATGGATGCTGAGATCGAGCTGGAGATGGCCCATGGCCCCTGCCCCTGGC

SEQ ID NO:1     5378    ------------------------------------------------TGGCCCGAGGCTGCCT
SEQ ID NO:3     5378    ------------------------------------------------TGGCCCGAGGCTGCCT
SEQ ID NO:12    5167    CCCTGCCCTGTCCCCTGCCCCTGCCCCTGTGCTGCCCGAGGCTGCCC

SEQ ID NO:1     5394    ACCGGCTCCCCGGGCGCCCCCTGGCCGGGAGGGCCGGGAGGGCGGGGGCGACACC
SEQ ID NO:3     5394    ACCGGCTCCCCGGGCGCCCCCTGGCCGGGAGGGCCGGGAGGGCGGGGGCGACACC
SEQ ID NO:12    5227    ACTAGTTCACCTGGCTCCGGGGCGAGGATCGGGAGGGCTGGAGGCGACACC
```

Figure 2B

```
                            31 ↓ 32
SEQ ID NO:1   5454  GAGGGGCGGCTTGTGCCGGCGCTGCTACTCGCCTGCCCAG--------------------
SEQ ID NO:3   5454  GAGGGCGGCTTGTGCCGCCGCTGCTACTCGCCTGCCCAG---------------------
SEQ ID NO:12  5287  GAGAGTCACCTGTGCCGCCGGCACTGCTATTCTCCAGCCACCTGTGGCTGGCTGGACAGC
                                           TCGCCTGCCCAGGAGAACCT→6352
                                           CTACTCGCCTGCCCAG---------

SEQ ID NO:1   5493  -----------------GACTCCTTGGAGGGGGAGCTGACCATCATCGACAAACCTGTCG
SEQ ID NO:3   5514  GTCTCTTAATCATCAAGGACTCCTTGGAGGGGGAGCTGACCATCATCGACAAACCTGTCG
SEQ ID NO:12  5347  GTCTCTTTAATCATCAAGGACTCCTTGGAGGGGGAGCTGACCATCATTGACAAACCTGTCT
                                        GACTC→6344/88

SEQ ID NO:1   5535  GGCTCCATCTTCCACCACTACTCCTGCCTGCCGGCTGCAAGAAGTGTCACCACGACAAG
SEQ ID NO:3   5574  GGCTCCATCTTCCACCACTACTCCTGCCTGCCGGCTGCAAGAAGTGTCACCACGACAAG
SEQ ID NO:12  5407  GGGTCCGTCTTCCACCACTACGCCTCACCTGACGGCTGTGCCAAGTGCCAAGTGTCACCATGACAAG
                                                                        ACCACGACAAG
                                                                        ACCACGACAAG

32 ↓ 33
SEQ ID NO:1   5595  CAAGAGGTGCAGCTGGCTGAGACGGAGGCCTTCTCCCTGAACTCAGACAGGTCCTCGTCC
SEQ ID NO:3   5634  CAAGAGGTGCAGCTGGCTGAGACGGAGGCCTTCTCCCTGAACTCAGACAGGTCCTCGTCC
SEQ ID NO:12  5467  CAAGAG------------------------------------------ACAGGTCTTCATCC
                    CAAGAGGTGC→6495
                    CAAGAG-----

SEQ ID NO:1   5655  ATCCTGCTGGGTGACGACCTGAGTCTCGAGGACCCCACAGCCTGCCACCTGGCCGCAAG
SEQ ID NO:3   5694  ATCCTGCTGGGTGACGACCTGAGTCTCGAGGACCCCACAGCCTGCCACCTGGCCGCAAA
SEQ ID NO:12  5487  ATCCTGCTGGGGGATGACCTGAGTCTTGAGGACCCCACGGCCTGCCCACAGGGCCCCAAG
                                                                        ACAGGT→6495/37
```

Figure 2C

```
                                      33 ↓ 34
SEQ ID NO:1   5715  GACAGCAAGGGTGAGCTGAGCTGGACCCCACCTGAGCCCCATGCCGTGTGGGAGAGACCTGGGCGAATGC
SEQ ID NO:3   5754  GACAGCAAGGGTGAGCTGAGCTGGACCTGAGCTGGACCCCACCTGAGCCCCATGCCGTGTGGGAGAGACCTGGGCGAATGC
SEQ ID NO:12  5547  GAGAGCAAGGGTGAACTAGAGAGCCTCCGGAGCCTCCGGAGCCTCCGGAGCCCCATGCGCAGGCTGGAGACCTGGATGAATGC

SEQ ID NO:1   5775  TTCTTCCCCTTGTCC-TCTACGGCCGTCTCGCCGGATCCAGAGAACTTCCTGTGTGAGATG
SEQ ID NO:3   5814  TTCTTCCCCTTGTCC-TCTACGGCCGTCTCGCCGGATCCAGAGAACTTCCTGTGTGAGATG
SEQ ID NO:12  5607  TTTTGGCCCTTTGCCAAGCGAGCCAGTGTCCACAGGCCCAGAGAGAGCCTGCTGTGCGAGATG
                                                                  34 ↓ 35
SEQ ID NO:1   5835  GAGGAGATCCCATTCAACCCTGTCCGGTCCTGGCTGAAACATGACAGCAGTCAAGCACCC
SEQ ID NO:3   5874  GAGGAGATCCCATTCAACCCTGTCCGGTCCTGGCTGAAACATGACAGCAGTCAAGCACCC
SEQ ID NO:12  5667  GGGGCCATTCCATTCAACCCTGTCCAGTCCTGGCTCAAACACGAGAGCAGCCAAGCACCC

SEQ ID NO:1   5895  CCAAGTCCCCTTCTCCCCCGGATGCCTCCCAGCCCTCCTGCCCATGCCAGCCGAGTTCTTC
SEQ ID NO:3   5934  CCAAGTCCCCTTCTCCTCCCCCGGATGCCTCCCAGCCCTCCTGCCCATGCCAGCCGAGTTCTTC
SEQ ID NO:12  5727  CAGAGCCCCTTTCTCCCCCGGATGCCTCCCAGCCCTCCTGTAGATGCCTGCTGAGTTCTTC
                                                                  6831 ←CTCAAGAAG
SEQ ID NO:1   5955  CACCCTGCAGTGTCTGCCAGCCAGCCAGAAAGGGCACTGGCACTGGAACCCTC
SEQ ID NO:3   5994  CACCCTGCAGTGTCTGCCAGCCAGCCAGAAAGGGCACTGGCACTGGAACCCTC
SEQ ID NO:12  5787  CACCCTGCTGTGTCTGCCAGCCAGAAGGGGCAGGAACCGGCAGGAACCGGCAGGAGTGCAGGAACCCTG
                    GTGGGACGTCACAGAC
```

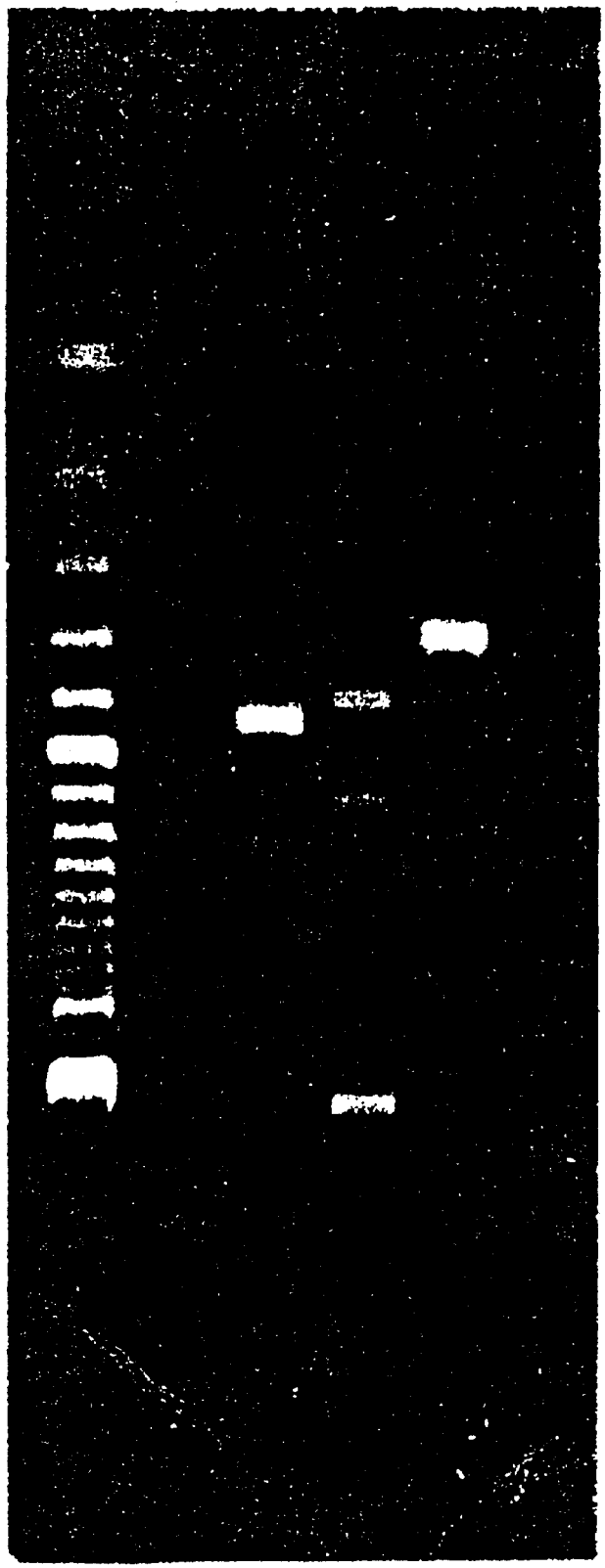

SEQUENCE LISTING

<160> NUMBER OF SEQ ID NOS: 12

<210> SEQ ID NO 1
<211> LENGTH: 6816
<212> TYPE: DNA
<213> ORGANISM: Homo sapiens
<220> FEATURE:
<221> NAME/KEY: CDS
<222> LOCATION: (192)..(6716)

<400> SEQUENCE: 1

```
ctgggccctc agctgtttcg taatcctcat gcaagagtga gggtgagggg cctgtgggc       60 tcaggtgggg ctgtcagagc tgcatccgtc cacttattgg tggagaggca ggttggggag     120
catgtaccag gcctgtcccc accacgtgcc accctctctg tcttccccag ggctcccagc     180
tcagtgtgga c atg gct gag agc gcc tcc ccg ccc tcc tca tct gca gca       230
            Met Ala Glu Ser Ala Ser Pro Pro Ser Ser Ser Ala Ala
              1               5                  10 gcc cca gcc gct gag cca gga gtc acc acg gag cag ccc gga ccc cgg      278
Ala Pro Ala Ala Glu Pro Gly Val Thr Thr Glu Gln Pro Gly Pro Arg
         15                  20                  25 agc ccc cca tcc tcc ccg cca ggc ctg gag gag cct ctg gat gga gct      326
Ser Pro Pro Ser Ser Pro Pro Gly Leu Glu Glu Pro Leu Asp Gly Ala
 30                  35                  40                  45 gat cct cat gtc cca cac cca gac ctg gcg cct att gcc ttc ttc tgc      374
Asp Pro His Val Pro His Pro Asp Leu Ala Pro Ile Ala Phe Phe Cys
                 50                  55                  60 ctg cga cag acc acc agc ccc cgg aac tgg tgc atc aag atg gtg tgc      422
Leu Arg Gln Thr Thr Ser Pro Arg Asn Trp Cys Ile Lys Met Val Cys
             65                  70                  75 aac ccg tgg ttt gaa tgt gtc agc atg ctg gtg atc ctg ctg aac tgc      470
Asn Pro Trp Phe Glu Cys Val Ser Met Leu Val Ile Leu Leu Asn Cys
         80                  85                  90 gtg aca ctt ggc atg tac cag ccg tgc gac gac atg gac tgc ctg tcc      518
Val Thr Leu Gly Met Tyr Gln Pro Cys Asp Asp Met Asp Cys Leu Ser
 95                 100                 105 gac cgc tgc aag atc ctg cag gtc ttt gat gac ttc atc ttt atc ttc      566
```

```
Asp Arg Cys Lys Ile Leu Gln Val Phe Asp Asp Phe Ile Phe Ile Phe
110             115                 120                 125 ttt gcc atg gag atg gtg ctc aag atg gtg gcc ctg ggg att ttt ggc         614
Phe Ala Met Glu Met Val Leu Lys Met Val Ala Leu Gly Ile Phe Gly
                130                 135                 140 aag aag tgc tac ctc ggg gac aca tgg aac cgc ctg gat ttc ttc atc         662
Lys Lys Cys Tyr Leu Gly Asp Thr Trp Asn Arg Leu Asp Phe Phe Ile
            145                 150                 155 gtc atg gca ggg atg gtc gag tac tcc ctg gac ctt cag aac atc aac         710
Val Met Ala Gly Met Val Glu Tyr Ser Leu Asp Leu Gln Asn Ile Asn
        160                 165                 170 ctg tca gcc atc cgc acc gtg cgc gtc ctg agg ccc ctc aaa gcc atc         758
Leu Ser Ala Ile Arg Thr Val Arg Val Leu Arg Pro Leu Lys Ala Ile
    175                 180                 185 aac cgc gtg ccc agt atg cgg atc ctg gtg aac ctc ctg gac aca             806
Asn Arg Val Pro Ser Met Arg Ile Leu Val Asn Leu Leu Leu Asp Thr
190                 195                 200                 205 ctg ccc atg ctg ggg aat gtc ctg ctc tgc ttc ttt gtc ttc ttc             854
Leu Pro Met Leu Gly Asn Val Leu Leu Leu Cys Phe Phe Val Phe Phe
                210                 215                 220 atc ttt ggc atc ata ggt gtg cag ctc tgg gcg ggc ctg ctg cgt aac         902
Ile Phe Gly Ile Ile Gly Val Gln Leu Trp Ala Gly Leu Leu Arg Asn
            225                 230                 235 cgc tgc ttc ctg gag gag aac ttc acc ata caa ggg gat gtg gcc ttg         950
Arg Cys Phe Leu Glu Glu Asn Phe Thr Ile Gln Gly Asp Val Ala Leu
        240                 245                 250 ccc cca tac tac cag ccg gag gag gat gat gag atg ccc ttc atc tgc         998
Pro Pro Tyr Tyr Gln Pro Glu Glu Asp Asp Glu Met Pro Phe Ile Cys
    255                 260                 265 tcc ctg tcg ggc gac aat ggg ata atg ggc tgc cat gag atc ccc ccg        1046
Ser Leu Ser Gly Asp Asn Gly Ile Met Gly Cys His Glu Ile Pro Pro
270                 275                 280                 285 ctc aag gag cag ggc cgt gag tgc tgc ctg tcc aag gac gac gtc tac        1094
Leu Lys Glu Gln Gly Arg Glu Cys Cys Leu Ser Lys Asp Asp Val Tyr
                290                 295                 300 gac ttt ggg gcg ggg cgc cag gac ctc aat gcc agc ggc ctc tgt gtc        1142
Asp Phe Gly Ala Gly Arg Gln Asp Leu Asn Ala Ser Gly Leu Cys Val
            305                 310                 315 aac tgg aac cgt tac tac aat gtg tgc cgc acg ggc agc gcc aac ccc        1190
Asn Trp Asn Arg Tyr Tyr Asn Val Cys Arg Thr Gly Ser Ala Asn Pro
        320                 325                 330 cac aag ggt gcc atc aac ttt gac aac atc ggt tat gct tgg att gtc        1238
His Lys Gly Ala Ile Asn Phe Asp Asn Ile Gly Tyr Ala Trp Ile Val
    335                 340                 345 atc ttc cag gtg atc act ctg gaa ggc tgg gtg gag atc atg tac tac        1286
Ile Phe Gln Val Ile Thr Leu Glu Gly Trp Val Glu Ile Met Tyr Tyr
350                 355                 360                 365 gtg atg gat gct cac tcc ttc tac aac ttc atc tac ttc atc ctg ctt        1334
Val Met Asp Ala His Ser Phe Tyr Asn Phe Ile Tyr Phe Ile Leu Leu
                370                 375                 380 atc ata gtg ggc tcc ttc ttc atg atc aac ctg tgc ctc gtt gtc ata        1382
Ile Ile Val Gly Ser Phe Phe Met Ile Asn Leu Cys Leu Val Val Ile
            385                 390                 395 gcg acc cag ttc tcg gag acc aag caa cgg gag cac cgg ctg atg ctg        1430
Ala Thr Gln Phe Ser Glu Thr Lys Gln Arg Glu His Arg Leu Met Leu
        400                 405                 410 gag cag cgg cag cgc tac ctg tcc tcc agc acg gtg gcc agc tac gcc        1478
Glu Gln Arg Gln Arg Tyr Leu Ser Ser Ser Thr Val Ala Ser Tyr Ala
    415                 420                 425
```

-continued

| | | |
|---|---|---|
| gag cct ggc gac tgc tac gag gag atc ttc cag tat gtc tgc cac atc<br>Glu Pro Gly Asp Cys Tyr Glu Glu Ile Phe Gln Tyr Val Cys His Ile<br>430                         435                      440                         445 | 1526 |
| ctg cgc aag gcc aag cgc cgc gcc ctg ggc ctc tac cag gcc ctg cag<br>Leu Arg Lys Ala Lys Arg Arg Ala Leu Gly Leu Tyr Gln Ala Leu Gln<br>                       450                       455                       460 | 1574 |
| agc cgg cgc cag gcc ctg ggc ccg gag gcc ccg gcc ccc gcc aaa cct<br>Ser Arg Arg Gln Ala Leu Gly Pro Glu Ala Pro Ala Pro Ala Lys Pro<br>             465                       470                       475 | 1622 |
| ggg ccc cac gcc aag gag ccc cgg cac tac cag ctg tgc ccg caa cat<br>Gly Pro His Ala Lys Glu Pro Arg His Tyr Gln Leu Cys Pro Gln His<br>480                         485                      490 | 1670 |
| agc ccc ctg gat gcg acg ccc cac acc ctg gtg cag ccc atc ccc gcc<br>Ser Pro Leu Asp Ala Thr Pro His Thr Leu Val Gln Pro Ile Pro Ala<br>495                       500                      505 | 1718 |
| acg ctg gct tcc gat ccc gcc agc tgc cct tgc tgc cag cat gag gac<br>Thr Leu Ala Ser Asp Pro Ala Ser Cys Pro Cys Cys Gln His Glu Asp<br>510                       515                      520                      525 | 1766 |
| ggc cgg cgg ccc tcg ggc ctg ggc agc acc gac tcg ggc cag gag ggc<br>Gly Arg Arg Pro Ser Gly Leu Gly Ser Thr Asp Ser Gly Gln Glu Gly<br>                       530                       535                       540 | 1814 |
| tcg ggc tcc ggg agc tcc gct ggt ggc gag gac gag gcg gat ggg gac<br>Ser Gly Ser Gly Ser Ser Ala Gly Gly Glu Asp Glu Ala Asp Gly Asp<br>             545                       550                       555 | 1862 |
| ggg gcc cgg agc agc gag gac gga gcc tcc tca gaa ctg ggg aag gag<br>Gly Ala Arg Ser Ser Glu Asp Gly Ala Ser Ser Glu Leu Gly Lys Glu<br>560                         565                      570 | 1910 |
| gag gag gag gag gag cag gcg gat ggg gcg gtc tgg ctg tgc ggg gat<br>Glu Glu Glu Glu Glu Gln Ala Asp Gly Ala Val Trp Leu Cys Gly Asp<br>575                         580                      585 | 1958 |
| gtg tgg cgg gag acg cga gcc aag ctg cgc ggc atc gtg gac agc aag<br>Val Trp Arg Glu Thr Arg Ala Lys Leu Arg Gly Ile Val Asp Ser Lys<br>590                       595                      600                      605 | 2006 |
| tac ttc aac cgg ggc atc atg atg gcc atc ctg gtc aac acc gtc agc<br>Tyr Phe Asn Arg Gly Ile Met Met Ala Ile Leu Val Asn Thr Val Ser<br>                       610                       615                      620 | 2054 |
| atg ggc atc gag cac cac gag cag ccg gag gag ctg acc aac atc ctg<br>Met Gly Ile Glu His His Glu Gln Pro Glu Glu Leu Thr Asn Ile Leu<br>             625                       630                      635 | 2102 |
| gag atc tgc aat gtg gtc ttc acc agc atg ttt gcc ctg gag atg atc<br>Glu Ile Cys Asn Val Val Phe Thr Ser Met Phe Ala Leu Glu Met Ile<br>640                         645                      650 | 2150 |
| ctg aag ctg gct gca ttt ggg ctc ttc gac tac ctg cgt aac ccc tac<br>Leu Lys Leu Ala Ala Phe Gly Leu Phe Asp Tyr Leu Arg Asn Pro Tyr<br>655                         660                      665 | 2198 |
| aac atc ttc gac agc atc att gtc atc atc agc atc tgg gag atc gtg<br>Asn Ile Phe Asp Ser Ile Ile Val Ile Ile Ser Ile Trp Glu Ile Val<br>670                         675                      680                      685 | 2246 |
| ggg cag gcg gac ggt ggg ctg tcg gtg ctg cgg acc ttc cgg ctg ctg<br>Gly Gln Ala Asp Gly Gly Leu Ser Val Leu Arg Thr Phe Arg Leu Leu<br>                       690                       695                      700 | 2294 |
| cgc gtg ctg aaa ctg gtg cgc ttc atg cct gcc ctg cgg cgc cag ctc<br>Arg Val Leu Lys Leu Val Arg Phe Met Pro Ala Leu Arg Arg Gln Leu<br>             705                       710                      715 | 2342 |
| gtg gtg ctc atg aag acc atg gac aac gtg gcc acc ttc tgc atg ctg<br>Val Val Leu Met Lys Thr Met Asp Asn Val Ala Thr Phe Cys Met Leu<br>720                         725                      730 | 2390 |
| ctc atg ctc ttc atc ttc atc ttc agc atc ctt ggg atg cat att ttt<br>Leu Met Leu Phe Ile Phe Ile Phe Ser Ile Leu Gly Met His Ile Phe<br>735                         740                      745 | 2438 |

-continued

| | |
|---|---|
| ggc tgc aag ttc agc ctc cgc acg gac act gga gac acg gtg ccc gac<br>Gly Cys Lys Phe Ser Leu Arg Thr Asp Thr Gly Asp Thr Val Pro Asp<br>750                  755                  760                765 | 2486 |
| agg aag aac ttc gac tcc ctg ctg tgg gcc atc gtc act gtg ttc cag<br>Arg Lys Asn Phe Asp Ser Leu Leu Trp Ala Ile Val Thr Val Phe Gln<br>                  770                  775                  780 | 2534 |
| atc ctc acc cag gag gac tgg aac gtc gtt ctc tac aat ggc atg gcc<br>Ile Leu Thr Gln Glu Asp Trp Asn Val Val Leu Tyr Asn Gly Met Ala<br>              785                  790                  795 | 2582 |
| tcc act tct ccc tgg gcc tcc ctc tac ttt gtc gcc ctc atg acc ttc<br>Ser Thr Ser Pro Trp Ala Ser Leu Tyr Phe Val Ala Leu Met Thr Phe<br>           800                  805                  810 | 2630 |
| ggc aac tat gtg ctc ttc aac ctg ctg gtg gcc atc ctg gtg gag ggc<br>Gly Asn Tyr Val Leu Phe Asn Leu Leu Val Ala Ile Leu Val Glu Gly<br>815                  820                  825 | 2678 |
| ttc cag gcg gag ggt gac gcc aat cgc tcc tac tcg gac gag gac cag<br>Phe Gln Ala Glu Gly Asp Ala Asn Arg Ser Tyr Ser Asp Glu Asp Gln<br>830                  835                  840                  845 | 2726 |
| agc tca tcc aac ata gaa gag ttt gat aag ctc cag gaa ggc ctg gac<br>Ser Ser Ser Asn Ile Glu Glu Phe Asp Lys Leu Gln Glu Gly Leu Asp<br>              850                  855                  860 | 2774 |
| agc agc gga gat ccc aag ctc tgc cca atc ccc atg acc ccc aat ggg<br>Ser Ser Gly Asp Pro Lys Leu Cys Pro Ile Pro Met Thr Pro Asn Gly<br>              865                  870                  875 | 2822 |
| cac ctg gac ccc agt ctc cca ctg ggt ggg cac cta ggt cct gct ggg<br>His Leu Asp Pro Ser Leu Pro Leu Gly Gly His Leu Gly Pro Ala Gly<br>           880                  885                  890 | 2870 |
| gct gcg gga cct gcc ccc cga ctc tca ctg cag ccg gac ccc atg ctg<br>Ala Ala Gly Pro Ala Pro Arg Leu Ser Leu Gln Pro Asp Pro Met Leu<br>895                  900                  905 | 2918 |
| gtg gcc ctg ggc tcc cga aag agc agt gtc atg tct cta ggg agg atg<br>Val Ala Leu Gly Ser Arg Lys Ser Ser Val Met Ser Leu Gly Arg Met<br>910                  915                  920                925 | 2966 |
| agc tat gac cag cgc tcc ctg tcc agc tcc cgg agc tcc tac tac ggg<br>Ser Tyr Asp Gln Arg Ser Leu Ser Ser Arg Ser Ser Tyr Tyr Gly<br>              930                  935                  940 | 3014 |
| cca tgg ggc cgc agc gcg gcc tgg gcc agc cgt cgc tcc agc tgg aac<br>Pro Trp Gly Arg Ser Ala Ala Trp Ala Ser Arg Arg Ser Ser Trp Asn<br>                  945                  950                  955 | 3062 |
| agc ctc aag cac aag ccg ccg tcg gcg gag cat gag tcc ctg ctc tct<br>Ser Leu Lys His Lys Pro Pro Ser Ala Glu His Glu Ser Leu Leu Ser<br>           960                  965                  970 | 3110 |
| gcg gag cgc ggc ggc gcc cgg gtc tgc gag gtt gcc gcg gac gag<br>Ala Glu Arg Gly Gly Gly Ala Arg Val Cys Glu Val Ala Ala Asp Glu<br>975                  980                  985 | 3158 |
| ggg ccg ccg cgg gcc gca ccc ctg cac acc cca cac gcc cac cac att<br>Gly Pro Pro Arg Ala Ala Pro Leu His Thr Pro His Ala His His Ile<br>990                  995                  1000              1005 | 3206 |
| cat cac ggg ccc cat ctg gcg cac cgc cac cgc cac cac cgc cgg acg<br>His His Gly Pro His Leu Ala His Arg His Arg His His Arg Arg Thr<br>              1010                  1015                  1020 | 3254 |
| ctg tcc ctc gac aac agg gac tcg gtg gac ctg gcc gag ctg gtg ccc<br>Leu Ser Leu Asp Asn Arg Asp Ser Val Asp Leu Ala Glu Leu Val Pro<br>                  1025                  1030                  1035 | 3302 |
| gcg gtg ggc gcc cac ccc cgg gcc gcc tgg agg gcg gca ggc ccg gcc<br>Ala Val Gly Ala His Pro Arg Ala Ala Trp Arg Ala Ala Gly Pro Ala<br>              1040                  1045                  1050 | 3350 |
| ccc ggg cat gag gac tgc aat ggc agg atg ccc agc atc gcc aaa gac<br>Pro Gly His Glu Asp Cys Asn Gly Arg Met Pro Ser Ile Ala Lys Asp | 3398 |

-continued

```
          1055                1060                1065
gtc ttc acc aag atg ggc gac cgc ggg gat cgc ggg gag gat gag gag    3446
Val Phe Thr Lys Met Gly Asp Arg Gly Asp Arg Gly Glu Asp Glu Glu
1070                1075                1080                1085 gaa atc gac tac acc ctg tgc ttc cgc gtc cgc aag atg atc gac gtc    3494
Glu Ile Asp Tyr Thr Leu Cys Phe Arg Val Arg Lys Met Ile Asp Val
        1090                1095                1100 tat aag ccc gac tgg tgc gag gtc cgc gaa gac tgg tct gtc tac ctc    3542
Tyr Lys Pro Asp Trp Cys Glu Val Arg Glu Asp Trp Ser Val Tyr Leu
    1105                1110                1115 ttc tct ccc gag aac agg ttc cgg gtc ctg tgt cag acc att att gcc    3590
Phe Ser Pro Glu Asn Arg Phe Arg Val Leu Cys Gln Thr Ile Ile Ala
        1120                1125                1130 cac aaa ctc ttc gac tac gtc gtc ctg gcc ttc atc ttt ctc aac tgc    3638
His Lys Leu Phe Asp Tyr Val Val Leu Ala Phe Ile Phe Leu Asn Cys
    1135                1140                1145 atc acc atc gcc ctg gag cgg cct cag atc gag gcc ggc agc acc gaa    3686
Ile Thr Ile Ala Leu Glu Arg Pro Gln Ile Glu Ala Gly Ser Thr Glu
1150                1155                1160                1165 cgc atc ttt ctc acc gtg tcc aac tac atc ttc acg gcc atc ttc gtg    3734
Arg Ile Phe Leu Thr Val Ser Asn Tyr Ile Phe Thr Ala Ile Phe Val
        1170                1175                1180 ggc gag atg aca ttg aag gta gtc tcg ctg ggc ctg tac ttc ggc gag    3782
Gly Glu Met Thr Leu Lys Val Val Ser Leu Gly Leu Tyr Phe Gly Glu
    1185                1190                1195 cag gcg tac cta cgc agc agc tgg aac gtg ctg gat ggc ttt ctt gtc    3830
Gln Ala Tyr Leu Arg Ser Ser Trp Asn Val Leu Asp Gly Phe Leu Val
        1200                1205                1210 ttc gtg tcc atc atc gac atc gtg gtg tcc ctg gcc tca gcg ggg gga    3878
Phe Val Ser Ile Ile Asp Ile Val Val Ser Leu Ala Ser Ala Gly Gly
    1215                1220                1225 gcc aag atc ttg ggg gtc ctc cga gtc ttg cgg ctc ctg cgc acc cta    3926
Ala Lys Ile Leu Gly Val Leu Arg Val Leu Arg Leu Leu Arg Thr Leu
1230                1235                1240                1245 cgc ccc ctg cgt gtc atc agc cgg gcg ccg ggc ctg aag ctg gtg gtg    3974
Arg Pro Leu Arg Val Ile Ser Arg Ala Pro Gly Leu Lys Leu Val Val
        1250                1255                1260 gag aca ctc atc tcc tcc ctc aag ccc atc ggc aac atc gtg ctc atc    4022
Glu Thr Leu Ile Ser Ser Leu Lys Pro Ile Gly Asn Ile Val Leu Ile
    1265                1270                1275 tgc tgt gcc ttc ttc atc atc ttt ggc atc ctg gga gtg cag ctc ttc    4070
Cys Cys Ala Phe Phe Ile Ile Phe Gly Ile Leu Gly Val Gln Leu Phe
        1280                1285                1290 aag ggc aag ttc tac cac tgt ctg ggc gtg gac acc cgc aac atc acc    4118
Lys Gly Lys Phe Tyr His Cys Leu Gly Val Asp Thr Arg Asn Ile Thr
    1295                1300                1305 aac cgc tcg gac tgc atg gcc gcc aac tac cgc tgg gtc cat cac aaa    4166
Asn Arg Ser Asp Cys Met Ala Ala Asn Tyr Arg Trp Val His His Lys
1310                1315                1320                1325 tac aac ttc gac aac ctg ggc cag gct ctg atg tcc ctc ttt gtc ctg    4214
Tyr Asn Phe Asp Asn Leu Gly Gln Ala Leu Met Ser Leu Phe Val Leu
        1330                1335                1340 gca tcc aag gat ggt tgg gtg aac atc atg tac aat gga ctg gat gct    4262
Ala Ser Lys Asp Gly Trp Val Asn Ile Met Tyr Asn Gly Leu Asp Ala
    1345                1350                1355 gtt gct gtg gac cag cag cct gtg acc aac cac aac ccc tgg atg ctg    4310
Val Ala Val Asp Gln Gln Pro Val Thr Asn His Asn Pro Trp Met Leu
        1360                1365                1370 ctg tac ttc atc tcc ttc ctg ctc atc gtc agc ttc ttt gtg ctc aac    4358
```

-continued

```
Leu Tyr Phe Ile Ser Phe Leu Leu Ile Val Ser Phe Val Leu Asn
    1375             1380             1385 atg ttt gtg ggt gtc gtg gtg gag aac ttc cac aag tgc cgg cag cac      4406
Met Phe Val Gly Val Val Val Glu Asn Phe His Lys Cys Arg Gln His
1390             1395             1400             1405 cag gag gct gaa gag gca cgg cgg cgt gag gag aag cgg ctg cgg cgc      4454
Gln Glu Ala Glu Glu Ala Arg Arg Arg Glu Glu Lys Arg Leu Arg Arg
             1410             1415             1420 ctg gag aag aag cgc cgg aag gcc cag cgg ctg ccc tac tat gcc acc      4502
Leu Glu Lys Lys Arg Arg Lys Ala Gln Arg Leu Pro Tyr Tyr Ala Thr
         1425             1430             1435 tat tgt cac acc cgg ctg ctc atc cac tcc atg tgc acc agc cac tac      4550
Tyr Cys His Thr Arg Leu Leu Ile His Ser Met Cys Thr Ser His Tyr
     1440             1445             1450 ctg gac atc ttc atc acc ttc atc atc tgc ctc aac gtg gtc acc atg      4598
Leu Asp Ile Phe Ile Thr Phe Ile Ile Cys Leu Asn Val Val Thr Met
 1455             1460             1465 tcc ctg gag cac tac aat cag ccc acg tcc ctg gag aca gcc ctc aag      4646
Ser Leu Glu His Tyr Asn Gln Pro Thr Ser Leu Glu Thr Ala Leu Lys
1470             1475             1480             1485 tac tgc aac tat atg ttc acc act gtc ttt gtg ctg gag gct gtg ctg      4694
Tyr Cys Asn Tyr Met Phe Thr Thr Val Phe Val Leu Glu Ala Val Leu
             1490             1495             1500 aag ctg gtg gca ttt ggt ctg agg cgc ttc ttc aag gac cga tgg aac      4742
Lys Leu Val Ala Phe Gly Leu Arg Arg Phe Phe Lys Asp Arg Trp Asn
         1505             1510             1515 cag ctg gac ctg gcc att gtg cta ctg tca gtc atg ggc atc acc ctg      4790
Gln Leu Asp Leu Ala Ile Val Leu Leu Ser Val Met Gly Ile Thr Leu
     1520             1525             1530 gag gag atc gag atc aat gcg gcc ctg ccc atc aat ccc acc atc atc      4838
Glu Glu Ile Glu Ile Asn Ala Ala Leu Pro Ile Asn Pro Thr Ile Ile
 1535             1540             1545 cgc atc atg agg gtt ctg cgc att gcc cga gtg ctg aag ctg ttg aag      4886
Arg Ile Met Arg Val Leu Arg Ile Ala Arg Val Leu Lys Leu Leu Lys
1550             1555             1560             1565 atg gcc aca gga atg cgg gcc ctg ctg gac acg gtg gtg caa gct ttg      4934
Met Ala Thr Gly Met Arg Ala Leu Leu Asp Thr Val Val Gln Ala Leu
             1570             1575             1580 ccc cag gtg ggc aac ctg ggc ctc ctc ttc atg ctg ctc ttc ttc atc      4982
Pro Gln Val Gly Asn Leu Gly Leu Leu Phe Met Leu Leu Phe Phe Ile
         1585             1590             1595 tat gct gct ctc ggg gtg gag ctc ttt ggg aag ctg gtc tgc aac gac      5030
Tyr Ala Ala Leu Gly Val Glu Leu Phe Gly Lys Leu Val Cys Asn Asp
     1600             1605             1610 gag aac ccg tgc gag ggc atg agc cgg cat gcc acc ttc gag aac ttc      5078
Glu Asn Pro Cys Glu Gly Met Ser Arg His Ala Thr Phe Glu Asn Phe
 1615             1620             1625 ggc atg gcc ttc ctc aca ctc ttc cag gtc tcc acg ggt gac aac tgg      5126
Gly Met Ala Phe Leu Thr Leu Phe Gln Val Ser Thr Gly Asp Asn Trp
1630             1635             1640             1645 aac ggg atc atg aag gac acg ctg cgg gac tgc acc cac gac gag cgc      5174
Asn Gly Ile Met Lys Asp Thr Leu Arg Asp Cys Thr His Asp Glu Arg
             1650             1655             1660 agc tgc ctg agc agc ctg cag ttt gtg tcg ccg ctg tac ttc gtg agc      5222
Ser Cys Leu Ser Ser Leu Gln Phe Val Ser Pro Leu Tyr Phe Val Ser
         1665             1670             1675 ttc gtg ctc acc gcg cag ttc gtg ctc atc aac gtg gtg gtg gct gtg      5270
Phe Val Leu Thr Ala Gln Phe Val Leu Ile Asn Val Val Val Ala Val
     1680             1685             1690
```

```
ctc atg aag cac ctg gac gac agc aac aag gag gcg cag gag gac gcc     5318
Leu Met Lys His Leu Asp Asp Ser Asn Lys Glu Ala Gln Glu Asp Ala
    1695                1700                1705 gag atg gat gcc gag ctc gag ctg gag atg gcc cat ggc ctg ggc cct     5366
Glu Met Asp Ala Glu Leu Glu Leu Glu Met Ala His Gly Leu Gly Pro
1710                1715                1720                1725 ggc ccg agg ctg cct acc ggc tcc ccg ggc gcc cct ggc cga ggg ccg     5414
Gly Pro Arg Leu Pro Thr Gly Ser Pro Gly Ala Pro Gly Arg Gly Pro
            1730                1735                1740 gga ggg gcg ggc ggc ggg ggc gac acc gag ggc ggc ttg tgc cgg cgc     5462
Gly Gly Ala Gly Gly Gly Gly Asp Thr Glu Gly Gly Leu Cys Arg Arg
        1745                1750                1755 tgc tac tcg cct gcc cag gac tcc ttg gag ggg gag ctg acc atc atc     5510
Cys Tyr Ser Pro Ala Gln Asp Ser Leu Glu Gly Glu Leu Thr Ile Ile
    1760                1765                1770 gac aac ctg tcg ggc tcc atc ttc cac cac tac tcc tcg cct gcc ggc     5558
Asp Asn Leu Ser Gly Ser Ile Phe His His Tyr Ser Ser Pro Ala Gly
1775                1780                1785 tgc aag aag tgt cac cac gac aag caa gag gtg cag ctg gct gag acg     5606
Cys Lys Lys Cys His His Asp Lys Gln Glu Val Gln Leu Ala Glu Thr
1790                1795                1800                1805 gag gcc ttc tcc ctg aac tca gac agg tcc tcg tcc atc ctg ctg ggt     5654
Glu Ala Phe Ser Leu Asn Ser Asp Arg Ser Ser Ser Ile Leu Leu Gly
            1810                1815                1820 gac gac ctg agt ctc gag gac ccc aca gcc tgc cca cct ggc cgc aag     5702
Asp Asp Leu Ser Leu Glu Asp Pro Thr Ala Cys Pro Pro Gly Arg Lys
        1825                1830                1835 gac agc aag ggt gag ctg gac cca cct gag ccc atg cgt gtg gga gac     5750
Asp Ser Lys Gly Glu Leu Asp Pro Pro Glu Pro Met Arg Val Gly Asp
    1840                1845                1850 ctg ggc gaa tgc ttc ttc ccc ttg tcc tct acg gcc gtc tcg ccg gat     5798
Leu Gly Glu Cys Phe Phe Pro Leu Ser Ser Thr Ala Val Ser Pro Asp
1855                1860                1865 cca gag aac ttc ctg tgt gag atg gag gag atc cca ttc aac cct gtc     5846
Pro Glu Asn Phe Leu Cys Glu Met Glu Glu Ile Pro Phe Asn Pro Val
1870                1875                1880                1885 cgg tcc tgg ctg aaa cat gac agc agt caa gca ccc cca agt ccc ttc     5894
Arg Ser Trp Leu Lys His Asp Ser Ser Gln Ala Pro Pro Ser Pro Phe
            1890                1895                1900 tcc ccg gat gcc tcc agc cct ctc ctg ccc atg cca gcc gag ttc ttc     5942
Ser Pro Asp Ala Ser Ser Pro Leu Leu Pro Met Pro Ala Glu Phe Phe
        1905                1910                1915 cac cct gca gtg tct gcc agc cag aaa ggc cca gaa aag ggc act ggc     5990
His Pro Ala Val Ser Ala Ser Gln Lys Gly Pro Glu Lys Gly Thr Gly
    1920                1925                1930 act gga acc ctc ccc aag att gcg ctg cag ggc tcc tgg gca tct ctg     6038
Thr Gly Thr Leu Pro Lys Ile Ala Leu Gln Gly Ser Trp Ala Ser Leu
1935                1940                1945 cgg tca cca agg gtc aac tgt acc ctc ctc cgg cag gcc acc ggg agc     6086
Arg Ser Pro Arg Val Asn Cys Thr Leu Leu Arg Gln Ala Thr Gly Ser
1950                1955                1960                1965 gac acg tcg ctg gac gcc agc ccc agc agc tcg gcg ggc agc ctg cag     6134
Asp Thr Ser Leu Asp Ala Ser Pro Ser Ser Ser Ala Gly Ser Leu Gln
            1970                1975                1980 acc acg ctc gag gac agc ctg acc ctg agc gac agc ccc cgg cgt gcc     6182
Thr Thr Leu Glu Asp Ser Leu Thr Leu Ser Asp Ser Pro Arg Arg Ala
        1985                1990                1995 ctg ggg ccg ccc gcg cct gct cca gga ccc cgg gcc ggc ctg tcc ccc     6230
Leu Gly Pro Pro Ala Pro Ala Pro Gly Pro Arg Ala Gly Leu Ser Pro
    2000                2005                2010
```

```
gcc gct cgc cgc cgc ctg agc ctg cgc ggc cgg ggc ctc ttc agc ctg         6278
Ala Ala Arg Arg Arg Leu Ser Leu Arg Gly Arg Gly Leu Phe Ser Leu
    2015                2020                2025 cgg ggg ctg cgg gcg cat cag cgc agc cac agc agc ggg ggc tcc acc         6326
Arg Gly Leu Arg Ala His Gln Arg Ser His Ser Ser Gly Gly Ser Thr
2030                2035                2040                2045 agc ccg ggc tgc acc cac cac gac tcc atg gac ccc tcg gac gag gag         6374
Ser Pro Gly Cys Thr His His Asp Ser Met Asp Pro Ser Asp Glu Glu
            2050                2055                2060 ggc cgc ggt ggc gcg ggc ggc ggg ggc gcg ggc agc gag cac tcg gag         6422
Gly Arg Gly Gly Ala Gly Gly Gly Gly Ala Gly Ser Glu His Ser Glu
        2065                2070                2075 acc ctc agc agc ctc tcg ctc acc tcc ctc ttc tgc ccg ccg ccc ccg         6470
Thr Leu Ser Ser Leu Ser Leu Thr Ser Leu Phe Cys Pro Pro Pro Pro
            2080                2085                2090 ccg cca gcc ccc ggc ctc acg ccc gcc agg aag ttc agc agc acc agc         6518
Pro Pro Ala Pro Gly Leu Thr Pro Ala Arg Lys Phe Ser Ser Thr Ser
        2095                2100                2105 agc ctg gcc gcc ccc ggc cgc ccc cac gcc gcc gcc ctg gcc cac ggc         6566
Ser Leu Ala Ala Pro Gly Arg Pro His Ala Ala Ala Leu Ala His Gly
2110                2115                2120                2125 ctg gcc cgg agc ccc tcg tgg gcc gcg gac cgc agc aag gac ccc ccc         6614
Leu Ala Arg Ser Pro Ser Trp Ala Ala Asp Arg Ser Lys Asp Pro Pro
            2130                2135                2140 ggc cgg gca ccg ctg ccc atg ggc ctg ggc ccc ttg gcg ccc ccg ccg         6662
Gly Arg Ala Pro Leu Pro Met Gly Leu Gly Pro Leu Ala Pro Pro Pro
        2145                2150                2155 caa ccg ctc ccc gga gag ctg gag ccg gga gac gcc gcc agc aag agg         6710
Gln Pro Leu Pro Gly Glu Leu Glu Pro Gly Asp Ala Ala Ser Lys Arg
            2160                2165                2170 aag aga tgagggtcgc aggggccccc ggccgcccac cgcccgcccc gtctcacctt         6766
Lys Arg
    2175 ctttacctca ggagccagga gcagacagca atacttcgtc cacacctggg                 6816
```

<210> SEQ ID NO 2
<211> LENGTH: 2175
<212> TYPE: PRT
<213> ORGANISM: Homo sapiens

<400> SEQUENCE: 2

```
Met Ala Glu Ser Ala Ser Pro Pro Ser Ser Ala Ala Pro Ala
 1               5                  10                  15

Ala Glu Pro Gly Val Thr Thr Glu Gln Pro Gly Pro Arg Ser Pro Pro
            20                  25                  30

Ser Ser Pro Pro Gly Leu Glu Glu Pro Leu Asp Gly Ala Asp Pro His
        35                  40                  45

Val Pro His Pro Asp Leu Ala Pro Ile Ala Phe Phe Cys Leu Arg Gln
    50                  55                  60

Thr Thr Ser Pro Arg Asn Trp Cys Ile Lys Met Val Cys Asn Pro Trp
65                  70                  75                  80

Phe Glu Cys Val Ser Met Leu Val Ile Leu Leu Asn Cys Val Thr Leu
                85                  90                  95

Gly Met Tyr Gln Pro Cys Asp Asp Met Asp Cys Leu Ser Asp Arg Cys
            100                 105                 110

Lys Ile Leu Gln Val Phe Asp Asp Phe Ile Phe Ile Phe Ala Met
        115                 120                 125
```

-continued

Glu Met Val Leu Lys Met Val Ala Leu Gly Ile Phe Gly Lys Lys Cys
    130                 135                 140

Tyr Leu Gly Asp Thr Trp Asn Arg Leu Asp Phe Phe Ile Val Met Ala
145                 150                 155                 160

Gly Met Val Glu Tyr Ser Leu Asp Leu Gln Asn Ile Asn Leu Ser Ala
                165                 170                 175

Ile Arg Thr Val Arg Val Leu Arg Pro Leu Lys Ala Ile Asn Arg Val
            180                 185                 190

Pro Ser Met Arg Ile Leu Val Asn Leu Leu Asp Thr Leu Pro Met
        195                 200                 205

Leu Gly Asn Val Leu Leu Cys Phe Phe Val Phe Phe Ile Phe Gly
    210                 215                 220

Ile Ile Gly Val Gln Leu Trp Ala Gly Leu Leu Arg Asn Arg Cys Phe
225                 230                 235                 240

Leu Glu Glu Asn Phe Thr Ile Gln Gly Asp Val Ala Leu Pro Pro Tyr
                245                 250                 255

Tyr Gln Pro Glu Glu Asp Asp Glu Met Pro Phe Ile Cys Ser Leu Ser
            260                 265                 270

Gly Asp Asn Gly Ile Met Gly Cys His Glu Ile Pro Pro Leu Lys Glu
        275                 280                 285

Gln Gly Arg Glu Cys Cys Leu Ser Lys Asp Asp Val Tyr Asp Phe Gly
    290                 295                 300

Ala Gly Arg Gln Asp Leu Asn Ala Ser Gly Leu Cys Val Asn Trp Asn
305                 310                 315                 320

Arg Tyr Tyr Asn Val Cys Arg Thr Gly Ser Ala Asn Pro His Lys Gly
                325                 330                 335

Ala Ile Asn Phe Asp Asn Ile Gly Tyr Ala Trp Ile Val Ile Phe Gln
            340                 345                 350

Val Ile Thr Leu Glu Gly Trp Val Glu Ile Met Tyr Tyr Val Met Asp
        355                 360                 365

Ala His Ser Phe Tyr Asn Phe Ile Tyr Phe Ile Leu Leu Ile Ile Val
    370                 375                 380

Gly Ser Phe Phe Met Ile Asn Leu Cys Leu Val Val Ile Ala Thr Gln
385                 390                 395                 400

Phe Ser Glu Thr Lys Gln Arg Glu His Arg Leu Met Leu Glu Gln Arg
                405                 410                 415

Gln Arg Tyr Leu Ser Ser Ser Thr Val Ala Ser Tyr Ala Glu Pro Gly
            420                 425                 430

Asp Cys Tyr Glu Glu Ile Phe Gln Tyr Val Cys His Ile Leu Arg Lys
        435                 440                 445

Ala Lys Arg Arg Ala Leu Gly Leu Tyr Gln Ala Leu Gln Ser Arg Arg
    450                 455                 460

Gln Ala Leu Gly Pro Glu Ala Pro Ala Lys Pro Gly Pro His
465                 470                 475                 480

Ala Lys Glu Pro Arg His Tyr Gln Leu Cys Pro Gln His Ser Pro Leu
                485                 490                 495

Asp Ala Thr Pro His Thr Leu Val Gln Pro Ile Pro Ala Thr Leu Ala
            500                 505                 510

Ser Asp Pro Ala Ser Cys Pro Cys Cys Gln His Glu Asp Gly Arg Arg
        515                 520                 525

Pro Ser Gly Leu Gly Ser Thr Asp Ser Gly Gln Glu Gly Ser Gly Ser
    530                 535                 540

Gly Ser Ser Ala Gly Gly Glu Asp Glu Ala Asp Gly Asp Gly Ala Arg

```
545                 550                 555                 560

Ser Ser Glu Asp Gly Ala Ser Glu Leu Gly Lys Glu Glu Glu
                565                 570                 575

Glu Glu Gln Ala Asp Gly Ala Val Trp Leu Cys Gly Asp Val Trp Arg
            580                 585                 590

Glu Thr Arg Ala Lys Leu Arg Gly Ile Val Asp Ser Lys Tyr Phe Asn
        595                 600                 605

Arg Gly Ile Met Met Ala Ile Leu Val Asn Thr Val Ser Met Gly Ile
    610                 615                 620

Glu His His Glu Gln Pro Glu Leu Thr Asn Ile Leu Glu Ile Cys
625                 630                 635                 640

Asn Val Val Phe Thr Ser Met Phe Ala Leu Glu Met Ile Leu Lys Leu
            645                 650                 655

Ala Ala Phe Gly Leu Phe Asp Tyr Leu Arg Asn Pro Tyr Asn Ile Phe
            660                 665                 670

Asp Ser Ile Ile Val Ile Ile Ser Ile Trp Glu Ile Val Gly Gln Ala
        675                 680                 685

Asp Gly Gly Leu Ser Val Leu Arg Thr Phe Arg Leu Leu Arg Val Leu
    690                 695                 700

Lys Leu Val Arg Phe Met Pro Ala Leu Arg Arg Gln Leu Val Val Leu
705                 710                 715                 720

Met Lys Thr Met Asp Asn Val Ala Thr Phe Cys Met Leu Leu Met Leu
            725                 730                 735

Phe Ile Phe Ile Phe Ser Ile Leu Gly Met His Ile Phe Gly Cys Lys
            740                 745                 750

Phe Ser Leu Arg Thr Asp Thr Gly Asp Thr Val Pro Asp Arg Lys Asn
        755                 760                 765

Phe Asp Ser Leu Leu Trp Ala Ile Val Thr Val Phe Gln Ile Leu Thr
770                 775                 780

Gln Glu Asp Trp Asn Val Val Leu Tyr Asn Gly Met Ala Ser Thr Ser
785                 790                 795                 800

Pro Trp Ala Ser Leu Tyr Phe Val Ala Leu Met Thr Phe Gly Asn Tyr
            805                 810                 815

Val Leu Phe Asn Leu Leu Val Ala Ile Leu Val Glu Gly Phe Gln Ala
            820                 825                 830

Glu Gly Asp Ala Asn Arg Ser Tyr Ser Asp Glu Asp Gln Ser Ser Ser
        835                 840                 845

Asn Ile Glu Glu Phe Asp Lys Leu Gln Glu Gly Leu Asp Ser Ser Gly
850                 855                 860

Asp Pro Lys Leu Cys Pro Ile Pro Met Thr Pro Asn Gly His Leu Asp
865                 870                 875                 880

Pro Ser Leu Pro Leu Gly Gly His Leu Gly Pro Ala Gly Ala Ala Gly
            885                 890                 895

Pro Ala Pro Arg Leu Ser Leu Gln Pro Asp Pro Met Leu Val Ala Leu
        900                 905                 910

Gly Ser Arg Lys Ser Ser Val Met Ser Leu Gly Arg Met Ser Tyr Asp
    915                 920                 925

Gln Arg Ser Leu Ser Ser Arg Ser Tyr Tyr Gly Pro Trp Gly
    930                 935                 940

Arg Ser Ala Ala Trp Ala Ser Arg Arg Ser Ser Trp Asn Ser Leu Lys
945                 950                 955                 960

His Lys Pro Pro Ser Ala Glu His Glu Ser Leu Leu Ser Ala Glu Arg
            965                 970                 975
```

```
Gly Gly Gly Ala Arg Val Cys Glu Val Ala Ala Asp Glu Gly Pro Pro
            980                 985                 990

Arg Ala Ala Pro Leu His Thr Pro His Ala His His Ile His His Gly
            995                 1000                1005

Pro His Leu Ala His Arg His Arg His His Arg Thr Leu Ser Leu
            1010                1015                1020

Asp Asn Arg Asp Ser Val Asp Leu Ala Glu Leu Val Pro Ala Val Gly
1025                1030                1035                1040

Ala His Pro Arg Ala Ala Trp Arg Ala Ala Gly Pro Ala Pro Gly His
            1045                1050                1055

Glu Asp Cys Asn Gly Arg Met Pro Ser Ile Ala Lys Asp Val Phe Thr
            1060                1065                1070

Lys Met Gly Asp Arg Gly Asp Arg Gly Glu Asp Glu Glu Ile Asp
            1075                1080                1085

Tyr Thr Leu Cys Phe Arg Val Arg Lys Met Ile Asp Val Tyr Lys Pro
            1090                1095                1100

Asp Trp Cys Glu Val Arg Glu Asp Trp Ser Val Tyr Leu Phe Ser Pro
1105                1110                1115                1120

Glu Asn Arg Phe Arg Val Leu Cys Gln Thr Ile Ile Ala His Lys Leu
            1125                1130                1135

Phe Asp Tyr Val Val Leu Ala Phe Ile Phe Leu Asn Cys Ile Thr Ile
            1140                1145                1150

Ala Leu Glu Arg Pro Gln Ile Glu Ala Gly Ser Thr Glu Arg Ile Phe
            1155                1160                1165

Leu Thr Val Ser Asn Tyr Ile Phe Thr Ala Ile Phe Val Gly Glu Met
            1170                1175                1180

Thr Leu Lys Val Val Ser Leu Gly Leu Tyr Phe Gly Glu Gln Ala Tyr
1185                1190                1195                1200

Leu Arg Ser Ser Trp Asn Val Leu Asp Gly Phe Leu Val Phe Val Ser
            1205                1210                1215

Ile Ile Asp Ile Val Val Ser Leu Ala Ser Ala Gly Gly Ala Lys Ile
            1220                1225                1230

Leu Gly Val Leu Arg Val Leu Arg Leu Leu Arg Thr Leu Arg Pro Leu
            1235                1240                1245

Arg Val Ile Ser Arg Ala Pro Gly Leu Lys Leu Val Val Glu Thr Leu
            1250                1255                1260

Ile Ser Ser Leu Lys Pro Ile Gly Asn Ile Val Leu Ile Cys Cys Ala
1265                1270                1275                1280

Phe Phe Ile Ile Phe Gly Ile Leu Gly Val Gln Leu Phe Lys Gly Lys
            1285                1290                1295

Phe Tyr His Cys Leu Gly Val Asp Thr Arg Asn Ile Thr Asn Arg Ser
            1300                1305                1310

Asp Cys Met Ala Ala Asn Tyr Arg Trp Val His His Lys Tyr Asn Phe
            1315                1320                1325

Asp Asn Leu Gly Gln Ala Leu Met Ser Leu Phe Val Leu Ala Ser Lys
            1330                1335                1340

Asp Gly Trp Val Asn Ile Met Tyr Asn Gly Leu Asp Ala Val Ala Val
1345                1350                1355                1360

Asp Gln Gln Pro Val Thr Asn His Asn Pro Trp Met Leu Leu Tyr Phe
            1365                1370                1375

Ile Ser Phe Leu Leu Ile Val Ser Phe Phe Val Leu Asn Met Phe Val
            1380                1385                1390
```

```
Gly Val Val Glu Asn Phe His Lys Cys Arg Gln His Gln Glu Ala
        1395                1400                1405
Glu Glu Ala Arg Arg Glu Glu Lys Arg Leu Arg Arg Leu Glu Lys
    1410                1415                1420
Lys Arg Arg Lys Ala Gln Arg Leu Pro Tyr Tyr Ala Thr Tyr Cys His
1425                1430                1435                1440
Thr Arg Leu Leu Ile His Ser Met Cys Thr Ser His Tyr Leu Asp Ile
            1445                1450                1455
Phe Ile Thr Phe Ile Ile Cys Leu Asn Val Val Thr Met Ser Leu Glu
            1460                1465                1470
His Tyr Asn Gln Pro Thr Ser Leu Glu Thr Ala Leu Lys Tyr Cys Asn
        1475                1480                1485
Tyr Met Phe Thr Thr Val Phe Val Leu Glu Ala Val Leu Lys Leu Val
    1490                1495                1500
Ala Phe Gly Leu Arg Arg Phe Phe Lys Asp Arg Trp Asn Gln Leu Asp
1505                1510                1515                1520
Leu Ala Ile Val Leu Leu Ser Val Met Gly Ile Thr Leu Glu Glu Ile
            1525                1530                1535
Glu Ile Asn Ala Ala Leu Pro Ile Asn Pro Thr Ile Ile Arg Ile Met
        1540                1545                1550
Arg Val Leu Arg Ile Ala Arg Val Leu Lys Leu Leu Lys Met Ala Thr
        1555                1560                1565
Gly Met Arg Ala Leu Leu Asp Thr Val Val Gln Ala Leu Pro Gln Val
    1570                1575                1580
Gly Asn Leu Gly Leu Leu Phe Met Leu Leu Phe Phe Ile Tyr Ala Ala
1585                1590                1595                1600
Leu Gly Val Glu Leu Phe Gly Lys Leu Val Cys Asn Asp Glu Asn Pro
            1605                1610                1615
Cys Glu Gly Met Ser Arg His Ala Thr Phe Glu Asn Phe Gly Met Ala
        1620                1625                1630
Phe Leu Thr Leu Phe Gln Val Ser Thr Gly Asp Asn Trp Asn Gly Ile
        1635                1640                1645
Met Lys Asp Thr Leu Arg Asp Cys Thr His Asp Glu Arg Ser Cys Leu
1650                1655                1660
Ser Ser Leu Gln Phe Val Ser Pro Leu Tyr Phe Val Ser Phe Val Leu
1665                1670                1675                1680
Thr Ala Gln Phe Val Leu Ile Asn Val Val Val Ala Val Leu Met Lys
            1685                1690                1695
His Leu Asp Asp Ser Asn Lys Glu Ala Gln Glu Asp Ala Glu Met Asp
        1700                1705                1710
Ala Glu Leu Glu Leu Glu Met Ala His Gly Leu Gly Pro Gly Pro Arg
    1715                1720                1725
Leu Pro Thr Gly Ser Pro Gly Ala Pro Gly Arg Gly Pro Gly Gly Ala
        1730                1735                1740
Gly Gly Gly Gly Asp Thr Glu Gly Gly Leu Cys Arg Arg Cys Tyr Ser
1745                1750                1755                1760
Pro Ala Gln Asp Ser Leu Glu Gly Glu Leu Thr Ile Ile Asp Asn Leu
            1765                1770                1775
Ser Gly Ser Ile Phe His His Tyr Ser Ser Pro Ala Gly Cys Lys Lys
            1780                1785                1790
Cys His His Asp Lys Gln Glu Val Gln Leu Ala Glu Thr Glu Ala Phe
        1795                1800                1805
Ser Leu Asn Ser Asp Arg Ser Ser Ser Ile Leu Leu Gly Asp Asp Leu
```

```
                    1810                1815                1820
Ser Leu Glu Asp Pro Thr Ala Cys Pro Pro Gly Arg Lys Asp Ser Lys
1825                1830                1835                1840

Gly Glu Leu Asp Pro Pro Glu Pro Met Arg Val Gly Asp Leu Gly Glu
            1845                1850                1855

Cys Phe Phe Pro Leu Ser Ser Thr Ala Val Ser Pro Asp Pro Glu Asn
            1860                1865                1870

Phe Leu Cys Glu Met Glu Glu Ile Pro Phe Asn Pro Val Arg Ser Trp
            1875                1880                1885

Leu Lys His Asp Ser Ser Gln Ala Pro Pro Ser Pro Phe Ser Pro Asp
            1890                1895                1900

Ala Ser Ser Pro Leu Leu Pro Met Pro Ala Glu Phe Phe His Pro Ala
1905                1910                1915                1920

Val Ser Ala Ser Gln Lys Gly Pro Glu Lys Gly Thr Gly Thr Gly Thr
            1925                1930                1935

Leu Pro Lys Ile Ala Leu Gln Gly Ser Trp Ala Ser Leu Arg Ser Pro
            1940                1945                1950

Arg Val Asn Cys Thr Leu Leu Arg Gln Ala Thr Gly Ser Asp Thr Ser
            1955                1960                1965

Leu Asp Ala Ser Pro Ser Ser Ser Ala Gly Ser Leu Gln Thr Thr Leu
            1970                1975                1980

Glu Asp Ser Leu Thr Leu Ser Asp Ser Pro Arg Arg Ala Leu Gly Pro
1985                1990                1995                2000

Pro Ala Pro Ala Pro Gly Pro Arg Ala Gly Leu Ser Pro Ala Ala Arg
            2005                2010                2015

Arg Arg Leu Ser Leu Arg Gly Arg Gly Leu Phe Ser Leu Arg Gly Leu
            2020                2025                2030

Arg Ala His Gln Arg Ser His Ser Ser Gly Ser Thr Ser Pro Gly
            2035                2040                2045

Cys Thr His His Asp Ser Met Asp Pro Ser Asp Glu Glu Arg Gly
            2050                2055                2060

Gly Ala Gly Gly Gly Ala Gly Ser Glu His Ser Glu Thr Leu Ser
2065                2070                2075                2080

Ser Leu Ser Leu Thr Ser Leu Phe Cys Pro Pro Pro Pro Pro Ala
            2085                2090                2095

Pro Gly Leu Thr Pro Ala Arg Lys Phe Ser Ser Thr Ser Ser Leu Ala
            2100                2105                2110

Ala Pro Gly Arg Pro His Ala Ala Leu Ala His Gly Leu Ala Arg
            2115                2120                2125

Ser Pro Ser Trp Ala Ala Asp Arg Ser Lys Asp Pro Pro Gly Arg Ala
            2130                2135                2140

Pro Leu Pro Met Gly Leu Gly Pro Leu Ala Pro Pro Gln Pro Leu
2145                2150                2155                2160

Pro Gly Glu Leu Glu Pro Gly Asp Ala Ala Ser Lys Arg Lys Arg
            2165                2170                2175

<210> SEQ ID NO 3
<211> LENGTH: 6855
<212> TYPE: DNA
<213> ORGANISM: Homo sapiens
<220> FEATURE:
<221> NAME/KEY: CDS
<222> LOCATION: (192)..(6755)

<400> SEQUENCE: 3
```

-continued

```
ctgggccctc agctgtttcg taatcctcat gcaagagtga gggtgagggg cctgtggggc      60
tcaggtgggg ctgtcagagc tgcatccgtc cacttattgg tggagaggca ggttggggag     120
catgtaccag gcctgtcccc accacgtgcc accctctctg tcttcccag ggctcccagc      180 tcagtgtgga c atg gct gag agc gcc tcc ccg ccc tcc tca tct gca gca     230
            Met Ala Glu Ser Ala Ser Pro Pro Ser Ser Ser Ala Ala
              1               5                  10 gcc cca gcc gct gag cca gga gtc acc acg gag cag ccc gga ccc cgg      278
Ala Pro Ala Ala Glu Pro Gly Val Thr Thr Glu Gln Pro Gly Pro Arg
     15                  20                  25 agc ccc cca tcc tcc ccg cca ggc ctg gag gag cct ctg gat gga gct      326
Ser Pro Pro Ser Ser Pro Pro Gly Leu Glu Glu Pro Leu Asp Gly Ala
 30                  35                  40                  45 gat cct cat gtc cca cac cca gac ctg gcg cct att gcc ttc ttc tgc      374
Asp Pro His Val Pro His Pro Asp Leu Ala Pro Ile Ala Phe Phe Cys
             50                  55                  60 ctg cga cag acc acc agc ccc cgg aac tgg tgc atc aag atg gtg tgc      422
Leu Arg Gln Thr Thr Ser Pro Arg Asn Trp Cys Ile Lys Met Val Cys
         65                  70                  75 aac ccg tgg ttt gaa tgt gtc agc atg ctg gtg atc ctg ctg aac tgc      470
Asn Pro Trp Phe Glu Cys Val Ser Met Leu Val Ile Leu Leu Asn Cys
     80                  85                  90 gtg aca ctt ggc atg tac cag ccg tgc gac gac atg gac tgc ctg tcc      518
Val Thr Leu Gly Met Tyr Gln Pro Cys Asp Asp Met Asp Cys Leu Ser
 95                 100                 105 gac cgc tgc aag atc ctg cag gtc ttt gat gac ttc atc ttt atc ttc      566
Asp Arg Cys Lys Ile Leu Gln Val Phe Asp Asp Phe Ile Phe Ile Phe
110                 115                 120                 125 ttt gcc atg gag atg gtg ctc aag atg gtg gcc ctg ggg att ttt ggc      614
Phe Ala Met Glu Met Val Leu Lys Met Val Ala Leu Gly Ile Phe Gly
                130                 135                 140 aag aag tgc tac ctc ggg gac aca tgg aac cgc ctg gat ttc ttc atc      662
Lys Lys Cys Tyr Leu Gly Asp Thr Trp Asn Arg Leu Asp Phe Phe Ile
            145                 150                 155 gtc atg gca ggg atg gtc gag tac tcc ctg gac ctt cag aac atc aac      710
Val Met Ala Gly Met Val Glu Tyr Ser Leu Asp Leu Gln Asn Ile Asn
        160                 165                 170 ctg tca gcc atc cgc acc gtg cgc gtc ctg agg ccc ctc aaa gcc atc      758
Leu Ser Ala Ile Arg Thr Val Arg Val Leu Arg Pro Leu Lys Ala Ile
    175                 180                 185 aac cgc gtg ccc agt atg cgg atc ctg gtg aac ctg ctc ctg gac aca      806
Asn Arg Val Pro Ser Met Arg Ile Leu Val Asn Leu Leu Leu Asp Thr
190                 195                 200                 205 ctg ccc atg ctg ggg aat gtc ctg ctc tgc ttc ttt gtc ttc ttc          854
Leu Pro Met Leu Gly Asn Val Leu Leu Leu Cys Phe Phe Val Phe Phe
                210                 215                 220 atc ttt ggc atc ata ggt gtg cag ctc tgg gcg ggc ctg ctg cgt aac      902
Ile Phe Gly Ile Ile Gly Val Gln Leu Trp Ala Gly Leu Leu Arg Asn
            225                 230                 235 cgc tgc ttc ctg gag gag aac ttc acc ata caa ggg gat gtg gcc ttg      950
Arg Cys Phe Leu Glu Glu Asn Phe Thr Ile Gln Gly Asp Val Ala Leu
        240                 245                 250 ccc cca tac tac cag ccg gag gag gat gat gag atg ccc ttc atc tgc      998
Pro Pro Tyr Tyr Gln Pro Glu Glu Asp Asp Glu Met Pro Phe Ile Cys
    255                 260                 265 tcc ctg tcg ggc gac aat ggg ata atg ggc tgc cat gag atc ccc ccg     1046
Ser Leu Ser Gly Asp Asn Gly Ile Met Gly Cys His Glu Ile Pro Pro
270                 275                 280                 285 ctc aag gag cag ggc cgt gag tgc tgc ctg tcc aag gac gac gtc tac     1094
```

```
                    Leu Lys Glu Gln Gly Arg Glu Cys Cys Leu Ser Lys Asp Asp Val Tyr
                                    290                 295                 300 gac ttt ggg gcg ggg cgc cag gac ctc aat gcc agc ggc ctc tgt gtc            1142
Asp Phe Gly Ala Gly Arg Gln Asp Leu Asn Ala Ser Gly Leu Cys Val
                305                 310                 315 aac tgg aac cgt tac tac aat gtg tgc cgc acg ggc agc gcc aac ccc            1190
Asn Trp Asn Arg Tyr Tyr Asn Val Cys Arg Thr Gly Ser Ala Asn Pro
            320                 325                 330 cac aag ggt gcc atc aac ttt gac aac atc ggt tat gct tgg att gtc            1238
His Lys Gly Ala Ile Asn Phe Asp Asn Ile Gly Tyr Ala Trp Ile Val
        335                 340                 345 atc ttc cag gtg atc act ctg gaa ggc tgg gtg gag atc atg tac tac            1286
Ile Phe Gln Val Ile Thr Leu Glu Gly Trp Val Glu Ile Met Tyr Tyr
350                 355                 360                 365 gtg atg gat gct cac tcc ttc tac aac ttc atc tac ttc atc ctg ctt            1334
Val Met Asp Ala His Ser Phe Tyr Asn Phe Ile Tyr Phe Ile Leu Leu
                370                 375                 380 atc ata gtg ggc tcc ttc ttc atg atc aac ctg tgc ctc gtt gtc ata            1382
Ile Ile Val Gly Ser Phe Phe Met Ile Asn Leu Cys Leu Val Val Ile
            385                 390                 395 gcg acc cag ttc tcg gag acc aag caa cgg gag cac cgg ctg atg ctg            1430
Ala Thr Gln Phe Ser Glu Thr Lys Gln Arg Glu His Arg Leu Met Leu
        400                 405                 410 gag cag cgg cag cgc tac ctg tcc tcc agc acg gtg gcc agc tac gcc            1478
Glu Gln Arg Gln Arg Tyr Leu Ser Ser Ser Thr Val Ala Ser Tyr Ala
415                 420                 425 gag cct ggc gac tgc tac gag gag atc ttc cag tat gtc tgc cac atc            1526
Glu Pro Gly Asp Cys Tyr Glu Glu Ile Phe Gln Tyr Val Cys His Ile
                430                 435                 440                 445 ctg cgc aag gcc aag cgc cgc gcc ctg ggc ctc tac cag gcc ctg cag            1574
Leu Arg Lys Ala Lys Arg Arg Ala Leu Gly Leu Tyr Gln Ala Leu Gln
            450                 455                 460 agc cgg cgc cag gcc ctg ggc ccg gag gcc ccg gcc ccc gcc aaa cct            1622
Ser Arg Arg Gln Ala Leu Gly Pro Glu Ala Pro Ala Pro Ala Lys Pro
        465                 470                 475 ggg ccc cac gcc aag gag ccc cgg cac tac cag ctg tgc ccg caa cat            1670
Gly Pro His Ala Lys Glu Pro Arg His Tyr Gln Leu Cys Pro Gln His
    480                 485                 490 agc ccc ctg gat gcg acg ccc cac acc ctg gtg cag ccc atc ccc gcc            1718
Ser Pro Leu Asp Ala Thr Pro His Thr Leu Val Gln Pro Ile Pro Ala
495                 500                 505 acg ctg gct tcc gat ccc gcc agc tgc cct tgc tgc cag cat gag gac            1766
Thr Leu Ala Ser Asp Pro Ala Ser Cys Pro Cys Cys Gln His Glu Asp
510                 515                 520                 525 ggc cgg cgg ccc tcg ggc ctg ggc agc acc gac tcg ggc cag gag ggc            1814
Gly Arg Arg Pro Ser Gly Leu Gly Ser Thr Asp Ser Gly Gln Glu Gly
                530                 535                 540 tcg ggc tcc ggg agc tcc gct ggt ggc gag gac gag gcg gat ggg gac            1862
Ser Gly Ser Gly Ser Ser Ala Gly Gly Glu Asp Glu Ala Asp Gly Asp
            545                 550                 555 ggg gcc cgg agc agc gag gac gga gcc tcc tca gaa ctg ggg aag gag            1910
Gly Ala Arg Ser Ser Glu Asp Gly Ala Ser Ser Glu Leu Gly Lys Glu
        560                 565                 570 gag gag gag gag gag cag gcg gat ggg gcg gtc tgg ctg tgc ggg gat            1958
Glu Glu Glu Glu Glu Gln Ala Asp Gly Ala Val Trp Leu Cys Gly Asp
    575                 580                 585 gtg tgg cgg gag acg cga gcc aag ctg cgc ggc atc gtg gac agc aag            2006
Val Trp Arg Glu Thr Arg Ala Lys Leu Arg Gly Ile Val Asp Ser Lys
590                 595                 600                 605
```

-continued

| | | |
|---|---|---|
| tac ttc aac cgg ggc atc atg atg gcc atc ctg gtc aac acc gtc agc<br>Tyr Phe Asn Arg Gly Ile Met Met Ala Ile Leu Val Asn Thr Val Ser<br>610                        615                      620 | | 2054 |
| atg ggc atc gag cac cac gag cag ccg gag gag ctg acc aac atc ctg<br>Met Gly Ile Glu His His Glu Gln Pro Glu Glu Leu Thr Asn Ile Leu<br>625                       630                      635 | | 2102 |
| gag atc tgc aat gtg gtc ttc acc agc atg ttt gcc ctg gag atg atc<br>Glu Ile Cys Asn Val Val Phe Thr Ser Met Phe Ala Leu Glu Met Ile<br>640                        645                      650 | | 2150 |
| ctg aag ctg gct gca ttt ggg ctc ttc gac tac ctg cgt aac ccc tac<br>Leu Lys Leu Ala Ala Phe Gly Leu Phe Asp Tyr Leu Arg Asn Pro Tyr<br>655                       660                      665 | | 2198 |
| aac atc ttc gac agc atc att gtc atc atc agc atc tgg gag atc gtg<br>Asn Ile Phe Asp Ser Ile Ile Val Ile Ile Ser Ile Trp Glu Ile Val<br>670                      675                      680                   685 | | 2246 |
| ggg cag gcg gac ggt ggg ctg tcg gtg ctg cgg acc ttc cgg ctg ctg<br>Gly Gln Ala Asp Gly Gly Leu Ser Val Leu Arg Thr Phe Arg Leu Leu<br>                     690                      695                      700 | | 2294 |
| cgc gtg ctg aaa ctg gtg cgc ttc atg cct gcc ctg cgg cgc cag ctc<br>Arg Val Leu Lys Leu Val Arg Phe Met Pro Ala Leu Arg Arg Gln Leu<br>               705                      710                      715 | | 2342 |
| gtg gtg ctc atg aag acc atg gac aac gtg gcc acc ttc tgc atg ctg<br>Val Val Leu Met Lys Thr Met Asp Asn Val Ala Thr Phe Cys Met Leu<br>        720                      725                      730 | | 2390 |
| ctc atg ctc ttc atc ttc atc ttc agc atc ctt ggg atg cat att ttt<br>Leu Met Leu Phe Ile Phe Ile Phe Ser Ile Leu Gly Met His Ile Phe<br>735                      740                      745 | | 2438 |
| ggc tgc aag ttc agc ctc cgc acg gac act gga gac acg gtg ccc gac<br>Gly Cys Lys Phe Ser Leu Arg Thr Asp Thr Gly Asp Thr Val Pro Asp<br>750                      755                      760                   765 | | 2486 |
| agg aag aac ttc gac tcc ctg ctg tgg gcc atc gtc act gtg ttc cag<br>Arg Lys Asn Phe Asp Ser Leu Leu Trp Ala Ile Val Thr Val Phe Gln<br>                     770                      775                      780 | | 2534 |
| atc ctc acc cag gag gac tgg aac gtc gtt ctc tac aat ggc atg gcc<br>Ile Leu Thr Gln Glu Asp Trp Asn Val Val Leu Tyr Asn Gly Met Ala<br>               785                      790                      795 | | 2582 |
| tcc act tct ccc tgg gcc tcc ctc tac ttt gtc gcc ctc atg acc ttc<br>Ser Thr Ser Pro Trp Ala Ser Leu Tyr Phe Val Ala Leu Met Thr Phe<br>        800                      805                      810 | | 2630 |
| ggc aac tat gtg ctc ttc aac ctg ctg gtg gcc atc ctg gtg gag ggc<br>Gly Asn Tyr Val Leu Phe Asn Leu Leu Val Ala Ile Leu Val Glu Gly<br>815                      820                      825 | | 2678 |
| ttc cag gcg gag ggt gac gcc aat cgc tcc tac tcg gac gag gac cag<br>Phe Gln Ala Glu Gly Asp Ala Asn Arg Ser Tyr Ser Asp Glu Asp Gln<br>830                      835                      840                   845 | | 2726 |
| agc tca tcc aac ata gaa gag ttt gat aag ctc cag gaa ggc ctg gac<br>Ser Ser Ser Asn Ile Glu Glu Phe Asp Lys Leu Gln Glu Gly Leu Asp<br>                     850                      855                   860 | | 2774 |
| agc agc gga gat ccc aag ctc tgc cca atc ccc atg acc ccc aat ggg<br>Ser Ser Gly Asp Pro Lys Leu Cys Pro Ile Pro Met Thr Pro Asn Gly<br>               865                      870                      875 | | 2822 |
| cac ctg gac ccc agt ctc cca ctg ggt ggg cac cta ggt cct gct ggg<br>His Leu Asp Pro Ser Leu Pro Leu Gly Gly His Leu Gly Pro Ala Gly<br>        880                      885                      890 | | 2870 |
| gct gcg gga cct gcc ccc cga ctc tca ctg cag ccg gac ccc atg ctg<br>Ala Ala Gly Pro Ala Pro Arg Leu Ser Leu Gln Pro Asp Pro Met Leu<br>895                      900                      905 | | 2918 |
| gtg gcc ctg ggc tcc cga aag agc agt gtc atg tct cta ggg agg atg<br>Val Ala Leu Gly Ser Arg Lys Ser Ser Val Met Ser Leu Gly Arg Met<br>910                      915                      920                   925 | | 2966 |

```
agc tat gac cag cgc tcc ctg tcc agc tcc cgg agc tcc tac tac ggg        3014
Ser Tyr Asp Gln Arg Ser Leu Ser Ser Ser Arg Ser Ser Tyr Tyr Gly
            930                 935                 940 cca tgg ggc cgc agc gcg gcc tgg gcc agc cgt cgc tcc agc tgg aac        3062
Pro Trp Gly Arg Ser Ala Ala Trp Ala Ser Arg Arg Ser Ser Trp Asn
        945                 950                 955 agc ctc aag cac aag ccg ccg tcg gcg gag cat gag tcc ctg ctc tct        3110
Ser Leu Lys His Lys Pro Pro Ser Ala Glu His Glu Ser Leu Leu Ser
    960                 965                 970 gcg gag cgc ggc ggc ggc gcc cgg gtc tgc gag gtt gcc gcg gac gag        3158
Ala Glu Arg Gly Gly Gly Ala Arg Val Cys Glu Val Ala Ala Asp Glu
975                 980                 985 ggg ccg ccg cgg gcc gca ccc ctg cac acc cca cac gcc cac cac att        3206
Gly Pro Pro Arg Ala Ala Pro Leu His Thr Pro His Ala His His Ile
990                 995                 1000                1005 cat cac ggg ccc cat ctg gcg cac cgc cac cgc cac cac cgc cgg acg        3254
His His Gly Pro His Leu Ala His Arg His Arg His His Arg Arg Thr
                1010                1015                1020 ctg tcc ctc gac aac agg gac tcg gtg gac ctg gcc gag ctg gtg ccc        3302
Leu Ser Leu Asp Asn Arg Asp Ser Val Asp Leu Ala Glu Leu Val Pro
            1025                1030                1035 gcg gtg ggc gcc cac ccc cgg gcc gcc tgg agg gcg gca ggc ccg gcc        3350
Ala Val Gly Ala His Pro Arg Ala Ala Trp Arg Ala Ala Gly Pro Ala
        1040                1045                1050 ccc ggg cat gag gac tgc aat ggc agg atg ccc agc atc gcc aaa gac        3398
Pro Gly His Glu Asp Cys Asn Gly Arg Met Pro Ser Ile Ala Lys Asp
    1055                1060                1065 gtc ttc acc aag atg ggc gac cgc ggg gat cgc ggg gag gat gag gag        3446
Val Phe Thr Lys Met Gly Asp Arg Gly Asp Arg Gly Glu Asp Glu Glu
1070                1075                1080                1085 gaa atc gac tac acc ctg tgc ttc cgc gtc cgc aag atg atc gac gtc        3494
Glu Ile Asp Tyr Thr Leu Cys Phe Arg Val Arg Lys Met Ile Asp Val
                1090                1095                1100 tat aag ccc gac tgg tgc gag gtc cgc gaa gac tgg tct gtc tac ctc        3542
Tyr Lys Pro Asp Trp Cys Glu Val Arg Glu Asp Trp Ser Val Tyr Leu
            1105                1110                1115 ttc tct ccc gag aac agg ttc cgg gtc ctg tgt cag acc att att gcc        3590
Phe Ser Pro Glu Asn Arg Phe Arg Val Leu Cys Gln Thr Ile Ile Ala
        1120                1125                1130 cac aaa ctc ttc gac tac gtc gtc ctg gcc ttc atc ttt ctc aac tgc        3638
His Lys Leu Phe Asp Tyr Val Val Leu Ala Phe Ile Phe Leu Asn Cys
    1135                1140                1145 atc acc atc gcc ctg gag cgg cct cag atc gag gcc ggc agc acc gaa        3686
Ile Thr Ile Ala Leu Glu Arg Pro Gln Ile Glu Ala Gly Ser Thr Glu
1150                1155                1160                1165 cgc atc ttt ctc acc gtg tcc aac tac atc ttc acg gcc atc ttc gtg        3734
Arg Ile Phe Leu Thr Val Ser Asn Tyr Ile Phe Thr Ala Ile Phe Val
                1170                1175                1180 ggc gag atg aca ttg aag gta gtc tcg ctg ggc ctg tac ttc ggc gag        3782
Gly Glu Met Thr Leu Lys Val Val Ser Leu Gly Leu Tyr Phe Gly Glu
            1185                1190                1195 cag gcg tac cta cgc agc agc tgg aac gtg ctg gat ggc ttt ctt gtc        3830
Gln Ala Tyr Leu Arg Ser Ser Trp Asn Val Leu Asp Gly Phe Leu Val
        1200                1205                1210 ttc gtg tcc atc atc gac atc gtg gtg tcc ctg gcc tca gcc ggg gga        3878
Phe Val Ser Ile Ile Asp Ile Val Val Ser Leu Ala Ser Ala Gly Gly
    1215                1220                1225 gcc aag atc ttg ggg gtc ctc cga gtc ttg cgg ctc ctg cgc acc cta        3926
Ala Lys Ile Leu Gly Val Leu Arg Val Leu Arg Leu Leu Arg Thr Leu
```

-continued

```
          1230                1235                1240                1245
cgc ccc ctg cgt gtc atc agc cgg gcg ccg ggc ctg aag ctg gtg gtg    3974
Arg Pro Leu Arg Val Ile Ser Arg Ala Pro Gly Leu Lys Leu Val Val
                1250                1255                1260 gag aca ctc atc tcc tcc ctc aag ccc atc ggc aac atc gtg ctc atc    4022
Glu Thr Leu Ile Ser Ser Leu Lys Pro Ile Gly Asn Ile Val Leu Ile
                1265                1270                1275 tgc tgt gcc ttc ttc atc atc ttt ggc atc ctg gga gtg cag ctc ttc    4070
Cys Cys Ala Phe Phe Ile Ile Phe Gly Ile Leu Gly Val Gln Leu Phe
                1280                1285                1290 aag ggc aag ttc tac cac tgt ctg ggc gtg gac acc cgc aac atc acc    4118
Lys Gly Lys Phe Tyr His Cys Leu Gly Val Asp Thr Arg Asn Ile Thr
                1295                1300                1305 aac cgc tcg gac tgc atg gcc gcc aac tac cgc tgg gtc cat cac aaa    4166
Asn Arg Ser Asp Cys Met Ala Ala Asn Tyr Arg Trp Val His His Lys
1310                1315                1320                1325 tac aac ttc gac aac ctg ggc cag gct ctg atg tcc ctc ttt gtc ctg    4214
Tyr Asn Phe Asp Asn Leu Gly Gln Ala Leu Met Ser Leu Phe Val Leu
                1330                1335                1340 gca tcc aag gat ggt tgg gtg aac atc atg tac aat gga ctg gat gct    4262
Ala Ser Lys Asp Gly Trp Val Asn Ile Met Tyr Asn Gly Leu Asp Ala
                1345                1350                1355 gtt gct gtg gac cag cag cct gtg acc aac cac aac ccc tgg atg ctg    4310
Val Ala Val Asp Gln Gln Pro Val Thr Asn His Asn Pro Trp Met Leu
                1360                1365                1370 ctg tac ttc atc tcc ttc ctc atc gtc agc ttc ttt gtg ctc aac       4358
Leu Tyr Phe Ile Ser Phe Leu Leu Ile Val Ser Phe Phe Val Leu Asn
                1375                1380                1385 atg ttt gtg ggt gtc gtg gtg gag aac ttc cac aag tgc cgg cag cac    4406
Met Phe Val Gly Val Val Val Glu Asn Phe His Lys Cys Arg Gln His
1390                1395                1400                1405 cag gag gct gaa gag gca cgg cgg cgt gag gag aag cgg ctg cgg cgc    4454
Gln Glu Ala Glu Glu Ala Arg Arg Arg Glu Glu Lys Arg Leu Arg Arg
                1410                1415                1420 ctg gag aag aag cgc cgg aag gcc cag cgg ctg ccc tac tat gcc acc    4502
Leu Glu Lys Lys Arg Arg Lys Ala Gln Arg Leu Pro Tyr Tyr Ala Thr
                1425                1430                1435 tat tgt cac acc cgg ctg ctc atc cac tcc atg tgc acc agc cac tac    4550
Tyr Cys His Thr Arg Leu Leu Ile His Ser Met Cys Thr Ser His Tyr
                1440                1445                1450 ctg gac atc ttc atc acc ttc atc atc tgc ctc aac gtg gtc acc atg    4598
Leu Asp Ile Phe Ile Thr Phe Ile Ile Cys Leu Asn Val Val Thr Met
                1455                1460                1465 tcc ctg gag cac tac aat cag ccc acg tcc ctg gag aca gcc ctc aag    4646
Ser Leu Glu His Tyr Asn Gln Pro Thr Ser Leu Glu Thr Ala Leu Lys
1470                1475                1480                1485 tac tgc aac tat atg ttc acc act gtc ttt gtg ctg gag gct gtg ctg    4694
Tyr Cys Asn Tyr Met Phe Thr Thr Val Phe Val Leu Glu Ala Val Leu
                1490                1495                1500 aag ctg gtg gca ttt ggt ctg agg cgc ttc ttc aag gac cga tgg aac    4742
Lys Leu Val Ala Phe Gly Leu Arg Arg Phe Phe Lys Asp Arg Trp Asn
                1505                1510                1515 cag ctg gac ctg gcc att gtg cta ctg tca gtc atg ggc atc acc ctg    4790
Gln Leu Asp Leu Ala Ile Val Leu Leu Ser Val Met Gly Ile Thr Leu
                1520                1525                1530 gag gag atc gag atc aat gcg gcc ctg ccc atc aat ccc acc atc atc    4838
Glu Glu Ile Glu Ile Asn Ala Ala Leu Pro Ile Asn Pro Thr Ile Ile
                1535                1540                1545 cgc atc atg agg gtt ctg cgc att gcc cga gtg ctg aag ctg ttg aag    4886
```

-continued

```
Arg Ile Met Arg Val Leu Arg Ile Ala Arg Val Leu Lys Leu Leu Lys
1550                1555                1560                1565 atg gcc aca gga atg cgg gcc ctg ctg gac acg gtg gtg caa gct ttg         4934
Met Ala Thr Gly Met Arg Ala Leu Leu Asp Thr Val Val Gln Ala Leu
                1570                1575                1580 ccc cag gtg ggc aac ctg ggc ctc ctc ttc atg ctg ctc ttc ttc atc         4982
Pro Gln Val Gly Asn Leu Gly Leu Leu Phe Met Leu Leu Phe Phe Ile
                1585                1590                1595 tat gct gct ctc ggg gtg gag ctc ttt ggg aag ctg gtc tgc aac gac         5030
Tyr Ala Ala Leu Gly Val Glu Leu Phe Gly Lys Leu Val Cys Asn Asp
                1600                1605                1610 gag aac ccg tgc gag ggc atg agc cgg cat gcc acc ttc gag aac ttc         5078
Glu Asn Pro Cys Glu Gly Met Ser Arg His Ala Thr Phe Glu Asn Phe
                1615                1620                1625 ggc atg gcc ttc ctc aca ctc ttc cag gtc tcc acg ggt gac aac tgg         5126
Gly Met Ala Phe Leu Thr Leu Phe Gln Val Ser Thr Gly Asp Asn Trp
1630                1635                1640                1645 aac ggg atc atg aag gac acg ctg cgg gac tgc acc cac gac gag cgc         5174
Asn Gly Ile Met Lys Asp Thr Leu Arg Asp Cys Thr His Asp Glu Arg
                1650                1655                1660 agc tgc ctg agc agc ctg cag ttt gtg tcg ccg ctg tac ttc gtg agc         5222
Ser Cys Leu Ser Ser Leu Gln Phe Val Ser Pro Leu Tyr Phe Val Ser
                1665                1670                1675 ttc gtg ctc acc gcg cag ttc gtg ctc atc aac gtg gtg gtg gct gtg         5270
Phe Val Leu Thr Ala Gln Phe Val Leu Ile Asn Val Val Val Ala Val
                1680                1685                1690 ctc atg aag cac ctg gac gac agc aac aag gag gcg cag gag gac gcc         5318
Leu Met Lys His Leu Asp Asp Ser Asn Lys Glu Ala Gln Glu Asp Ala
                1695                1700                1705 gag atg gat gcc gag ctc gag ctg gag atg gcc cat ggc ctg ggc cct         5366
Glu Met Asp Ala Glu Leu Glu Leu Glu Met Ala His Gly Leu Gly Pro
1710                1715                1720                1725 ggc ccg agg ctg cct acc ggc tcc ccg ggc gcc cct ggc cga ggg ccg         5414
Gly Pro Arg Leu Pro Thr Gly Ser Pro Gly Ala Pro Gly Arg Gly Pro
                1730                1735                1740 gga ggg gcg ggc ggc ggg ggc gac acc gag ggc ggc ttg tgc cgg cgc         5462
Gly Gly Ala Gly Gly Gly Gly Asp Thr Glu Gly Gly Leu Cys Arg Arg
                1745                1750                1755 tgc tac tcg cct gcc cag gag aac ctg tgg ctg gac agc gtc tct tta         5510
Cys Tyr Ser Pro Ala Gln Glu Asn Leu Trp Leu Asp Ser Val Ser Leu
                1760                1765                1770 atc atc aag gac tcc ttg gag ggg gag ctg acc atc atc gac aac ctg         5558
Ile Ile Lys Asp Ser Leu Glu Gly Glu Leu Thr Ile Ile Asp Asn Leu
1775                1780                1785 tcg ggc tcc atc ttc cac cac tac tcc tcg cct gcc ggc tgc aag aag         5606
Ser Gly Ser Ile Phe His His Tyr Ser Ser Pro Ala Gly Cys Lys Lys
1790                1795                1800                1805 tgt cac cac gac aag caa gag gtg cag ctg gct gag acg gag gcc ttc         5654
Cys His His Asp Lys Gln Glu Val Gln Leu Ala Glu Thr Glu Ala Phe
                1810                1815                1820 tcc ctg aac tca gac agg tcc tcg tcc atc ctg ctg ggt gac gac ctg         5702
Ser Leu Asn Ser Asp Arg Ser Ser Ser Ile Leu Leu Gly Asp Asp Leu
                1825                1830                1835 agt ctc gag gac ccc aca gcc tgc cca cct ggc cgc aaa gac agc aag         5750
Ser Leu Glu Asp Pro Thr Ala Cys Pro Pro Gly Arg Lys Asp Ser Lys
                1840                1845                1850 ggt gag ctg gac cca cct gag ccc atg cgt gtg gga gac ctg ggc gaa         5798
Gly Glu Leu Asp Pro Pro Glu Pro Met Arg Val Gly Asp Leu Gly Glu
1855                1860                1865
```

-continued

| | |
|---|---|
| tgc ttc ttc ccc ttg tcc tct acg gcc gtc tcg ccg gat cca gag aac<br>Cys Phe Phe Pro Leu Ser Ser Thr Ala Val Ser Pro Asp Pro Glu Asn<br>1870                  1875                  1880                  1885 | 5846 |
| ttc ctg tgt gag atg gag gag atc cca ttc aac cct gtc cgg tcc tgg<br>Phe Leu Cys Glu Met Glu Glu Ile Pro Phe Asn Pro Val Arg Ser Trp<br>            1890                  1895                  1900 | 5894 |
| ctg aaa cat gac agc agt caa gca ccc cca agt ccc ttc tcc ccg gat<br>Leu Lys His Asp Ser Ser Gln Ala Pro Pro Ser Pro Phe Ser Pro Asp<br>          1905                  1910                  1915 | 5942 |
| gcc tcc agc cct ctc ctg ccc atg cca gcc gag ttc ttc cac cct gca<br>Ala Ser Ser Pro Leu Leu Pro Met Pro Ala Glu Phe Phe His Pro Ala<br>1920                  1925                  1930 | 5990 |
| gtg tct gcc agc cag aaa ggc cca gaa aag ggc act ggc act gga acc<br>Val Ser Ala Ser Gln Lys Gly Pro Glu Lys Gly Thr Gly Thr Gly Thr<br>          1935                  1940                  1945 | 6038 |
| ctc ccc aag att gcg ctg cag ggc tcc tgg gca tct ctg cgg tca cca<br>Leu Pro Lys Ile Ala Leu Gln Gly Ser Trp Ala Ser Leu Arg Ser Pro<br>1950                  1955                  1960                  1965 | 6086 |
| agg gtc aac tgt acc ctc ctc cgg cag gcc acc ggg agc gac acg tcg<br>Arg Val Asn Cys Thr Leu Leu Arg Gln Ala Thr Gly Ser Asp Thr Ser<br>            1970                  1975                  1980 | 6134 |
| ctg gac gcc agc ccc agc agc tcc gcg ggc agc ctg cag acc acg ctc<br>Leu Asp Ala Ser Pro Ser Ser Ser Ala Gly Ser Leu Gln Thr Thr Leu<br>          1985                  1990                  1995 | 6182 |
| gag gac agc ctg acc ctg agc gac agc ccc cgg cgt gcc ctg ggg ccg<br>Glu Asp Ser Leu Thr Leu Ser Asp Ser Pro Arg Arg Ala Leu Gly Pro<br>2000                  2005                  2010 | 6230 |
| ccc gcg cct gct cca gga ccc cgg gcc ggc ctg tcc ccc gcc gct cgc<br>Pro Ala Pro Ala Pro Gly Pro Arg Ala Gly Leu Ser Pro Ala Ala Arg<br>          2015                  2020                  2025 | 6278 |
| cgc cgc ctg agc ctg cgc ggc cgg ggc ctc ttc agc ctg cgg ggg ctg<br>Arg Arg Leu Ser Leu Arg Gly Arg Gly Leu Phe Ser Leu Arg Gly Leu<br>2030                  2035                  2040                  2045 | 6326 |
| cgg gcg cat cag cgc agc cac agc agc ggg ggc tcc acc agc ccg ggc<br>Arg Ala His Gln Arg Ser His Ser Ser Gly Gly Ser Thr Ser Pro Gly<br>            2050                  2055                  2060 | 6374 |
| tgc acc cac cac gac tcc atg gac ccc tcg gac gag gag ggc cgc ggt<br>Cys Thr His His Asp Ser Met Asp Pro Ser Asp Glu Glu Gly Arg Gly<br>          2065                  2070                  2075 | 6422 |
| ggc gcg ggc ggc ggg ggc gcg ggc agc gag cac tcg gag acc ctc agc<br>Gly Ala Gly Gly Gly Gly Ala Gly Ser Glu His Ser Glu Thr Leu Ser<br>2080                  2085                  2090 | 6470 |
| agc ctc tcg ctc acc tcc ctc ttc tgc ccg ccg ccc ccg cca gcc<br>Ser Leu Ser Leu Thr Ser Leu Phe Cys Pro Pro Pro Pro Pro Ala<br>          2095                  2100                  2105 | 6518 |
| ccc ggc ctc acg ccc gcc agg aag ttc agc agc acc agc agc ctg gcc<br>Pro Gly Leu Thr Pro Ala Arg Lys Phe Ser Ser Thr Ser Ser Leu Ala<br>2110                  2115                  2120                  2125 | 6566 |
| gcc ccc ggc cgc ccc cac gcc gcc gcc ctg gcc cac ggc ctg gcc cgg<br>Ala Pro Gly Arg Pro His Ala Ala Ala Leu Ala His Gly Leu Ala Arg<br>            2130                  2135                  2140 | 6614 |
| agc ccc tcg tgg gcc gcg gac cgc agc aag gac ccc ccc ggc cgg gca<br>Ser Pro Ser Trp Ala Ala Asp Arg Ser Lys Asp Pro Pro Gly Arg Ala<br>          2145                  2150                  2155 | 6662 |
| ccg ctg ccc atg ggc ctg ggc ccc ttg gcg ccc ccg ccg caa ccg ctc<br>Pro Leu Pro Met Gly Leu Gly Pro Leu Ala Pro Pro Pro Gln Pro Leu<br>2160                  2165                  2170 | 6710 |
| ccc gga gag ctg gag ccg gga gac gcc gcc agc aag agg aag aga<br>Pro Gly Glu Leu Glu Pro Gly Asp Ala Ala Ser Lys Arg Lys Arg<br>          2175                  2180                  2185 | 6755 |

```
tgagggtcgc agggggccccc ggccgcccac cgcccgcccc gtctcacctt ctttacctca    6815
ggagccagga gcagacagca atacttcgtc cacacctggg                           6855
```

<210> SEQ ID NO 4
<211> LENGTH: 2188
<212> TYPE: PRT
<213> ORGANISM: Homo sapiens

<400> SEQUENCE: 4

```
Met Ala Glu Ser Ala Ser Pro Ser Ser Ala Ala Pro Ala
 1               5                  10              15

Ala Glu Pro Gly Val Thr Thr Glu Gln Pro Gly Pro Arg Ser Pro Pro
            20                  25                  30

Ser Ser Pro Pro Gly Leu Glu Glu Pro Leu Asp Gly Ala Asp Pro His
        35                  40                  45

Val Pro His Pro Asp Leu Ala Pro Ile Ala Phe Phe Cys Leu Arg Gln
    50                  55                  60

Thr Thr Ser Pro Arg Asn Trp Cys Ile Lys Met Val Cys Asn Pro Trp
65                  70                  75                  80

Phe Glu Cys Val Ser Met Leu Val Ile Leu Leu Asn Cys Val Thr Leu
                85                  90                  95

Gly Met Tyr Gln Pro Cys Asp Asp Met Asp Cys Leu Ser Asp Arg Cys
            100                 105                 110

Lys Ile Leu Gln Val Phe Asp Asp Phe Ile Phe Ile Phe Phe Ala Met
        115                 120                 125

Glu Met Val Leu Lys Met Val Ala Leu Gly Ile Phe Gly Lys Lys Cys
    130                 135                 140

Tyr Leu Gly Asp Thr Trp Asn Arg Leu Asp Phe Phe Ile Val Met Ala
145                 150                 155                 160

Gly Met Val Glu Tyr Ser Leu Asp Leu Gln Asn Ile Asn Leu Ser Ala
                165                 170                 175

Ile Arg Thr Val Arg Val Leu Arg Pro Leu Lys Ala Ile Asn Arg Val
            180                 185                 190

Pro Ser Met Arg Ile Leu Val Asn Leu Leu Leu Asp Thr Leu Pro Met
        195                 200                 205

Leu Gly Asn Val Leu Leu Leu Cys Phe Phe Val Phe Phe Ile Phe Gly
    210                 215                 220

Ile Ile Gly Val Gln Leu Trp Ala Gly Leu Leu Arg Asn Arg Cys Phe
225                 230                 235                 240

Leu Glu Glu Asn Phe Thr Ile Gln Gly Asp Val Ala Leu Pro Pro Tyr
                245                 250                 255

Tyr Gln Pro Glu Glu Asp Asp Glu Met Pro Phe Ile Cys Ser Leu Ser
            260                 265                 270

Gly Asp Asn Gly Ile Met Gly Cys His Glu Ile Pro Pro Leu Lys Glu
        275                 280                 285

Gln Gly Arg Glu Cys Cys Leu Ser Lys Asp Asp Val Tyr Asp Phe Gly
    290                 295                 300

Ala Gly Arg Gln Asp Leu Asn Ala Ser Gly Leu Cys Val Asn Trp Asn
305                 310                 315                 320

Arg Tyr Tyr Asn Val Cys Arg Thr Gly Ser Ala Asn Pro His Lys Gly
                325                 330                 335

Ala Ile Asn Phe Asp Asn Ile Gly Tyr Ala Trp Ile Val Ile Phe Gln
            340                 345                 350
```

```
Val Ile Thr Leu Glu Gly Trp Val Glu Ile Met Tyr Tyr Val Met Asp
        355                 360                 365

Ala His Ser Phe Tyr Asn Phe Ile Tyr Phe Ile Leu Leu Ile Ile Val
        370                 375                 380

Gly Ser Phe Phe Met Ile Asn Leu Cys Leu Val Val Ile Ala Thr Gln
385                 390                 395                 400

Phe Ser Glu Thr Lys Gln Arg Glu His Arg Leu Met Leu Glu Gln Arg
                405                 410                 415

Gln Arg Tyr Leu Ser Ser Ser Thr Val Ala Ser Tyr Ala Glu Pro Gly
            420                 425                 430

Asp Cys Tyr Glu Glu Ile Phe Gln Tyr Val Cys His Ile Leu Arg Lys
            435                 440                 445

Ala Lys Arg Arg Ala Leu Gly Leu Tyr Gln Ala Leu Gln Ser Arg Arg
450                 455                 460

Gln Ala Leu Gly Pro Glu Ala Pro Ala Lys Pro Gly Pro His
465                 470                 475                 480

Ala Lys Glu Pro Arg His Tyr Gln Leu Cys Pro Gln His Ser Pro Leu
                485                 490                 495

Asp Ala Thr Pro His Thr Leu Val Gln Pro Ile Pro Ala Thr Leu Ala
                500                 505                 510

Ser Asp Pro Ala Ser Cys Pro Cys Gln His Glu Asp Gly Arg Arg
        515                 520                 525

Pro Ser Gly Leu Gly Ser Thr Asp Ser Gly Gln Glu Gly Ser Gly Ser
        530                 535                 540

Gly Ser Ser Ala Gly Gly Glu Asp Glu Ala Asp Gly Asp Gly Ala Arg
545                 550                 555                 560

Ser Ser Glu Asp Gly Ala Ser Ser Glu Leu Gly Lys Glu Glu Glu Glu
                565                 570                 575

Glu Glu Gln Ala Asp Gly Ala Val Trp Leu Cys Gly Asp Val Trp Arg
            580                 585                 590

Glu Thr Arg Ala Lys Leu Arg Gly Ile Val Asp Ser Lys Tyr Phe Asn
            595                 600                 605

Arg Gly Ile Met Met Ala Ile Leu Val Asn Thr Val Ser Met Gly Ile
610                 615                 620

Glu His His Glu Gln Pro Glu Glu Leu Thr Asn Ile Leu Glu Ile Cys
625                 630                 635                 640

Asn Val Val Phe Thr Ser Met Phe Ala Leu Glu Met Ile Leu Lys Leu
                645                 650                 655

Ala Ala Phe Gly Leu Phe Asp Tyr Leu Arg Asn Pro Tyr Asn Ile Phe
                660                 665                 670

Asp Ser Ile Ile Val Ile Ile Ser Ile Trp Glu Ile Val Gly Gln Ala
        675                 680                 685

Asp Gly Gly Leu Ser Val Leu Arg Thr Phe Arg Leu Leu Arg Val Leu
        690                 695                 700

Lys Leu Val Arg Phe Met Pro Ala Leu Arg Arg Gln Leu Val Val Leu
705                 710                 715                 720

Met Lys Thr Met Asp Asn Val Ala Thr Phe Cys Met Leu Leu Met Leu
                725                 730                 735

Phe Ile Phe Ile Phe Ser Ile Leu Gly Met His Ile Phe Gly Cys Lys
                740                 745                 750

Phe Ser Leu Arg Thr Asp Thr Gly Asp Thr Val Pro Asp Arg Lys Asn
            755                 760                 765

Phe Asp Ser Leu Leu Trp Ala Ile Val Thr Val Phe Gln Ile Leu Thr
```

-continued

```
            770                 775                 780
Gln Glu Asp Trp Asn Val Val Leu Tyr Asn Gly Met Ala Ser Thr Ser
785                 790                 795                 800
Pro Trp Ala Ser Leu Tyr Phe Val Ala Leu Met Thr Phe Gly Asn Tyr
                    805                 810                 815
Val Leu Phe Asn Leu Leu Val Ala Ile Leu Val Glu Gly Phe Gln Ala
                820                 825                 830
Glu Gly Asp Ala Asn Arg Ser Tyr Ser Asp Glu Asp Gln Ser Ser Ser
                835                 840                 845
Asn Ile Glu Glu Phe Asp Lys Leu Gln Glu Gly Leu Asp Ser Ser Gly
            850                 855                 860
Asp Pro Lys Leu Cys Pro Ile Pro Met Thr Pro Asn Gly His Leu Asp
865                 870                 875                 880
Pro Ser Leu Pro Leu Gly Gly His Leu Gly Pro Ala Gly Ala Ala Gly
                    885                 890                 895
Pro Ala Pro Arg Leu Ser Leu Gln Pro Asp Pro Met Leu Val Ala Leu
                900                 905                 910
Gly Ser Arg Lys Ser Ser Val Met Ser Leu Gly Arg Met Ser Tyr Asp
                915                 920                 925
Gln Arg Ser Leu Ser Ser Ser Arg Ser Ser Tyr Tyr Gly Pro Trp Gly
            930                 935                 940
Arg Ser Ala Ala Trp Ala Ser Arg Arg Ser Ser Trp Asn Ser Leu Lys
945                 950                 955                 960
His Lys Pro Pro Ser Ala Glu His Glu Ser Leu Leu Ser Ala Glu Arg
                    965                 970                 975
Gly Gly Gly Ala Arg Val Cys Glu Val Ala Ala Asp Glu Gly Pro Pro
                980                 985                 990
Arg Ala Ala Pro Leu His Thr Pro His Ala His His Ile His His Gly
                995                 1000                1005
Pro His Leu Ala His Arg His Arg His His Arg Arg Thr Leu Ser Leu
            1010                1015                1020
Asp Asn Arg Asp Ser Val Asp Leu Ala Glu Leu Val Pro Ala Val Gly
1025                1030                1035                1040
Ala His Pro Arg Ala Ala Trp Arg Ala Ala Gly Pro Ala Pro Gly His
                    1045                1050                1055
Glu Asp Cys Asn Gly Arg Met Pro Ser Ile Ala Lys Asp Val Phe Thr
                1060                1065                1070
Lys Met Gly Asp Arg Gly Asp Arg Gly Glu Asp Glu Glu Ile Asp
                1075                1080                1085
Tyr Thr Leu Cys Phe Arg Val Arg Lys Met Ile Asp Val Tyr Lys Pro
            1090                1095                1100
Asp Trp Cys Glu Val Arg Glu Asp Trp Ser Val Tyr Leu Phe Ser Pro
1105                1110                1115                1120
Glu Asn Arg Phe Arg Val Leu Cys Gln Thr Ile Ile Ala His Lys Leu
                    1125                1130                1135
Phe Asp Tyr Val Val Leu Ala Phe Ile Phe Leu Asn Cys Ile Thr Ile
                1140                1145                1150
Ala Leu Glu Arg Pro Gln Ile Glu Ala Gly Ser Thr Glu Arg Ile Phe
                1155                1160                1165
Leu Thr Val Ser Asn Tyr Ile Phe Thr Ala Ile Phe Val Gly Glu Met
            1170                1175                1180
Thr Leu Lys Val Val Ser Leu Gly Leu Tyr Phe Gly Glu Gln Ala Tyr
1185                1190                1195                1200
```

-continued

```
Leu Arg Ser Ser Trp Asn Val Leu Asp Gly Phe Leu Val Phe Val Ser
            1205                1210                1215
Ile Ile Asp Ile Val Val Ser Leu Ala Ser Ala Gly Ala Lys Ile
            1220                1225                1230
Leu Gly Val Leu Arg Val Leu Arg Leu Arg Thr Leu Arg Pro Leu
            1235                1240                1245
Arg Val Ile Ser Arg Ala Pro Gly Leu Lys Leu Val Val Glu Thr Leu
            1250                1255                1260
Ile Ser Ser Leu Lys Pro Ile Gly Asn Ile Val Leu Ile Cys Cys Ala
1265                1270                1275                1280
Phe Phe Ile Ile Phe Gly Ile Leu Gly Val Gln Leu Phe Lys Gly Lys
            1285                1290                1295
Phe Tyr His Cys Leu Gly Val Asp Thr Arg Asn Ile Thr Asn Arg Ser
            1300                1305                1310
Asp Cys Met Ala Ala Asn Tyr Arg Trp Val His His Lys Tyr Asn Phe
            1315                1320                1325
Asp Asn Leu Gly Gln Ala Leu Met Ser Leu Phe Val Leu Ala Ser Lys
            1330                1335                1340
Asp Gly Trp Val Asn Ile Met Tyr Asn Gly Leu Asp Ala Val Ala Val
1345                1350                1355                1360
Asp Gln Gln Pro Val Thr Asn His Asn Pro Trp Met Leu Leu Tyr Phe
            1365                1370                1375
Ile Ser Phe Leu Leu Ile Val Ser Phe Phe Val Leu Asn Met Phe Val
            1380                1385                1390
Gly Val Val Val Glu Asn Phe His Lys Cys Arg Gln His Gln Glu Ala
            1395                1400                1405
Glu Glu Ala Arg Arg Arg Glu Glu Lys Arg Leu Arg Arg Leu Glu Lys
            1410                1415                1420
Lys Arg Arg Lys Ala Gln Arg Leu Pro Tyr Tyr Ala Thr Tyr Cys His
1425                1430                1435                1440
Thr Arg Leu Leu Ile His Ser Met Cys Thr Ser His Tyr Leu Asp Ile
            1445                1450                1455
Phe Ile Thr Phe Ile Ile Cys Leu Asn Val Val Thr Met Ser Leu Glu
            1460                1465                1470
His Tyr Asn Gln Pro Thr Ser Leu Glu Thr Ala Leu Lys Tyr Cys Asn
            1475                1480                1485
Tyr Met Phe Thr Thr Val Phe Val Leu Glu Ala Val Leu Lys Leu Val
            1490                1495                1500
Ala Phe Gly Leu Arg Arg Phe Phe Lys Asp Arg Trp Asn Gln Leu Asp
1505                1510                1515                1520
Leu Ala Ile Val Leu Leu Ser Val Met Gly Ile Thr Leu Glu Glu Ile
            1525                1530                1535
Glu Ile Asn Ala Ala Leu Pro Ile Asn Pro Thr Ile Ile Arg Ile Met
            1540                1545                1550
Arg Val Leu Arg Ile Ala Arg Val Leu Lys Leu Leu Lys Met Ala Thr
            1555                1560                1565
Gly Met Arg Ala Leu Leu Asp Thr Val Val Gln Ala Leu Pro Gln Val
            1570                1575                1580
Gly Asn Leu Gly Leu Leu Phe Met Leu Leu Phe Phe Ile Tyr Ala Ala
1585                1590                1595                1600
Leu Gly Val Glu Leu Phe Gly Lys Leu Val Cys Asn Asp Glu Asn Pro
            1605                1610                1615
```

-continued

```
Cys Glu Gly Met Ser Arg His Ala Thr Phe Glu Asn Phe Gly Met Ala
            1620                1625                1630

Phe Leu Thr Leu Phe Gln Val Ser Thr Gly Asp Asn Trp Asn Gly Ile
            1635                1640                1645

Met Lys Asp Thr Leu Arg Asp Cys Thr His Asp Glu Arg Ser Cys Leu
            1650                1655                1660

Ser Ser Leu Gln Phe Val Ser Pro Leu Tyr Phe Val Ser Phe Val Leu
1665                1670                1675                1680

Thr Ala Gln Phe Val Leu Ile Asn Val Val Ala Val Leu Met Lys
            1685                1690                1695

His Leu Asp Asp Ser Asn Lys Glu Ala Gln Glu Asp Ala Glu Met Asp
            1700                1705                1710

Ala Glu Leu Glu Leu Glu Met Ala His Gly Leu Gly Pro Gly Pro Arg
            1715                1720                1725

Leu Pro Thr Gly Ser Pro Gly Ala Pro Gly Arg Gly Pro Gly Gly Ala
            1730                1735                1740

Gly Gly Gly Gly Asp Thr Glu Gly Gly Leu Cys Arg Arg Cys Tyr Ser
1745                1750                1755                1760

Pro Ala Gln Glu Asn Leu Trp Leu Asp Ser Val Ser Leu Ile Ile Lys
            1765                1770                1775

Asp Ser Leu Glu Gly Glu Leu Thr Ile Ile Asp Asn Leu Ser Gly Ser
            1780                1785                1790

Ile Phe His His Tyr Ser Ser Pro Ala Gly Cys Lys Lys Cys His His
            1795                1800                1805

Asp Lys Gln Glu Val Gln Leu Ala Glu Thr Glu Ala Phe Ser Leu Asn
            1810                1815                1820

Ser Asp Arg Ser Ser Ser Ile Leu Leu Gly Asp Asp Leu Ser Leu Glu
1825                1830                1835                1840

Asp Pro Thr Ala Cys Pro Pro Gly Arg Lys Asp Ser Lys Gly Glu Leu
            1845                1850                1855

Asp Pro Pro Glu Pro Met Arg Val Gly Asp Leu Gly Glu Cys Phe Phe
            1860                1865                1870

Pro Leu Ser Ser Thr Ala Val Ser Pro Asp Pro Glu Asn Phe Leu Cys
            1875                1880                1885

Glu Met Glu Glu Ile Pro Phe Asn Pro Val Arg Ser Trp Leu Lys His
            1890                1895                1900

Asp Ser Ser Gln Ala Pro Pro Ser Pro Phe Ser Pro Asp Ala Ser Ser
1905                1910                1915                1920

Pro Leu Leu Pro Met Pro Ala Glu Phe Phe His Pro Ala Val Ser Ala
            1925                1930                1935

Ser Gln Lys Gly Pro Glu Lys Gly Thr Gly Thr Gly Thr Leu Pro Lys
            1940                1945                1950

Ile Ala Leu Gln Gly Ser Trp Ala Ser Leu Arg Ser Pro Arg Val Asn
            1955                1960                1965

Cys Thr Leu Leu Arg Gln Ala Thr Gly Ser Asp Thr Ser Leu Asp Ala
            1970                1975                1980

Ser Pro Ser Ser Ser Ala Gly Ser Leu Gln Thr Thr Leu Glu Asp Ser
1985                1990                1995                2000

Leu Thr Leu Ser Asp Ser Pro Arg Arg Ala Leu Gly Pro Pro Ala Pro
            2005                2010                2015

Ala Pro Gly Pro Arg Ala Gly Leu Ser Pro Ala Ala Arg Arg Leu
            2020                2025                2030

Ser Leu Arg Gly Arg Gly Leu Phe Ser Leu Arg Gly Leu Arg Ala His
```

-continued

```
                  2035                2040                     2045

Gln Arg Ser His Ser Ser Gly Gly Ser Thr Ser Pro Gly Cys Thr His
            2050                2055                2060

His Asp Ser Met Asp Pro Ser Asp Glu Glu Gly Arg Gly Gly Ala Gly
2065                2070                2075                2080

Gly Gly Gly Ala Gly Ser Glu His Ser Glu Thr Leu Ser Ser Leu Ser
                2085                2090                2095

Leu Thr Ser Leu Phe Cys Pro Pro Pro Pro Ala Pro Gly Leu
            2100                2105                2110

Thr Pro Ala Arg Lys Phe Ser Thr Ser Ser Leu Ala Ala Pro Gly
            2115                2120                2125

Arg Pro His Ala Ala Leu Ala His Gly Leu Ala Arg Ser Pro Ser
    2130                2135                2140

Trp Ala Ala Asp Arg Ser Lys Asp Pro Pro Gly Arg Ala Pro Leu Pro
2145                2150                2155                2160

Met Gly Leu Gly Pro Leu Ala Pro Pro Gln Pro Leu Pro Gly Glu
                2165                2170                2175

Leu Glu Pro Gly Asp Ala Ala Ser Lys Arg Lys Arg
            2180                2185

<210> SEQ ID NO 5
<211> LENGTH: 1835
<212> TYPE: PRT
<213> ORGANISM: Rattus sp.

<400> SEQUENCE: 5

Met Ala Asp Ser Asn Leu Pro Pro Ser Ser Ala Ala Pro Ala Pro
1               5                   10                  15

Glu Pro Gly Ile Thr Glu Gln Pro Gly Pro Arg Ser Pro Pro Ser
            20                  25                  30

Pro Pro Gly Leu Glu Glu Pro Leu Glu Gly Thr Asn Pro Asp Val Pro
        35                  40                  45

His Pro Asp Leu Ala Pro Val Ala Phe Phe Cys Leu Arg Gln Thr Thr
    50                  55                  60

Ser Pro Arg Asn Trp Cys Ile Lys Met Val Cys Asn Pro Trp Phe Glu
65                  70                  75                  80

Cys Val Ser Met Leu Val Ile Leu Leu Asn Cys Val Thr Leu Gly Met
                85                  90                  95

Tyr Gln Pro Cys Asp Asp Met Glu Cys Leu Ser Asp Arg Cys Lys Ile
            100                 105                 110

Leu Gln Val Phe Asp Asp Phe Ile Phe Ile Phe Phe Ala Met Glu Met
        115                 120                 125

Val Leu Lys Met Val Ala Leu Gly Ile Phe Gly Lys Lys Cys Tyr Leu
130                 135                 140

Gly Asp Thr Trp Asn Arg Leu Asp Phe Phe Ile Val Met Ala Gly Met
145                 150                 155                 160

Val Glu Tyr Ser Leu Asp Leu Gln Asn Ile Asn Leu Ser Ala Ile Arg
                165                 170                 175

Thr Val Arg Val Leu Arg Pro Leu Lys Ala Ile Asn Arg Val Pro Ser
            180                 185                 190

Met Arg Ile Leu Val Asn Leu Leu Asp Thr Leu Pro Met Leu Gly
        195                 200                 205

Asn Val Leu Leu Leu Cys Phe Phe Val Phe Phe Ile Phe Gly Ile Ile
        210                 215                 220
```

-continued

```
Gly Val Gln Leu Trp Ala Gly Leu Leu Arg Asn Arg Cys Phe Leu Glu
225                 230                 235                 240

Glu Asn Phe Thr Ile Gln Gly Asp Val Ala Leu Pro Pro Tyr Tyr Gln
            245                 250                 255

Pro Glu Glu Asp Asp Glu Met Pro Phe Ile Cys Ser Leu Thr Gly Asp
            260                 265                 270

Asn Gly Ile Met Gly Cys His Glu Ile Pro Pro Leu Lys Glu Gln Gly
            275                 280                 285

Arg Glu Cys Cys Leu Ser Lys Asp Asp Val Tyr Asp Phe Gly Ala Gly
            290                 295                 300

Arg Gln Asp Leu Asn Ala Ser Gly Leu Cys Val Asn Trp Asn Arg Tyr
305                 310                 315                 320

Tyr Asn Val Cys Arg Thr Gly Asn Ala Asn Pro His Lys Gly Ala Ile
            325                 330                 335

Asn Phe Asp Asn Ile Gly Tyr Ala Gly Ile Val Ile Phe Gln Val Ile
            340                 345                 350

Thr Leu Glu Gly Trp Val Glu Ile Met Tyr Tyr Val Met Asp Ala His
            355                 360                 365

Ser Phe Tyr Asn Phe Ile Tyr Phe Ile Leu Leu Ile Ile Val Gly Ser
            370                 375                 380

Phe Phe Met Ile Asn Leu Cys Leu Val Val Ile Ala Thr Gln Phe Ser
385                 390                 395                 400

Glu Thr Lys Gln Arg Glu His Arg Leu Met Leu Glu Gln Arg Gln Arg
            405                 410                 415

Tyr Leu Ser Ser Ser Thr Val Ala Ser Tyr Ala Glu Pro Gly Asp Cys
            420                 425                 430

Tyr Glu Glu Ile Phe Gln Tyr Val Cys His Ile Leu Arg Lys Ala Lys
            435                 440                 445

Arg Arg Ala Leu Gly Leu Tyr Gln Ala Leu Gln Asn Arg Arg Gln Ala
            450                 455                 460

Met Gly Pro Gly Thr Pro Ala Pro Ala Lys Pro Gly Pro His Ala Lys
465                 470                 475                 480

Glu Pro Ser His Cys Lys Leu Cys Pro Arg His Ser Pro Leu Asp Pro
            485                 490                 495

Thr Pro His Thr Leu Val Gln Pro Ile Ser Ala Ile Leu Ala Ser Asp
            500                 505                 510

Pro Ser Ser Cys Pro His Cys Gln His Glu Ala Gly Arg Arg Pro Ser
            515                 520                 525

Gly Leu Gly Ser Thr Asp Ser Gly Gln Glu Gly Ser Gly Ser Gly Gly
            530                 535                 540

Ser Ala Glu Ala Glu Ala Asn Gly Asp Gly Leu Gln Ser Ser Glu Asp
545                 550                 555                 560

Gly Val Ser Ser Asp Leu Gly Lys Glu Glu Gln Glu Asp Gly Ala
            565                 570                 575

Ala Arg Leu Cys Gly Asp Val Trp Arg Glu Thr Arg Lys Lys Leu Arg
            580                 585                 590

Gly Ile Val Asp Ser Lys Tyr Phe Asn Arg Gly Ile Met Met Ala Ile
            595                 600                 605

Leu Val Asn Thr Val Ser Met Gly Ile Glu His His Glu Gln Pro Glu
            610                 615                 620

Glu Leu Thr Asn Ile Leu Glu Ile Cys Asn Val Val Phe Thr Ser Met
625                 630                 635                 640

Phe Ala Leu Glu Met Ile Leu Lys Leu Ala Ala Phe Gly Leu Phe Asp
```

-continued

```
                    645                 650                 655
Tyr Leu Arg Asn Pro Tyr Asn Ile Phe Asp Ser Ile Ile Val Ile Ile
                660                 665                 670
Ser Ile Trp Glu Ile Val Gly Gln Ala Asp Gly Leu Ser Val Leu
            675                 680                 685
Arg Thr Phe Arg Leu Leu Arg Val Leu Lys Leu Val Arg Phe Met Pro
690                 695                 700
Ala Leu Arg Arg Gln Leu Val Val Leu Met Lys Thr Met Asp Asn Val
705                 710                 715                 720
Ala Thr Phe Cys Met Leu Leu Met Leu Phe Ile Phe Ile Phe Ser Ile
                725                 730                 735
Leu Gly Met His Ile Phe Gly Cys Lys Phe Ser Leu Arg Thr Asp Thr
                740                 745                 750
Gly Asp Thr Val Pro Asp Arg Lys Asn Phe Asp Ser Leu Leu Trp Ala
                755                 760                 765
Ile Val Thr Val Phe Gln Ile Leu Thr Gln Glu Asp Trp Asn Val Val
770                 775                 780
Leu Tyr Asn Gly Met Ala Ser Thr Thr Pro Trp Ala Ser Leu Tyr Phe
785                 790                 795                 800
Val Ala Leu Met Thr Phe Gly Asn Tyr Val Leu Phe Asn Leu Leu Val
                805                 810                 815
Ala Ile Leu Val Glu Gly Phe Gln Ala Glu Gly Asp Ala Asn Arg Ser
                820                 825                 830
Cys Ser Asp Glu Asp Gln Ser Ser Asn Leu Glu Glu Phe Asp Lys
                835                 840                 845
Leu Pro Glu Gly Leu Asp Asn Ser Arg Asp Leu Lys Leu Cys Pro Ile
                850                 855                 860
Pro Met Thr Pro Asn Gly His Leu Asp Pro Ser Leu Pro Leu Gly Ala
865                 870                 875                 880
His Leu Gly Pro Ala Gly Thr Met Gly Thr Ala Pro Arg Leu Ser Leu
                885                 890                 895
Gln Pro Asp Pro Val Leu Val Ala Leu Asp Ser Arg Lys Ser Ser Val
                900                 905                 910
Met Ser Leu Gly Arg Met Ser Tyr Asp Gln Arg Ser Leu Ser Ser Ser
                915                 920                 925
Arg Ser Ser Tyr Tyr Gly Pro Trp Gly Arg Ser Gly Thr Trp Ala Ser
                930                 935                 940
Arg Arg Ser Ser Trp Asn Ser Leu Lys His Lys Pro Pro Ser Ala Glu
945                 950                 955                 960
His Glu Ser Leu Leu Ser Gly Glu Gly Gly Ser Cys Val Arg Ala
                965                 970                 975
Cys Glu Gly Ala Arg Glu Glu Ala Pro Thr Arg Thr Ala Pro Leu His
                980                 985                 990
Ala Pro His Ala His His Ala His His Gly Pro His Leu Ala His Arg
                995                 1000                1005
His Arg His His Arg Arg Thr Leu Ser Leu Asp Thr Arg Asp Ser Val
                1010                1015                1020
Asp Leu Gly Glu Leu Val Pro Val Val Gly Ala His Ser Arg Ala Ala
1025                1030                1035                1040
Trp Arg Gly Ala Gly Gln Ala Pro Gly His Glu Asp Cys Asn Gly Arg
                1045                1050                1055
Met Pro Asn Ile Ala Lys Asp Val Phe Thr Lys Met Asp Asp Arg Arg
                1060                1065                1070
```

-continued

```
Asp Arg Gly Glu Asp Glu Glu Ile Asp Tyr Thr Leu Cys Phe Arg
         1075            1080            1085

Val Arg Lys Met Ile Asp Val Tyr Lys Pro Asp Trp Cys Glu Val Arg
         1090            1095            1100

Glu Asp Trp Ser Val Tyr Leu Phe Ser Pro Glu Asn Lys Phe Arg Ile
1105            1110            1115            1120

Leu Cys Gln Thr Ile Ile Ala His Lys Leu Phe Asp Tyr Val Val Leu
             1125            1130            1135

Ala Phe Ile Phe Leu Asn Cys Ile Thr Ile Ala Leu Glu Arg Pro Gln
         1140            1145            1150

Ile Glu Ala Gly Ser Thr Glu Arg Ile Phe Leu Thr Val Ser Asn Tyr
         1155            1160            1165

Ile Phe Thr Ala Ile Phe Val Gly Glu Met Thr Leu Lys Val Val Ser
         1170            1175            1180

Leu Gly Leu Tyr Phe Gly Glu Gln Ala Tyr Leu Arg Ser Ser Trp Asn
1185            1190            1195            1200

Val Leu Asp Gly Phe Leu Val Phe Val Ser Ile Ile Asp Ile Val Val
         1205            1210            1215

Ser Val Ala Ser Ala Gly Gly Ala Lys Ile Leu Gly Val Leu Arg Val
         1220            1225            1230

Leu Arg Leu Leu Arg Thr Leu Arg Pro Leu Arg Val Ile Ser Arg Ala
         1235            1240            1245

Pro Gly Leu Lys Leu Val Val Glu Thr Leu Ile Ser Ser Leu Lys Pro
         1250            1255            1260

Ile Gly Asn Ile Val Leu Ile Cys Cys Ala Phe Phe Ile Ile Phe Gly
1265            1270            1275            1280

Ile Leu Gly Val Gln Leu Phe Lys Gly Lys Phe Tyr His Cys Leu Gly
         1285            1290            1295

Val Asp Thr Arg Asn Ile Thr Asn Arg Ser Asp Cys Val Ala Ala Asn
         1300            1305            1310

Tyr Arg Trp Val His His Lys Tyr Asn Phe Asp Asn Leu Gly Gln Ala
         1315            1320            1325

Leu Met Ser Leu Phe Val Leu Ala Ser Lys Asp Gly Trp Val Asn Ile
         1330            1335            1340

Met Tyr Asn Gly Leu Asp Ala Val Ala Val Asp Gln Gln Pro Val Thr
1345            1350            1355            1360

Asn His Asn Pro Trp Met Leu Leu Tyr Phe Ile Ser Phe Leu Leu Ile
             1365            1370            1375

Val Ser Phe Phe Val Leu Asn Met Phe Val Gly Val Val Glu Asn
         1380            1385            1390

Phe His Lys Cys Arg Gln His Gln Glu Ala Glu Glu Ala Arg Arg Arg
         1395            1400            1405

Glu Glu Lys Arg Leu Arg Arg Leu Glu Lys Lys Arg Arg Lys Ala Gln
         1410            1415            1420

Arg Leu Pro Tyr Tyr Ala Thr Tyr Cys Pro Thr Arg Leu Leu Ile His
1425            1430            1435            1440

Ser Met Cys Thr Ser His Tyr Leu Asp Ile Phe Ile Thr Phe Ile Ile
             1445            1450            1455

Cys Leu Asn Val Val Thr Met Ser Leu Glu His Tyr Asn Gln Pro Thr
         1460            1465            1470

Ser Leu Glu Thr Ala Leu Lys Tyr Cys Asn Tyr Met Phe Thr Thr Val
         1475            1480            1485
```

```
Phe Val Leu Glu Ala Val Leu Lys Leu Val Ala Phe Gly Leu Arg Arg
    1490                1495                1500
Phe Phe Lys Asp Arg Trp Asn Gln Leu Asp Leu Ala Ile Val Leu Leu
1505                1510                1515                1520
Ser Val Met Gly Ile Thr Leu Glu Glu Ile Glu Ile Asn Ala Ala Leu
                1525                1530                1535
Pro Ile Asn Pro Thr Ile Ile Arg Ile Met Arg Val Leu Arg Ile Ala
                1540                1545                1550
Arg Val Leu Lys Leu Leu Lys Met Ala Thr Gly Met Arg Ala Leu Leu
                1555                1560                1565
Asp Thr Val Val Gln Ala Leu Pro Gln Val Gly Asn Leu Gly Leu Leu
                1570                1575                1580
Phe Met Leu Leu Phe Phe Ile Tyr Ala Ala Leu Gly Val Glu Leu Phe
1585                1590                1595                1600
Gly Lys Leu Val Cys Asn Asp Glu Asn Pro Cys Glu Gly Met Ser Arg
                1605                1610                1615
His Ala Thr Phe Glu Asn Phe Gly Met Ala Phe Leu Thr Leu Phe Gln
                1620                1625                1630
Val Ser Thr Gly Asp Asn Trp Asn Gly Ile Met Lys Asp Thr Leu Arg
                1635                1640                1645
Asp Cys Thr His Asp Glu Arg Thr Cys Leu Ser Ser Leu Gln Phe Val
                1650                1655                1660
Ser Pro Leu Tyr Phe Val Ser Phe Val Leu Thr Ala Gln Phe Val Leu
1665                1670                1675                1680
Ile Asn Val Val Val Ala Val Leu Met Lys His Leu Asp Asp Ser Asn
                1685                1690                1695
Lys Glu Ala Gln Glu Asp Ala Glu Met Asp Ala Glu Ile Glu Leu Glu
                1700                1705                1710
Met Ala His Gly Leu Gly Pro Cys Pro Gly Pro Cys Pro Gly Pro Cys
                1715                1720                1725
Pro Cys Pro Cys Pro Cys Pro Cys Ala Gly Pro Arg Leu Pro Thr Ser
                1730                1735                1740
Ser Pro Gly Ala Pro Gly Arg Gly Ser Gly Gly Ala Gly Ala Gly Gly
1745                1750                1755                1760
Asp Thr Glu Ser His Leu Cys Arg His Cys Tyr Ser Pro Ala Gln Glu
                1765                1770                1775
Thr Leu Trp Leu Asp Ser Val Ser Leu Ile Ile Lys Asp Ser Leu Glu
                1780                1785                1790
Gly Glu Leu Thr Ile Ile Asp Asn Leu Ser Gly Ser Val Phe His His
                1795                1800                1805
Tyr Ala Ser Pro Asp Gly Cys Gly Lys Cys His His Asp Lys Gln Glu
                1810                1815                1820
Thr Gly Leu His Pro Ser Cys Trp Gly Met Thr
1825                1830                1835

<210> SEQ ID NO 6
<211> LENGTH: 23
<212> TYPE: DNA
<213> ORGANISM: Homo sapiens

<400> SEQUENCE: 6
ctcacgaagt acagcggcga cac                                           23

<210> SEQ ID NO 7
<211> LENGTH: 25
```

```
<212> TYPE: DNA
<213> ORGANISM: Homo sapiens

<400> SEQUENCE: 7
gggcgccatc aactttgaca acatc                                            25

<210> SEQ ID NO 8
<211> LENGTH: 25
<212> TYPE: DNA
<213> ORGANISM: Homo sapiens

<400> SEQUENCE: 8
ctgggccctc agctgtttcg taatc                                            25

<210> SEQ ID NO 9
<211> LENGTH: 30
<212> TYPE: DNA
<213> ORGANISM: Homo sapiens

<400> SEQUENCE: 9
gcgctggtca tagctcatcc tccctagaga                                       30

<210> SEQ ID NO 10
<211> LENGTH: 22
<212> TYPE: DNA
<213> ORGANISM: Homo sapiens

<400> SEQUENCE: 10
gcgcttcttc aaggaccgat gg                                               22

<210> SEQ ID NO 11
<211> LENGTH: 24
<212> TYPE: DNA
<213> ORGANISM: Homo sapiens

<400> SEQUENCE: 11
cccaggtgtg gacgaagtat tgct                                             24

<210> SEQ ID NO 12
<211> LENGTH: 6503
<212> TYPE: DNA
<213> ORGANISM: Rattus sp.

<400> SEQUENCE: 12
cggtccgccg ctcgtccgcg ccacccgcct cgagccgcgc ggacccgccc gccatggccc       60
gcgcccccgg gcccgccgcc ctgcatgcgc cgtcccccctc gccccggggg cgcagctgat     120
cccggaatcc gaggcgtggg gccggcgggg cgcgggtcc ctctccacgc cggcttcggg       180
gacacgcgtc aaccccgcgt tctctgcccgg gacgacccccg ctgcccggcc acgtccatgc    240
caagggctcc ctgctccacg ctgacatggc tgacagcaac ttaccgccct catctgcagc      300
agccccggcc cctgagccgg gaatcactga gcagccgggg ccccggagtc cccctccatc      360
ccctccaggc ctggaggagc cattggaagg aaccaaccct gacgtccac atccagacct       420 ggctcctgtt gctttcttct gcctgcgcca gaccacgagc ccacggaact ggtgcatcaa      480
gatggtttgt aacccgtggt tcgagtgtgt gagcatgctg gttattctgc tgaactgtgt     540
gaccctgggc atgtaccagc catgtgatga catggagtgc ctgtcggacc gttgcaagat      600
cctgcaggtc ttcgatgact tcatcttcat cttctttgcc atggagatgg tgcttaagat     660 ggtgccctg gcatttttg gcaagaagtg ctacctcgga gacacatgga accgcctgga      720
```

-continued

```
tttcttcatt gtcatggcag ggatggttga gtactctctg gacctacaga acatcaacct      780
gtcagccatc cgcactgtgc gtgtcctgag gcctctcaaa gccatcaacc gtgtacccag      840
catgcggatc ctggtgaacc tgctgctcga cacgctgccc atgctgggga acgtgctcct      900
gctctgtttc ttcgtcttct tcatcttcgg catcattggc gtgcagctct gggcaggcct      960
gctacggaac cgctgcttcc tggaagagaa cttcaccata caaggggatg tgccctgcc     1020
cccttattac caaccagagg aggatgacga gatgcccttt atctgctccc tgactgggga     1080
caatggcatc atgggctgcc acgagatccc cccactgaag gagcagggcc gggaatgctg     1140
cctgtccaaa gatgatgtgt atgacttcgg ggcggggcgc caggacctca cgccagcgg     1200
tctgtgcgtc aactggaacc gctactacaa cgtctgccgc acgggcaacg ccaaccctca     1260
caagggcgcc atcaactttg acaacattgg ctatgccggg attgtgattt ccaggtgat     1320
cactctggaa ggctgggtgg agatcatgta ctatgtgatg gacgcacatt ctttctacaa     1380
cttcatctac ttcattctgc tcatcatagt gggctccttc ttcatgatca acttgtgcct     1440
cgttgtcata gcaacccagt tctctgagac caagcaacgg gagcaccggc tgatgctgga     1500
gcaacgccag cgctacctgt cctccagcac ggtggccagt tacgctgagc ccggtgattg     1560
ctatgaggag atcttccaat atgtctgtca catccttcgc aaagccaagc gccgtgccct     1620
aggcctctac caggccctgc agaaccggcg ccaggccatg ggcccgggga caccagcccc     1680
tgccaagcct gggccccatg ccaaggagcc cagccactgc aagctgtgcc cacgacacag     1740
ccccctggac cccactcccc acacactggt gcagcccatc tctgccattc tggcctctga     1800
ccccagcagc tgccctcact gccagcacga ggcaggcagg cggccctctg gcctgggcag     1860
cactgactca ggccaggaag gctcaggttc tggtggctct gcagaggccg aagccaatgg     1920
ggatggactc cagagcagtg aggatggggt ctcctcggac ctggggaagg aggaggaaca     1980
ggaggacggg gcagcccgac tgtgtgggga tgtgtggcgc gagacacgaa aaaagctgcg     2040
gggcatcgtg gacagcaagt acttcaacag aggtatcatg atggctatcc tggtgaacac     2100
agtcagcatg ggcatcgagc accacgaaca gcccgaggag ctgaccaaca tcctggagat     2160
ctgcaatgtg gtcttcacca gtatgtttgc cctggagatg atcctgaaac tggccgcctt     2220
tgggctcttc gactacctgc ggaacccctta caacatcttt gacagcatca tcgtcatcat     2280
cagcatctgg gaaatcgtgg ggcaggcgga cggtggcctg tctgtgctgc gcaccttccg     2340
gttgctgcgg gtgctgaagc tggtgcgctt catgccggcg ctgcggcgcc agctcgtggt     2400
gctcatgaag accatggaca acgtggccac cttctgcatg ctactcatgc tgttcatctt     2460
catcttcagc atccttggga tgcatatctt tggctgcaaa ttcagcctcc gcacggacac     2520
gggagacacc gttcctgaca ggaagaactt cgattcctta ctgtgggcca tcgtcacagt     2580
gttccagatc ctcactcagg aggactggaa cgttgtcctg tacaatggca tggcctccac     2640
cacccccctgg gcctccctct attttgttgc cctcatgacc tttggcaact acgttctctt     2700
caatctcctg gtggctatcc tggtagaggg ttttccaggct gagggtgatg ctaatcgttc     2760
ctgctctgat gaggaccaga gctcatccaa tttggaggag tttgacaagc tcccagaggg     2820
cctggacaac agtagagatc tcaagctctg cccaataccc atgacaccca atggacacct     2880
ggaccctagc ctccctctgg gtgcgcatct gggtcctgct ggtaccatgg gtactgcccc     2940
ccgcctctca ctgcagccag acccggtact ggtggcccta gactctcgga aaagcagtgt     3000
catgtccctg ggcaggatga gctatgatca gcgatccttg tccagctccc ggagctccta     3060
ctacgggccc tggggccgca gtgggacctg ggctagccgc cgctccagct ggaacagcct     3120
```

```
gaaacacaag ccgccctcag ctgagcatga gtccttactg tctggggagg gtggaggtag   3180
ctgcgtcagg gcctgtgaag gcgcccggga ggaggcgcca actcgcaccg caccectgca   3240 tgctccacac gcgcaccacg cgcaccatgg accccacctg gcacaccgtc accgacacca   3300
ccgccggact ctgtcccttg ataccaggga ctctgttgac ctgggagagc tggtgcccgt   3360
ggtgggtgcc cactcacggg ccgcttggag ggggcgggt caggccctg gcacgagga     3420 ctgcaatggc agaatgccca acatagccaa ggatgtcttc accaagatgg atgaccgccg   3480
cgaccgcggg gaggacgagg aggagatcga ctatacccctg tgtttccggg tccgcaagat  3540
gattgatgtg tacaagccgg actggtgcga agtccgcgag gactggtcgg tctacctctt   3600
ctcccccgag aacaagttcc ggatcctgtg tcagaccatc attgctcaca gcttttga    3660 ctacgtggtc ttggccttta tcttcctcaa ctgtatcacc attgctctgg agagacccca   3720
gattgaagct ggtagcactg agcgcatctt cctcacggtg tctaactaca tcttcacagc   3780
catcttcgtg ggcgagatga cactgaaggt ggtttctctg gcctgtact ttggtgagca    3840 ggcgtacctg cgtagcagct ggaatgtact ggatggtttc ctggtctttg tgtccatcat   3900
cgatatcgta gtgtccgtgg cctctgctgg gggagccaag attctgggg tcctccgggt    3960 cctgcggctc ctgcgtacct tacgtccttt gagggttatc agccgggccc ctgggctgaa   4020
gctggtggta gagacgctca tctcctccct caagcccatt gggaacatcg tcctcatctg   4080
ctgtgccttt tcatcatct tcggcatcct gggggtgcag ctttttcaaag gcaagttcta    4140 ccattgtttg ggagtggaca cccgaaacat caccaaccga tctgactgcg tggcggccaa   4200
ctaccgctgt gtgcatcaca aatacaactt gacaacctg gccaggcat tgatgtccct     4260 cttgtcttg gcctccaagg acggctgggt gaacatcatg tataatggat tagatgctgt    4320
tgctgtggac cagcagccag tgacgaacca caaccctgg atgctactgt acttcatttc    4380
gttcctgctc atcgtcagct ctttgtgct caacatgttt gtgggcgtgg tcgtggagaa    4440
cttccacaag tgccggcagc accaggaggc tgaggaggcg cggaggcgtg aggagaaacg   4500
gctgcggcgc ctggaaaaga agcgccgtaa ggctcagagg ctgccctact atgctaccta   4560
ctgtcccaca aggctgctca tccactccat gtgcaccagc cactacctgg acatcttcat   4620
taccttcatc atctgcctca atgttgtcac catgtccctg gagcactaca accagcctac   4680
atccctagag acagccctta gtactgcaa ctacatgttc accactgtct ttgtgctgga   4740
ggctgtgctg aagctggtgg catttggcct gaggcgttttc ttcaaggacc gatggaacca    4800
gctggacctg gccattgtgc tgctgtccgt catgggcatc acactggagg agatcgagat   4860
caatgccgcc cttcccatca accccaccat catccgtatc atgcgtgttc tgcgtatcgc   4920
ccgggtgttg aagctattga agatggccac aggaatgcgg gccctgctgg acacagtggt   4980
acaggctctg ccccaggtgg gcaacctggg cctgctcttc atgctgctct tcttcatcta   5040
tgctgctctg ggagtggagc tcttcggaaa gctggtctgc aatgacgaga acccgtgtga   5100
gggcatgagc cggcacgcca cctttgaaaa cttcggcatg gccttcctca cgctcttcca   5160
ggtctccaca ggcgataact ggaatggaat tatgaaggac accctgcgag actgtaccca   5220
tgatgagcgc acgtgcctaa gcagcctgca gtttgtgtca ccgctctact ttgtgagctt   5280
cgtgctcaca gctcagttcg tgctcatcaa cgtggtggtg gccgtgctga tgaaacatct   5340
ggatgacagc aacaaggagg cccaggagga tgcagagatg gatgctgaga tcgagctgga   5400
gatggcccat ggcctcggcc cctgccctgg cccctgccct ggtccctgcc cctgcccctg   5460
```

-continued

```
cccctgcccc tgtgctggcc cgaggctgcc cactagttca cctggggctc cggggcgagg   5520
atcgggaggg gcaggtgctg gaggcgacac cgagagtcac ctgtgccggc actgctattc   5580
tccagcccag gagaccctgt ggctggacag cgtctcttta atcatcaagg actccttgga   5640
gggggagctg accatcattg acaacctgtc tgggtccgtc ttccaccact acgcctcacc   5700
tgacggctgt ggcaagtgtc accatgacaa gcaagagaca ggtcttcatc catcctgctg   5760
ggggatgacc tgagtcttga ggaccccacg gcctgcccac agggcccca ggagagcaag    5820
ggtgaactag agcctccgga gcccatgcag gctggagacc tggatgaatg cttttggccc   5880
tttgccaagc gagccagtgt ccacaggccc agagagcctg ctgtgcgaga tggggccat    5940
tccattcaac cctgtccagt cctggctcaa acacgagagc agccaagcac cccagagccc   6000
tttctccccg gatggctcca gccctctcct gtagatgcct gctgagttct tccaccctgc   6060
tgtgtctgcc agccagaagg ggcaggaacc gggcatgagt gcaggaaccc tgcccaagat   6120
tgcacttcag gggtcctggg catcgctgag gtcaccgagt gtcaactgca ccctcttgcg   6180
ccaggctact gtgagtgaca cgtccttgga tgccagtcct agcagctcag cgggcagcct   6240
acagaccaca ctggaagaca gtctgactct gagtgacagt ccccggcgtg ccctggggcc   6300
gccggtccag gtgcctgggc cacgggctag cctgtcaccg gccacccgg cgccgcctca    6360
gcctgcgggg ccgtggcctg tttagtctgc gtgggctgcg ggcccatcag cgtagccaca   6420
gcagtggcgg ctccaccagc cctggctgca ctcaccacga ctccatggac ccctctgatg   6480
aggagggccg cgggggagca ggt                                          6503
```

T-TYPE CALCIUM CHANNEL VARIANTS; COMPOSITIONS THEREOF; AND USES

RELATED APPLICATIONS

This U.S. patent application claims priority under 35 U.S.C. 119(e) to U.S. Provisional Application Serial No. 60/102,222, filed Sep. 29, 1998, incorporated herein by reference in its entirety.

FIELD OF THE INVENTION

The present invention relates to nucleic acid and amino acid sequences of human T-type calcium channel variants and the use of these sequences in diagnosis of disease states associated with pain and for use as targets for screening therapeutic compounds useful in the treatment of disease states associated with pain.

BACKGROUND OF THE INVENTION

Voltage-gated calcium channels can be divided into high- and low-threshold types. The high-threshold channels include the dihydropyridine-sensitive L-type, the ω-conotoxin GVIA-sensitive N-type and ω-agatoxin IVA-sensitive P-type. Depending on the tissue, these channel subtypes consist of $\alpha_1$, $\alpha_2\delta$, $\beta$ and $\gamma$ subunits. (Perez-Reyes and Schneider (1995) Kid. Int. 48:1111–1124.) To date, only one type of low-threshold calcium channel is known, the T-type calcium channel.

T-type calcium channels have hyperpolarized steady-state inactivation characteristics, a low threshold for inactivation, small single channel conductance and display rapid inactivation kinetics. (Ertel and Ertel (1997) Trends Pharmacol. Sci. 18:37–42.) The functional roles for T-type calcium channels in neurons include membrane depolarization, calcium entry and burst firing. (White et al. (1989) Proc. Natl. Acad. Sci. USA 86:6802–6806.) T-type calcium channels are found in many neurons of the central and peripheral nervous systems, including small and medium diameter neurons of the dorsal root ganglia (Scroggs and Fox (1992) J. Physiol. 445:639–658) and neurons in the thalamus. (Suzuki and Rogawski (1989) Proc. Natl. Acad. Sci. USA 86:7228–7232.)

Calcium currents have been found to be important in several neurological and muscular functions, e.g., pain transmission, cardiac pacemaker activity, etc. Improper functioning of these channels has been implicated in arrythmias, chronic peripheral pain, improper pain transmission in the central nervous system, and epilepsy.

Anti-epileptic drugs are known to cause a reduction of the low-threshold calcium current (LTCC or T-type $Ca^{2+}$ current) in thalamic neurons. (Coulter et al.(1989) Ann. Neurol. 25:582–593.) One such anti-epileptic compound, ethosuximide, has been shown to fully block T-type $Ca^{2+}$ current in freshly dissected neurons from dorsal root ganglia (DRG neurons) of adult rats (Todorovic and Lingle (1998) J. Neurophysiol. 79:240–252), and may have limited efficacy in the treatment of abnormal, chronic pain syndromes that follow peripheral nerve damage.

Molecular cloning has revealed the cDNA and corresponding amino acid sequences of several different α1 subunits ($\alpha_{1A}$, $\alpha_{1B}$, $\alpha_{1C}$, $\alpha_{1D}$, $\alpha_{1E}$, $\alpha_{1G}$, $\alpha_{1H}$, $\alpha_{1I}$, and $\alpha_{1S}$). While the cloned α1 subunits identified thus far correspond to several of the calcium channels found in cells, they do not account for all types of calcium conductance found in native cells.

The present invention relates to the discovery of human T-type calcium channel $\alpha_{1I}$ subunit variants that are useful in diagnosis of disease states associated with the peripheral nervous system and for screening compounds that may be used in the treatment of mammals for these disease states.

SUMMARY OF THE INVENTION

The invention is based on the discovery of human T-type calcium channel $\alpha_{1I}$ subunit variants (TCCV-1 and TCCV-2), the polynucleotides encoding TCCV-1 or TCCV-2, and the use of these compositions in screening for compounds effective in treating disease states associated with peripheral pain, and the use of these compositions for diagnosis of these disease states. In particular, the present invention expression vectors, host cells, antibodies, diagnostic kits, and transgenic/knockout animals are provided.

The invention features an isolated polynucleotide encoding TCCV-1 or TCCV-2 polypeptides. The invention further provides an isolated polynucleotide, encoding a TCCV-1 or TCCV-2 polypeptide wherein the polynucleotide encodes an TCCV-1 or TCCV-2 polypeptide comprising the amino acid sequence of SEQ ID NO:2 or 4, respectively. In certain embodiments, the polynucleotide is detectably labeled or is complementary to the polynucleotide encoding a TCCV-1 or TCCV-2 polypeptide. The complementary polynucleotide can also be detectably labeled. In another embodiment, the polynucleotide comprises the nucleic acid sequence of SEQ ID NO:1 or 3.

The present invention encompasses an expression vector comprising the polynucleotide encoding SEQ ID NO:2 or 4. Also contemplated is a host cell comprising the polynucleotide encoding SEQ ID NO:2 or 4. The host cell can be a prokaryotic or eukaryotic cell. The invention further comprises a method of producing a TCCV-1 or TCCV-2 polypeptide comprising: culturing the host cell comprising the expression vector comprising the polynucleotide encoding SEQ ID NO:2 or 4 under conditions suitable for expression of the polypeptide; and recovering the polypeptide from the host cell.

The present invention also contemplates a method of detecting a polynucleotide encoding a TCCV-1 or TCCV-2 polypeptide in a sample containing nucleic acid material, comprising the steps of: contacting the sample with a polynucleotide which is the complement of the polynucleotide encoding SEQ ID NO:2 or 4, wherein the complement is detectably labeled, under conditions suitable for formation of a hybridization complex; and detecting the complex, wherein the presence of the complex is indicative of the presence of the polynucleotide encoding the polypeptide in the sample.

The present invention provides a diagnostic test kit comprising: the polynucleotide comprising SEQ ID NO:1 or 3; and instructions for conducting the diagnostic test.

The present invention encompasses a method of screening for a compound that modulates TCCV-1 or TCCV-2 activity comprising: contacting TCCV-1 or TCCV-2, or fragment thereof with the compound; and detecting modulation of TCCV-1 or TCCV-2 activity. In certain embodiments, the TCCV-1 or TCCV-2 is expressed on a cell or tissue or immobilized on a solid support. The compound can be an antagonist or agonist of TCCV-1 or TCCV-2 activity. In a further embodiment, the compound is ethosuximide or an analog thereof.

The present invention provides an isolated TCCV-1 or TCCV-2 polypeptide or fragment thereof. In certain embodiments, the polypeptide comprises the amino acid sequence of SEQ ID NO:2 or 4. The polypeptide is recombinantly produced or synthetically produced. The present invention also provides an isolated antibody which specifically binds to the polypeptide of SEQ ID NO:2 or 4.

The present invention encompasses a transgenic nonhuman mammal comprising the polynucleotide encoding TCCV-1 or TCCV-2 polypeptide. The transgenic nonhuman mammal can also comprise the polynucleotide which is the -complement of the polynucleotide encoding TCCV-1 or TCCV-2 which is capable of hybridizing to a polynucleotide encoding TCCV-1 or TCCV-2, thereby reducing expression of TCCV-1 or TCCV-2.

BRIEF DESCRIPTION OF FIGURES AND SEQUENCE IDENTIFIERS

FIGS. 1A–1F show the amino acid alignment between TCCV-1 (SEQ ID NO:2), TCCV-2 (SEQ ID NO:4), and rat T-type Calcium Channel subunit $\alpha_{1I}$ (GenBank Accession No. AAD17796; SEQ ID NO:5). Residues that differ between the rat and human sequences are indicated in bold.

FIGS. 2A–2C show the splicing differences between the 3' ends of TCCV-1 (nucleotides 5148 through 6015 of SEQ ID NO:1) or TCCV-2 (nucleotides 5148 through 6054 of SEQ ID NO:3), and GenBank Accession No. AF086827 (nucleotides 4927 through 5847 of SEQ ID NO:12). Downward pointing arrows indicate exon boundaries. Forward arrows indicate forward PCR primers (Primer Numbers 6352, 6344/88, 6495, and 6495/37). Reverse arrows indicate reverse or antisense PCR primers (Primer Number 6831). Nucleotide differences in the rat sequence which differ from the human PCR primer sequences are underlined.

FIG. 3 shows a 2.0% agarose gel of PCR products following 36 cycles of amplifications using various primers as shown in FIGS. 2A–2C on human brain cDNA. Lane 1 is a 100 bp ladder (Life Technologies, Bethesda, Md.); Lane 3 is the PCR product following amplification with forward primer 6352 and reverse primer 6831; Lane 4 is the PCR product following amplification with forward primer 6344/88 and reverse primer 6831; Lane 5 is the PCR product following amplification with forward primer 6495 and reverse primer 6831; and Lane 6 is the result of amplification with forward primer 6495/37 and reverse primer 6831.

SEQ ID NO:1 is the polynucleotide sequence for TCCV-1. SEQ ID NO:2 is the putative encoded polypeptide.

SEQ ID NO:3 is the polynucleotide sequence for TCCV-2. SEQ ID NO:4 is the putative encoded polypeptide.

SEQ ID NO:5 is the amino acid sequence of GenBank Accession No. AAD17796.

SEQ ID NO:6 through SEQ ID NO:11 are PCR primers used in assembly of full length TCCV-1 and TCCV-2.

SEQ ID NO:12 is the nucleic acid sequence of GenBank Accession No. AF086827.

DETAILED DESCRIPTION OF THE INVENTION

Before the present proteins, nucleotide sequences, and methods are described, it is to be understood that the present invention is not limited to the particular methodologies, protocols, cell lines, vectors, and reagents described, as these may vary. It is also understood that the terminology used herein is for the purpose of describing particular embodiments only, and is not to limit the scope of the present invention.

The singular forms "a," "an," and "the" include plural reference unless the context clearly dictates otherwise.

All technical and scientific terms used herein have the same meanings as commonly understood by one of ordinary skill in the art to which this invention pertains. The practice of the present invention will employ, unless otherwise indicated, conventional techniques of protein chemistry and biochemistry, molecular biology, microbiology and recombinant DNA technology, which are within the skill of the art. Such techniques are explained fully in the literature.

Although any machines, materials, and methods similar or equivalent to those described herein can be used to practice or test the present invention, the preferred machines, materials, and methods are now described. All patents, patent applications, and publications mentioned herein, whether supra or infra, are each incorporated by reference in its entirety.

Definitions

"TCCV" refers to the amino acid sequences of substantially purified TCCV-1 or TCCV-2 obtained from any species particularly mammalian species, including bovine, ovine, porcine, murine, equine, and preferably the human species, from any source, whether natural, synthetic, semi-synthetic, or recombinant.

"Agonist" refers to a molecule which, when bound to TCCV-1 or TCCV-2, or is within proximity of TCCV-1 or TCCV-2, modulates the activity of TCCV-1 or TCCV-2 by increasing or prolonging the duration of the effect of TCCV-1 or TCCV-2. Agonists can include proteins, nucleic acids, carbohydrates, organic compounds, inorganic compounds, or any other molecules which modulate the effect of TCCV-1 or TCCV-2.

An "allelic variant" as used herein, is an alternative form of the gene encoding TCCV-1 or TCCV-2. Allelic variants may result from at least one mutation in the nucleic acid sequence and may result in altered mRNAs or in a polypeptide whose structure or function may or may not be altered. Any given recombinant gene may have none, one, or several allelic forms. Common mutational changes which give rise to allelic variants are generally ascribed to natural deletions, additions, or substitutions of nucleotides. Each of these types of changes may occur alone, or in combination with the others, one or more times in a given sequence.

"Amplification" relates to the production of additional copies of a nucleic acid sequence. Amplification can be carried out using polymerase chain reaction (PCR) technologies or other methods well known in the art.

The term "analog" is used herein in the conventional pharmaceutical sense. In chemical terminology, an analog refers to a molecule that structurally resembles a referent molecule but which has been modified in a targeted and controlled manner to replace a certain substituent of the referent molecule with an alternate substituent other than hydrogen.

"Antagonist" refers to a molecule which, when bound to TCCV-1 or TCCV-2 or within close proximity, decreases the amount or the duration of the biological or immunological activity of TCCV-1 or TCCV-2. Antagonists may include proteins, nucleic acids, carbohydrates, antibodies, organic compounds, inorganic compounds, or any other molecules which exert an effect on TCCV-1 or TCCV-2 activity.

"Antibody" can be an intact molecule or fragments thereof, such as Fab, F(ab)$_2$, and Fv fragments, which are capable of binding an epitopic determinant. The antibody can be polyclonal, monoclonal, or recombinantly produced.

The terms "antigenic determinant" or "epitopic determinant" refer to the fragment of a molecule that makes contact with a particular antibody.

The term "antisense" refers to any composition containing nucleic acids which is complementary to the "sense" strand of a specific nucleic acid molecule. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

A "coding sequence" is a polynucleotide sequence that is transcribed into mRNA and translated into a polypeptide. The boundaries of the coding sequence are determined by a translation start codon at the 5'-terminus and a translation stop codon at the 3'-terminus. A coding sequence can include, but is not limited to, mRNA, cDNA, synthetic DNA, and recombinant polynucleotide sequences. Also included is genomic DNA where the coding sequence is interrupted by introns.

"Complementary" and "complementarity" refer to the natural binding of polynucleotides to other polynucleotides by base pairing. For example, the sequence "5' A-C-G-T 3'" will bind to the complementary sequence "3' T-G-C-A 5'." Complementarity between two single stranded molecules may be "partial," such that only some of the nucleic acids bind, or it may be "complete," such that total complementarity exists between the single stranded molecules.

A "composition comprising a given polynucleotide sequence" and a "composition comprising a given amino acid sequence" refer broadly to any composition containing the given polynucleotide or amino acid sequence.

The term "control elements" refers collectively to promoters, ribosome binding sites, polyadenylation signals, transcription termination sequences, upstream regulatory domains, enhancers, and the like, which collectively provide for the transcription and translation of a coding sequence in a host cell. Not all of these control sequences need always be present in a recombinant vector so long as the desired gene is capable of being transcribed and translated.

The phrase "correlates with expression of a polynucleotide" refers to the detection of the presence of nucleic acids, the same or related to a nucleic acid sequence encoding TCCV-1 or TCCV-2, e.g., by northern analysis or RT-PCR, is indicative of the presence of nucleic acids encoding TCCV-1 or TCCV-2 in a sample, and thereby is indicative of the expression of the transcript from the polynucleotide encoding TCCV-1 or TCCV-2.

The phrase "detectably labeled" as used herein means joining, either covalently or non-covalently to the polynucleotides, polypeptides, or antibodies of the present invention, a substance which provides for a detectable signal. A wide variety of labels and conjugation techniques are well known in the art. Suitable labels include radionuclides, e.g., $^{32}$P, $^{35}$S, $^{3}$H, enzymes, substrates, cofactors, inhibitors, fluorescent moieties, chemiluminescent moieties, magnetic particles, and the like.

The phrase "disease state" means any disease, condition, symptom, or indication.

The term "expression" as used herein intends both transcriptional and translational processes, i.e., the production of messenger RNA and/or the production of protein therefrom.

The term "hybridization complex" refers to a complex formed between two nucleic acid sequences by virtue of the formation of hydrogen bonds between complementary bases. A hybridization complex may be formed in solution (conditions calculated by performing, e.g., $C_0t$ or $R_0t$) or formed between one nucleic acid sequence present in solution and another nucleic acid sequence immobilized on a solid support (e.g., paper, membranes, filters, chips, pins, glass slides, or any other appropriate substrate to which cells or their nucleic acids have been fixed.)

An "isolated polynucleotide" that encodes a particular polypeptide refers to a polynucleotide that is substantially free of other nucleic acid molecules that do not encode the subject polypeptide; however, the molecule may include functionally and/or structurally conservative mutations as defined herein.

The term "modulate" refers to a change in the activity of TCCV-1 or TCCV-2. For example, modulation may cause an increase or a decrease in protein activity, binding characteristics, or any other biological, functional, or immunological properties of TCCV-1 or TCCV-2. The ability to modulate the activity of TCCV-1 or TCCV-2 can be exploited in assays to screen for organic, inorganic, or biological compounds which affect the above properties of TCCV-1 or TCCV-2.

"Nucleic acid" and "nucleic acid sequence" refer to a nucleotide, oligonucleotide, polynucleotide, or any fragment thereof. These phrases also refer to DNA or RNA of genomic or synthetic origin which may be single stranded or double stranded and may represent the sense of the antisense strand, a peptide nucleic acid (PNA), or any DNA-like or RNA-like material. In this context, "fragments" refer to those nucleic acids which, when translated, would produce polypeptides retaining some functional characteristic, e.g., antigenicity, or structural domain, e.g., ion channel domain, characteristic of the full-length polypeptide.

The terms "operably associated" and "operably linked" refer to functionally related but heterologous nucleic acid sequences. A promoter is operably associated or operably linked with a coding sequence if the promoter controls the translation or expression of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

An "oligonucleotide" refers to a nucleic acid molecule of at least about 6 to 50 nucleotides, preferably about 15 to 30 nucleotides, and more preferably 20 to 25 nucleotides, which can be used in PCR amplification or in a hybridization assay. "Oligonucleotide" is substantially equivalent to the terms "amplimer," "primer," "oligomer," and "probe" as these terms are commonly defined in the art.

"Peptide nucleic acid" (PNA) refers to an antisense molecule or anti-gene agent which comprises an oligonucleotide of at least 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell.

The phrases "percent identity" and "% identity" refers to the percentage of sequence similarity found by a comparison or alignment of two or more amino acid or nucleic acid sequences. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353–358, National Biomedical Research Foundation, Washington, D.C., which adapts the local homology algorithm of Smith and Waterman (1981) *Advances in Appl. Math.* 2:482–489, for peptide analysis.

Programs for determining nucleotide sequence identity are available in the Wisconsin Sequence Analysis Package, Version 8 (Genetics Computer Group, Madison, Wis.) for example, the BLAST, BESTFIT, FASTA, and GAP programs, which also rely on the Smith and Waterman algorithm. These programs are readily utilized with the default parameters recommended by the manufacturer and described in the Wisconsin Sequence Analysis Package referred to above. Other programs for calculating identity or similarity between sequences are known in the art.

"Recombinant host cells," "host cells," "cells," "cell lines," "cell cultures," and other such terms denoting cell lines cultured as unicellular entities refer to cells which can be, or have been, used as recipients for recombinant vectors or other transfer DNA, immaterial of the method by which the DNA is introduced into the cell or the subsequent disposition of the cell. The terms include the progeny of the original cell which has been transfected. Cells in primary culture as well as cells such as oocytes also can be used as recipients.

A "reporter gene" is a gene that, upon expression, confers a phenotype on a cell expressing the reporter gene, such that the cell can be identified under appropriate conditions. For example, the reporter gene may produce a polypeptide product that can be easily detected or measured in a routine assay. Suitable reporter genes known in the art which confer this characteristic include those that encode chloramphenicol acetyl transferase (CAT activity), β-galactosidase, luciferase, alkaline phosphatase, human growth hormone, fluorescent proteins, such as green fluorescent protein (GFP), and others. Indeed, any gene that encodes a protein or enzyme that can readily be measured, for example, by an immunoassay such as an enzyme-linked immunosorbent assay (ELISA) or by the enzymatic conversion of a substrate into a detectable product, and that is substantially not expressed in the host cells (specific expression with no background) can be used as a reporter gene to test for promoter activity. Other reporter genes for use herein include genes that allow selection of cells based on their ability to thrive in the presence or absence of a chemical or other agent that inhibits an essential cell function. Suitable markers, therefore, include genes coding for proteins which confer drug resistance or sensitivity thereto, or change the antigenic characteristics of those cells expressing the reporter gene when the cells are grown in an appropriate selective medium. For example, reporter genes include: cytotoxic and drug resistance markers, whereby cells are selected by their ability to grow on media containing one or more of the cytotoxins or drugs; auxotrophic markers by which cells are selected by their ability to grow on defined media with or without particular nutrients or supplements; and metabolic markers by which cells are selected for, e.g., their ability to grow on defined media containing the appropriate sugar as the sole carbon source. These and other reporter genes are well known in the art.

A "change in the level of reporter gene product" is shown by comparing expression levels of the reporter gene product in a cell exposed to a candidate compound relative to the levels of reporter gene product expressed in a cell that is not exposed to the test compound and/or to a cell that is exposed to a control compound. The change in level can be determined quantitatively for example, by measurement using a spectrophotometer, spectrofluorometer, luminometer, and the like, and will generally represent a statistically significant increase or decrease in the level from background. However, such a change may also be noted without quantitative measurement simply by, e.g., visualization, such as when the reporter gene is one that confers the ability on cells to form colored colonies on chromogenic substrates.

The term "sample" is used in its broadest sense. A sample suspected of containing nucleic acids encoding TCCV-1 or TCCV-2, or fragments thereof, or TCCV-1 or TCCV-2 polypeptide may comprise a bodily fluid; an extract from a cell chromosome, organelle, or membrane isolated from a cell; an intact cell; genomic DNA, RNA, or cDNA, in solution or bound to a substrate; a tissue; a tissue print; etc.

"Stringent conditions" refers to conditions which permit hybridization between polynucleotides and the claimed polynucleotides. Stringent conditions can be defined by salt concentration, the concentration of organic solvent, e.g., formamide, temperature, and other conditions well known in the art.

"Subject" means mammals and non-mammals. Mammals means any member of the Mammalia class including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

The term "substantially purified," when referring to a polypeptide, indicates that the polypeptide is present in the substantial absence of other similar biological macromolecules.

The term "transfection" refers to the insertion of an exogenous polynucleotide into a host cell, irrespective of the method used for the insertion, or the molecular form of the polynucleotide that is inserted. The insertion of a polynucleotide per se and the insertion of a plasmid or vector comprised of the exogenous polynucleotide are included. The exogenous polynucleotide may be directly transcribed and translated by the cell, maintained as a nonintegrated vector, for example, a plasmid, or alternatively, may be stably integrated into the host genome.

The term "transformed" refers to any known method for the insertion of foreign DNA or RNA sequences into a host prokaryotic cell. The term "transfected" refers to any known method for the insertion of foreign DNA or RNA sequences into a host eukaryotic cell. Such transformed or transfected cells include stably transformed or transfected cells in which the inserted DNA is rendered capable of replication in the host cell. They also include transiently expressing cells which express the inserted DNA or RNA for limited periods of time. The transformation or transfection procedure depends on the host cell being transformed. It can include packaging the polynucleotide in a virus as well as direct uptake of the polynucleotide, such as, for example, lipofection or microinjection. Transformation and transfection can result in incorporation of the inserted DNA into the genome of the host cell or the maintenance of the inserted DNA within the host cell in plasmid form. Methods of transformation are well known in the art and include, but are not limited to, viral infection, electroporation, lipofection, and calcium phosphate mediated direct uptake. "Treating" or "treatment" of a disease state includes: 1) preventing the disease state, i.e. causing the clinical symptoms of the disease state not to develop in a subject that may be exposed to or predisposed to the disease state, but does not yet experience or display symptoms of the disease state; 2) inhibiting the disease state, i.e., arresting the development of the disease state or its clinical symptoms; 3) or relieving the disease state, i.e., causing temporary or permanent regression of the disease state or its clinical symptoms.

A "variant" of TCCV-1 or TCCV-2 polypeptides refers to an amino acid sequence that is altered by one or more amino acid residues. The variant may have "conservative" changes, wherein a substituted amino acid has similar structural or chemical properties (e.g., replacement of leucine with isoleucine.) More rarely, a variant may have "nonconservative" changes (e.g., replacement of glycine with tryptophan.) Analogous minor variations may also include amino acid deletion or insertions, or both. Guidance in determining which amino acid variations may be substituted, inserted, or deleted without abolishing biological function may be found using programs well known in the art, for example, LASER-GENE software (DNASTAR).

The term "variant" when used in the context of a polynucleotide sequence, may encompass a polynucleotide sequence related to TCCV-1 or TCCV-2. This definition may include, for example "allelic" (as defined above), "splice," "species," "polymorphic," or "degenerate" variants. A splice variant may have significant identity to a reference molecule, but will generally have a greater of less number polynucleotides due to alternate splicing of exons during mRNA processing. The corresponding polypeptide may possess additional functional domains or an absence of domains. Species variants are polynucleotide sequences that vary from one species to another. The resulting polypeptides generally will have significant amino acid identity to each other. A polymorphic variant is a variation in the polynucleotide sequence of a particular gene between individuals within a given species. Polymorphic variants may also encompass "single nucleotide polymorphisms" (SNPs) in which the polynucleotide sequence varies by one base. The presence of SNPs may be indicative of, for example, a certain population, a disease state, or a propensity for a disease state. A degenerate variant encompasses a multitude of polynucleotides which encode TCCV-1 or TCCV-2 polypeptides. The degenerate variants may occur naturally or may be produced synthetically. Synthetic degenerate variants are made in accordance with the standard triplet genetic code as applied to the polynucleotide sequence of naturally occurring TCCV-1 or TCCV-2, and all such variations are to be considered as being specifically disclosed.

A "vector" is a replicon in which another polynucleotide segment is attached, such as to bring about the replication and/or expression of the attached segment. The term includes expression vectors, cloning vectors, and the like.

The Invention

The present invention is based on the discovery of a human T-type calcium channel $\alpha_{1f}$ subunit variant (TCCV-1 or TCCV-2), the polynucleotides encoding TCCV-1 or TCCV-2, and the use of these compositions for screening compounds useful in the treatment or prevention of pain, including, but not limited to peripheral pain; peripheral neuropathies; pain caused by trauma or toxic compounds; diabetic neuropathy; cancer pain, and the like.

The molecules of the present invention were isolated by homology searching of the GenBank database using the rat T-type calcium channel Otl G subunit (see, e.g., Perez-Reyes et al. (1 998) *Nature* 391:896–900; and GenBank Accession No. AF027984) and the human α1H subunit. (See, e.g., Cribbs et al. (1998) Circ. Res. 83:103–109; and GenBank Accession No. AF051946.) Two genomic clones (GenBank Accession No. AL02231 9 and AL00871 6) from human chromosome 22 were identified as being homologous to the two subunits.

Through PCR extension and use of sequence analysis software, TCCV-1 and TCCV-2 were assembled. TCCV-1 is a 6816 bp polynucleotide (SEQ ID NO:l) encoding a polypeptide of 2175 amino acid residues (SEQ ID NO:2). TCCV-2 is a 6855 bp polynucleotide (SEQ ID NO:3) encoding a polypeptide of 2188 amino acid residues (SEQ ID NO:4). FIGS. 1A–1F show an amino acid alignment between TCCV-1. TCCV-2, and the rat $\alpha 1_f$ subunit (GenBank Accession No. AAD17796; SEQ ID NO:5). The overall sequence identity between TCCV-1 and AAD17796 is approximately 77%, with 93% identity from residues 1 through 1823 of SEQ ID NO:2. A unique fragment of SEQ ID NO:2 from about residuel 1811 through about residue 2175 is useful, e.g., as an immungenic polypeptide. The corresponding polynucleotide sequence from about nucleotide 5622 through about nucleotide 6716 of SEQ ID NO:1 is useful, e.g., as a hybridization probe. A unique fragment of SEQ ID NO:4 from about residue 1824 through about residue 2188 is useful, e.g., as an immunogenic polypeptide. The corresponding polynucleotide fragment from about nucleotide 5661 through about nucleotide 6755 is useful, e.g., as a hybridization probe.

PCR analysis was performed using forward primers spanning exons 31 and 32 of SEQ ID NO:1, 3, and 12 (Primer Number 6352 for SEQ ID NO:1 and 12, and Primer Number 6344/88 for SEQ ID NO:3) and exons 32 and 33 of SEQ ID NO:1, 3, and 12 (Primer Number 6495 for SEQ ID NO:1 and 3, and Primer Number 6495/37 for SEQ ID NO:12) in combination with a reverse primer (Primer Number 6831 for SEQ ID NO: 1, 3, and 12). The results are illustrated in FIG. 3. No PCR product was detected using forward Primer Number 6493/37 and reverse Primer Number 6831 (lane 6).

The invention also encompasses nucleic or amino acid variants of TCCV-1 or TCCV-2. A preferred variant is one which has at least about 80%, more preferably at least about 90%, and most preferably at least about 95% amino acid or nucleic acid identity to the corresponding TCCV-1 or TCCV-2 sequence, and which contains at least one functional or structural characteristic of TCCV-1 or TCCV-2.

Polynucleotides

Although nucleotide sequences which encode TCCV-1 or TCCV-2 and its variants are preferably capable of hybridizing to the nucleotide sequence of the naturally occurring TCCV-1 or TCCV-2 under appropriately selected conditions of stringency, it may be advantageous to produce nucleotide sequence encoding TCCV-1 or TCCV-2 or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding TCCV-1 or TCCV-2 and its derivatives without altering the encoded amino acid include the production of RNA transcripts having more desirable properties, such as greater half-lifer or stability for improved translation, than transcripts produced from the naturally occurring sequence.

Also encompassed by the invention are polynucleotides that are capable of hybridizing to the claimed polynucleotide sequences, and, in particular, to those shown in SEQ ID NOs:1 and 3, under various conditions of stringency. (See, e.g., Wahl, G. M. and S. L. Berger (1987) Methods Enzymol. 152:399–401; Kimmel, A. R. (1987) Methods Enzymol. 152:507–511.) For example, stringent salt concentration will ordinarily be less that about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., preferably at least about 37° C., and more preferably 42° C. Varying additional parameters such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a more preferred embodiment, hybridization will occur at 42° C. in 250 mM NaCl, 25 mM trisodium citrate, 1% SDS, 50% formamide, and 200 µg/ml denatured ssDNA. Useful variations of these conditions will be readily apparent to those skilled in the art.

The washing steps which follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash step will ordinarily include temperature of at least about 25° C., more preferably of at least about 42° C., and most preferably of at least about 68° C. In a preferred embodiment, wash step will occur at 25° C. in 30 mM NaCl, 3 mM trisodium citrate, and 0.1% SDS. In a more preferred embodiment, wash step will occur at 42° C. in 15 mM NaCl, 1.5 mM trisodium citrate, and 0.1% SDS. In a most preferred embodiment, the wash step will occur at 68° C., in 15 mM NaCl, 1.5 mM trisodium citrate, and 0.1% SDS. Additional variations on these conditions will be readily apparent to those skilled in the art.

In another embodiment, polynucleotide sequences encoding all or part of TCCV-1 or TCCV-2 may be synthesized using chemical methods well known in the art. (See, e.g., Caruthers, M. H. et al. (1980) Nucl. Acids Res. Symp. Ser. 7:215–223, Hom, T. et al. (1980) Nucl. Acids Res. Symp. Ser. 7:225–232.)

The present invention further covers recombinant polynucleotides and fragments having a DNA sequence identical to or highly homologous to the isolated polynucleotides of TCCV-1 or TCCV-2. In particular, the sequences will often be operably linked to DNA segments which control transcription, translation, and DNA replication. Alternatively, recombinant clones derived from the genomic sequences, e.g., containing introns, will be useful for transgenic and knock-out studies, including transgenic cells, organisms, and knock-out animals, and for gene therapy. (See, e.g., Goodnow (1992) "Transgenic Animals" in Roitt (ed.) Encyclopedia of Immunology, Academic Press, San Diego, Calif., pp.1502–1504; Travis (1992) Science 254:707–710; Capecchi (1989) Science 244:1288–1292; Robertson (ed.) (1987) Teratocarcinomas and Embryonic Stem Cells: A Practical Approach, IRL Press, Oxford; Rosenberg (1992) J. Clinical Oncology 10:180–199; Hogan, et al. (eds.) (1994) Manipulating the Mouse Embryo: A Laboratory Manual, $2^{nd}$ edition, Cold Spring Harbor Press, N.Y.; Wei (1997) Ann. Rev. Pharmacol. Toxicol. 37:119–141; and Rajewsky, et al. (1996) J. Clin. Inves. 98:S51–S53.)

Examples of these techniques include: 1) Insertion of normal or mutant versions of DNA encoding TCCV-1 or TCCV-2 or homologous animal versions of these genes, by microinjection, retroviral infection, or other means well known to those skilled in the art, into appropriate fertilized embryos in order to produce a transgenic animal (see, e.g., Hogan, supra); and 2) homologous recombination (see, e.g., Capecchi, supra; and Zimmer and Gruss (1989) Nature 338:150–153) of mutant or normal, human or animal versions of these genes with the native gene locus in transgenic animals to alter the regulation of expression or the structure of TCCV-1 or TCCV-2.

The technique of homologous recombination is well known in the art. It replaces the native gene with the inserted gene and is thus useful for producing an animal that cannot express native receptor but does express, for example, an inserted mutant receptor, which has replaced the native receptor in the animal's genome by recombination, resulting in underexpression of the receptor.

Microinjection adds genes to the genome, but does not remove them, and so is useful for producing an animal which expresses its own and added receptors, resulting in overexpression of the receptor. One means available for producing a transgenic animal, with a mouse as an example, is as follows: Female mice are mated, and the resulting fertilized eggs are dissected out of their oviducts. The eggs are stored in an appropriate medium such as M2 medium (see, e.g., Hogan, supra). DNA or cDNA encoding TCCV-1 or TCCV-2 is purified from an appropriate vector by methods well known in the art. Inducible promoters may be fused with the coding region of the DNA to provide an experimental means to regulate expression of the trans-gene. Altematively, or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

Since the normal action of receptor-specific drugs is to activate or to inhibit the receptor, the transgenic animal model systems described above are useful for testing the biological activity of drugs directed against TCCV-1 or TCCV-2 even before such drugs become available. These animal model systems are useful for predicting or evaluating possible therapeutic applications of drugs which activate or inhibit TCCV-1 or TCCV-2 by inducing or inhibiting expression of the native or trans-gene and thus increasing or decreasing expression of normal or mutant TCCV-1 or TCCV-2 in the living animal. Thus, a model system is produced in which the biological activity of drugs directed against TCCV-1 or TCCV-2 are evaluated before such drugs become available.

The transgenic animals which over- or underproduce TCCV-1 or TCCV-2 indicate, by their physiological state, whether over- or underproduction of TCCV-1 or TCCV-2 is therapeutically useful. It is therefore useful to evaluate drug action based on the transgenic model system. One use is based on the fact that it is well known in the art that a drug such as an antidepressant acts by blocking neurotransmitter uptake, and thereby increases the amount of neurotransmitter in the synaptic cleft. The physiological result of this action is to stimulate the production of less receptor by the affected cells, leading eventually to underexpression. Therefore, an animal which underexpresses receptor is useful as a test system to investigate whether the actions of such drugs which result in under expression are in fact therapeutic. Another use is that if overexpression is found to lead to abnormalities, then a drug which down-regulates or acts as an antagonist to TCCV-1 or TCCV-2 is indicated as worth developing, and if a promising therapeutic application is uncovered by these animal model systems, activation or inhibition of TCCV-1 or TCCV-2 is achieved therapeutically either by producing agonist or antagonist drugs directed against TCCV-1 or TCCV-2 or by any method which increases or decreases the expression of TCCV-1 or TCCV-2 in man.

Polypeptides

The predicted sequence of TCCV-1 and TCCV-2 amino acid sequence is shown in SEQ ID NO:2 and SEQ ID NO:4, respectively. The peptide sequences allow preparation of peptides to generate antibodies to recognize such segments, and various different methods may be used to prepare such peptides. As used herein TCCV-1 or TCCV-2 shall encompass, when used in a protein context, a protein having an amino acid sequence shown in Table 2, or a significant fragment of such a protein. It also refers to a vertebrate, e.g., mammal, including human, derived polypeptide which exhibits similar biological function, e.g., antigenic, or interacts with TCCV-1 or TCCV-2 specific binding components, e.g., specific antibodies.

The term polypeptide, as used herein, includes a significant fragment or segment, and encompasses a stretch of amino acid residues of at least about 8 amino acids, generally at least 10 amino acids, more generally at least 12 amino acids, often at least 14 amino acids, more often at least 16 amino acids, typically at least 18 amino acids, more typically at least 20 amino acids, usually at least 22 amino acids, more usually at least 24 amino acids, preferably at least 26 amino acids, more preferably at least 28 amino acids, and, in particularly preferred embodiments, at least about 30 or more amino acids. The segments may have lengths of at least 37, 45, 53, 61, 70, 80, 90, etc., and often will encompass a plurality of such matching sequences. The specific ends of such a segment will be at any combinations within the protein. Preferably the fragment will encompass structural domains, e.g., [Give specific fragments], or unique regions useful in generation of binding compositions with specificity for TCCV-1 or TCCV-2.

In another embodiment of the invention, natural, modified, or recombinant nucleic acid sequences encoding TCCV-1 or TCCV-2 may be ligated to a heterologous sequence to encode a fusion protein. For example, to screen peptide libraries for inhibitors of TCCV-1 or TCCV-2 activity, it may be useful to encode a chimeric TCCV-1 or TCCV-2 protein that can be recognized by a commercially available antibody. A fusion protein may also be engineered to contain a cleavage site located between the TCCV-1 or TCCV-2 encoding sequence and the heterologous protein sequence, so that TCCV-1 or TCCV-2 may be cleaved and purified away from the heterologous moiety.

The protein may be produced using chemical methods to synthesize the amino acid sequence of TCCV-1 or TCCV-2, or a fragment thereof. For example, peptide synthesis can be performed using various solid-phase techniques. (See, e.g., Roberge, J. Y. et al. (1995) Science 269:202–204.) Automated synthesis may be achieved, for example, using the ABI 431 A peptide synthesizer (Perkin Elmer).

The newly synthesized peptide may be substantially purified by preparative high performance liquid chromatography. (See, e.g., Creighton, T. (1983) Proteins, Structures and Molecular Principles, WH Freeman and Co., New York, N.Y.) The composition of the synthetic peptides may be confirmed by amino acid analysis or sequencing (e.g., the Edman degradation procedure; Creighton, supra.) Additionally, the amino acid sequence of TCCV-1 or TCCV-2, or any part thereof, may be altered during direct synthesis and/or combined using chemical methods with sequences from other proteins, or any part thereof, to produce a variant polypeptide.

In order to express a biologically active TCCV-1 or TCCV-2, the nucleotide sequences encoding TCCV-1 or TCCV-2 or functional equivalents, may be inserted into appropriate expression vector, i.e., a vector which contains the necessary elements for the transcription and translation of the inserted coding sequence. Methods which are well known to those skilled in the art may be used to construct expression vectors containing sequences encoding TCCV-1 or TCCV-2 and appropriate transcriptional and translational control elements. These methods include in vitro recombinant DNA techniques, synthetic techniques, and in vivo genetic recombination. (See, e.g., Sambrook, J. et al. (1989) Molecular Cloning, A Laboratory Manual, Cold Spring Harbor Press, Plainview, N.Y.; and Ausubel, F. M. et al. (1989) Current Protocols in Molecular Biology, John Wiley & Sons, New York, N.Y.)

A variety of expression vector/host systems may be utilized to contain and express sequences encoding TCCV-1 or TCCV-2. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus) or with bacterial expression vectors (e.g., Ti or pBR322 plasmids); or animal cell systems. The invention is not limited by the host cell employed.

The "control elements" or "regulatory sequences" are those non-translated regions of the vector, e.g., enhancers, promoters, 5' and 3' untranslated regions, which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding TCCV-1 or TCCV-2, vectors based on SV40 or EBV may be used with an appropriate selectable marker.

In bacterial systems, a number of expression vectors may be selected depending upon the use intended for TCCV-1 or TCCV-2. For example, when large quantities of TCCV-1 or TCCV-2 are needed for the induction of antibodies, vectors which direct high level expression of fusion proteins that are readily purified may be used. Such vectors include, but are not limited to, the multifunctional *E. coli* cloning and expression vectors such as the BLUESCRIPT phagemid (Stratagene), in which the sequence encoding TCCV-1 or TCCV-2 may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. PGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. (See, e.g., Ausubel et al., supra; and Grant et al. (1987) Methods Enzymol. 153:516–544.)

An insect system may also be used to express TCCV-1 or TCCV-2. For example, in one such system, *Autographa califorica* nuclear polyhedrosis virus (AcNPV) is used as a vector to express foreign genes in *Spodoptera frugiperda* cells or in *Trichoplusia* larvae. The sequences encoding TCCV-1 or TCCV-2 may be cloned into a non-essential region of the virus, such as the polyhedrin gene, and placed under control of the polyhedrin promoter. Successful insertion of TCCV-1 or TCCV-2 will render the polyhedrin gene inactive and produce recombinant virus lacking coat protein. the recombinant viruses may then be used to infect, for example, *S. frugiperda* cells or *Trichoplusia larvae* in which TCCV-1 or TCCV-2 may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding TCCV-1 or TCCV-2 may be ligated into an adenovirus transcription/translation complex consisting of the late promoter and tripartite leader sequence. Insertion in a non-essential E1 or E3 region of the viral genome may be used to obtain a viable virus which is capable of expressing TCCV-1 or TCCV-2 in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding TCCV-1 or TCCV-2. Such signals include the ATG initiation codon and adjacent sequences. In cases where sequences encoding TCCV-1 or TCCV-2, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines, which stably express TCCV-1 or TCCV-2, may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk⁻ or aprt⁻ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, .beta. glucuronidase and its substrate GUS, and luciferase and its substrate luciferin, being widely used not only to identify transformants, but also to quantify the amount of transient or stable protein expression attributable to a specific vector system (Rhodes, Calif. et al. (1995) Methods Mol. Biol. 55:121–131).

Antibodies

Antibodies to TCCV-1 or TCCV-2 may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with TCCV-1 or TCCV-2 or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and Corynebacterium parvum are especially preferable.

It is preferred that the oligopeptides, peptides, or fragments used to induce antibodies to TCCV-1 or TCCV-2 have an amino acid sequence consisting of at least five amino acids and more preferably at least 10 amino acids, and most preferably at least 15 amino acids. It is also preferable that they are identical to a portion of the amino acid sequence of the natural protein, and they may contain the entire amino acid sequence of a small, naturally occurring molecule. Short stretches of TCCV-1 or TCCV-2 amino acids may be fused with those of another protein such as keyhole limpet hemocyanin and antibody produced against the chimeric molecule.

Monoclonal antibodies to TCCV-1 or TCCV-2 may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce TCCV-1 or TCCV-2-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for TCCV-1 or TCCV-2 may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between TCCV-1 or TCCV-2 and its specific antibody. A two-site, monoclonal-based immunoassay utilizing monoclonal antibodies reactive to two non-interfering TCCV-1 or TCCV-2 epitopes is preferred, but a competitive binding assay may also be employed (Maddox, supra).

Uses

The present invention provides various methods for determining whether a compound can modulate the activity of TCCV-1 or TCCV-2. The compound can be a substantially pure compound of synthetic origin combined in an aqueous medium, or the compound can be a naturally occurring material such that the assay medium is an extract of biological origin, such as, for example, a plant, animal, or microbial cell extract. The methods essentially entail contacting TCCV-1 or TCCV-2 or fragments thereof, with the compound under suitable conditions and subsequently determining if the compound modulates the activity of TCCV-1 or TCCV-2. The compounds of interest can function as agonists or antagonists of TCCV-1 or TCCV-2 activity. TCCV-1 or TCCV-2 or fragments thereof, can be expressed on a cell or tissue, naturally or recombinantly, or immobilized by attachment to a solid substrate, e.g., nitrocellulose or nylon membrane, glass, beads, etc. An example of a compound that may block a T-type calcium channel is ethosuximide and analogs thereof.

Transcription based assays that identify signals that modulate the activity of cell surface proteins, e.g., receptors, ion channels, etc., may be used to screen candidate compounds for their ability to stimulate reporter gene product expression and their potential to stimulate the expression of TCCV-1 or TCCV-2.

One method for identifying compounds that stimulate TCCV-1 or TCCV-2 promoter-controlled reporter gene expression comprises introducing into a cell a DNA construct that comprises TCCV-1 or TCCV-2 promoter operably linked to a reporter gene, mixing a test compound with the cell and measuring the level of expression of reporter gene product. A change in the level of expression of the reporter gene produced indicates that the compound is capable of modulating the level of TCCV-1 or TCCV-2 expression. The reporter gene construct is preferably stably integrated into the chromosomal DNA of the cell, but is also functional for the purposes disclosed herein in the form of an extrachromosomal element. The cell may be a eukaryotic cell, or any cell that contains the elements needed to express a structural gene under the regulatory influence of a mammalian gene promoter.

Other transcription-based assays are well known in the art. (See, e.g., Zlokarnik, et al. (1998) Science 279:84–88; Siverman, supra; and Gonzalez and Negulescu, (1998) Curr. Opin. Biotechnol. 9:624–631.) These transcription based assays asses the intracellular transduction of an extracellular signal using recombinant cells that are modified by introduction of a reporter gene under the control of a regulatable promoter.

A two-hybrid system-based approach can also be employed for compound screening, small molecule identification, and drug discovery. The underlying premise of the two-hybrid system, originally described in yeast by Fields and Song (1989) Nature 340:245–246, provides a connection between a productive protein-protein or protein-compound interaction pair of interest and a measurable phenotypic change in yeast. A reporter cassette containing an up-stream activation sequence which is recognized by a DNA binding domain, is operationally linked to a reporter gene, which when expressed under the correct conditions will generate a phenotypic change. The original two-hybrid system has recently been modified for applicability in high-throughput compound screening. (See, e.g., Ho et al. (1996) Nature 382:822–826; Licitra and Liu (1996) Proc. Natl. Acad. Sci. USA 93:12817–12821; and Young et al. (1998) Nature Biotech. 16:946–950.)

Assays for identifying compounds that modulate ion channel activity are practiced by measuring the ion channel activity when a cell expressing the ion channel of interest, or fragments thereof, is exposed to a solution containing the test compound and a ion channel selective ion and comparing the measured ion channel activity to the native ion channel activity of the same cell or a substantially identical control cell in a solution not containing the test compound. Methods for practicing such assays are known to those of skill in the art. (See, e.g., Mishina et al. (1985) Nature 313:364–369; and Noda, et al. Nature 322:836–828.)

Ion channel activity can be measured by methods such as electrophysiology (two electrode voltage clamp or single electrode whole cell patch clamp), guanidinium ion flux assays, toxin-binding assays, and Fluorometric Imaging Plate Reader (FLIPR) assays. (See, e.g., Sullivan, et al. (1999) Methods Mol. Biol. 114:125–133; Siegel and Isacoff (1997) Neuron 19:1–20; and Lopatin, et al. (1998) Trends Pharmacol. Sci. 19:395–398.) An "inhibitor" is defined generally as a compound, at a given concentration, that results in greater than 50% decrease in ion channel activity, preferably greater than 70% decrease in ion channel activity, more preferably greater than 90% decrease in ion channel activity.

The binding or interaction of the compound with a receptor or fragments thereof, can be measured directly by using radioactively labeled compound of interest (see, e.g., Wainscott et al. (1993) Mol. Pharmacol. 43:419–426; and Loric, et al. (1992) FEBS Left. 312:203–207) or by the second messenger effect resulting from the interaction or binding of the candidate compound. (See, e.g., Lazereno and Birdsall (1993) Br. J. Pharmacol.109:1120–1127.) Modulation in receptor signaling can be measured using a detectable assay, e.g., the FLIPR assay. (See, e.g., Coward, P. (1999) Anal. Biochem. 270:242–248; Sittampalam, supra; and Gonzalez and Negulescu, supra.) Activation of certain receptors, in particular, GPCRs, can be measured an $^{35}$S-GTPγS binding assay. (See, e.g., Lazareno (1999) Methods Mol. Biol. 106:231–245.)

Alternatively, the candidate compounds can be subjected to competition screening assays, in which a known ligand, preferably labeled with an analytically detectable reagent, most preferably radioactivity, is introduced with the drug to be tested and the capacity of the compound to inhibit or enhance the binding of the labeled ligand is measured. Compounds are screened for their increased affinity and selectivity for the specific receptor or fragments thereof.

Candidate compounds are useful in the treatment or prophylaxis of pain, including, but not limited to, peripheral pain; peripheral neuropathies; pain caused by trauma or toxic compounds; diabetic neuropathy; cancer pain, and the like.

The polynucleotides of the present invention can be used to design antisense oligonucleotides that inhibit translation of mRNA encoding the TCCV-1 or TCCV-2 of the present invention. Synthetic oligonucleotides, or other antisense chemical structures are designed to bind to mRNA encoding TCCV-1 or TCCV-2 and inhibit translation of mRNA and are useful to inhibit expression of TCCV-1 or TCCV-2. This invention provides a means to alter levels of expression of TCCV-1 or TCCV-2 by the use of a synthetic antisense oligonucleotide (SAO) which inhibits translation of mRNA encoding these receptors.

The SAO is designed to be capable of passing through cell membranes in order to enter the cytoplasm of the cell by virtue of physical and chemical properties of the SAO which render it capable of passing through cell membranes (e.g. by designing small, hydrophobic SAO chemical structures) or by virtue of specific transport systems in the cell which recognize and transport the SAO into the cell. In addition, the SAO can be designed for administration only to certain selected cell populations by targeting the SAO to be recognized by specific cellular uptake mechanisms which binds and takes up the SAO only within certain selected cell populations. For example, the SAO may be designed to bind to TCCV-1 or TCCV-2 which are found only in certain cell types.

The SAO is also designed to recognize and selectively bind to the target mRNA sequence, which may correspond to a sequence contained within the sequences of SEQ ID NO:1 or 3 by virtue of complementary base pairing to the mRNA. Finally, the SAO is designed to inactivate the target mRNA sequence by any of three mechanisms: 1) binding to the target mRNA and thus inducing degradation of the mRNA by intrinsic cellular mechanisms such as RNAse H digestion; 2) inhibiting translation of the mRNA target by interfering with the binding of translation-regulating factors or of ribosomes; or 3) inclusion of other chemical structures, such as ribozyme sequences or reactive chemical groups, which either degrade or chemically modify the target mRNA.

Synthetic antisense oligonucleotide drugs have been shown to be capable of the properties described above when directed against mRNA targets. (See, e.g., Cohen (1989) Trends in Pharm. Sci. 10:435; and Weintraub (1990) Sci. Am. 262:40–46.) In addition, coupling of ribozymes to antisense oligonucleotides is a promising strategy for inactivating target mRNA. (See, e.g., Sarver et al. (1990) Science 247:1222.)

Diagnostics and kits

The present invention contemplates use TCCV-1 or TCCV-2 polynucleotides, polypeptides, and antibodies in a variety of diagnostic methods kits. Typically the kit will have a compartment containing either a defined TCCV-1 or TCCV-2 polypeptide, polynucleotide, or a reagent which recognizes one or the other, e.g., antigen fragments or antibodies. Additionally the kit will include the reagents needed to carry out the assay in a separate compartment as well as instructions for use and proper disposal.

A variety of protocols including ELISA, RIA, and FACS for measuring TCCV-1 or TCCV-2 are known in the art and provide a basis for diagnosing altered or abnormal levels of TCCV-1 or TCCV-2 expression. Normal or standard values for TCCV-1 or TCCV-2 expression are established by combining body fluids or cell extracts taken from normal mammalian subjects, preferably human, with antibody to TCCV-1 or TCCV-2 under conditions suitable for complex formation. The amount of standard complex formation may be quantified by various methods, but preferably by photometric, means. Quantities of TCCV-1 or TCCV-2 expressed in control and disease samples from biopsied tissues are compared with the standard values. Deviation between standard and subject values establishes the parameters for diagnosing disease.

In another embodiment of the invention, the polynucleotides encoding TCCV-1 or TCCV-2 may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of TCCV-1 or TCCV-2 may be correlated with disease. The diagnostic assay may be used to distinguish between absence, presence, and excess expression of TCCV-1 or TCCV-2, and to monitor regulation of TCCV-1 or TCCV-2 levels during therapeutic intervention.

In one aspect, hybridization with PCR probes which are capable of detecting polynucleotide sequences, including genomic sequences, encoding TCCV-1 or TCCV-2 or closely related molecules, may be used to identify nucleic acid sequences which encode TCCV-1 or TCCV-2. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding TCCV-1 or TCCV-2, alleles, or related sequences.

Probes may also be used for the detection of related sequences, and should preferably contain at least 50% of the nucleotides from any of the TCCV-1 or TCCV-2 encoding sequences. The hybridization probes of the subject invention may be DNA or RNA and derived from the nucleotide sequence of SEQ ID NOs:1 or 3 or from genomic sequence including promoter, enhancer elements, and introns of the naturally occurring TCCV-1 or TCCV-2.

Means for producing specific hybridization probes for DNAs encoding TCCV-1 or TCCV-2 include the cloning of nucleic acid sequences encoding TCCV-1 or TCCV-2 or TCCV-1 or TCCV-2 derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as $^{32}$P or $^{35}$S, or enzymatic labels, such as alkaline phosphatase coupled to the probe via avidin/biotin coupling systems, and the like.

Polynucleotide sequences encoding TCCV-1 or TCCV-2 may be used for the diagnosis of diseases, conditions, or disorders which are associated with expression of TCCV-1 or TCCV-2 including, but not limited to, pain; peripheral pain; peripheral neuropathies; pain caused by trauma or toxic compounds; diabetic neuropathy; cancer pain, and the like.

In order to provide a basis for the diagnosis of disease associated with expression of TCCV-1 or TCCV-2, a normal or standard profile for expression is established. This may be accomplished by combining body fluids or cell extracts taken from normal subjects, either animal or human, with a polynucleotide sequence, or a fragment thereof, which encodes TCCV-1 or TCCV-2, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from subjects who are symptomatic for disease. Deviation between standard and subject values is used to establish the presence of disease.

Once a disease is established and a treatment protocol is initiated, hybridization assays may be repeated on a regular basis to evaluate whether the level of expression in the subject begins to approximate that which is observed in the normal subject. The results obtained from successive assays may be used to show the efficacy of treatment over a period ranging from several hours to several days to several months.

Additional diagnostic uses for oligonucleotides designed from the sequences encoding TCCV-1 or TCCV-2 may involve the use of PCR. Such oligomers may be chemically synthesized, generated enzymatically, or produced in vitro. Oligomers will preferably consist of two nucleotide sequences, one with sense orientation (5' to 3') and another with antisense (3' to 5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of TCCV-1 or TCCV-2 include radiolabeling or biotinylating nucleotides, coamplification of a control nucleic acid, and standard curves onto which the experimental results are interpolated. (See, e.g., Melby, P. C. et al. (1993) J. Immunol. Methods, 159:235–244; and Duplaa, C. et al. (1993) Anal. Biochem. 212:229–236.) The speed of quantitation of multiple samples may be accelerated by running the assay in an ELISA format where the oligomer of interest is presented in various dilutions and a spectrophotometric or colorimetric response gives rapid quantitation.

In another embodiment of the invention, the nucleic acid sequences which encode TCCV-1 or TCCV-2 can be used to generate hybridization probes which are useful for mapping the naturally occurring genomic sequence. Fragments of TCCV-1 and TCCV-2 have been used to map these genes to the appropriate mouse and human chromosomes. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions, or single chromosome cDNA libraries. (See, e.g., Price, C. M. (1993) Blood Rev. 7:127–134, and Trask, B. J. (1991) Trends Genet. 7:149–154.)

Fluorescent in situ hybridization (FISH) may be correlated with other physical chromosome mapping techniques and genetic map data. (See, e.g., Verma et al. (1988) Human Chromosomes: A Manual of Basic Techniques, Pergamon Press, New York, N.Y.) Examples of genetic map data can be found in various scientific journals or at Online Mendelian Inheritance in Man (OMIM). Correlation between the location of the gene encoding TCCV-1 or TCCV-2 on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region (see, e.g., Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

All patents, patent applications, and publications mentioned herein, whether supra or infra, are each incorporated by reference in its entirety. The broad scope of this invention is best understood with reference to the following examples, which are not intended to limit the invention to the specific embodiments described below.

EXAMPLES

Some of the standard methods are described or referenced, e.g., in Maniatis et al. (1982) Molecular Cloning, A Laboratory Manual, Cold Spring Harbor Laboratory, Cold Spring Harbor Press; Sambrook et al. (1989) Molecular Cloning: A Laboratory Manual, (2d ed.), vols. 1–3, CSH Press, N.Y.; or Ausubel et al. (1987 and Supplements) Current Protocols in Molecular Biology, Greene/Wiley, New York; Innis et al. (eds.)(1 990) PCR Protocols: A Guide to Methods and Applications Academic Press, N.Y. Methods for protein purification include such methods as ammonium sulfate precipitation, column chromatography, electrophoresis, centrifugation, crystallization, and others. See, e.g., Ausubel et al. (1987 and periodic supplements); Deutscher (1990) "Guide to Protein Purification" in Methods in Enzymology, vol. 182, and other volumes in this series; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See, e.g., Hochuli (1989) Chemische Industrie 12:69–70; Hochuli (1990) "Purification of Recombinant Proteins with Metal Chelate Absorbent" in Setlow (ed.) Genetic Engineering Principle and Methods 12:87–98, Plenum Press, N.Y.; and Crowe et al. (1992) OIAexpress: The High Level Expression & Protein Purification System QUIAGEN, Inc., Chatsworth, Calif.

Example I

Homology Search of GenBank

Searching of GenBank databases with the human T-type calcium channel subunit $\alpha 1_H$ sequence (GenBank Accession No. AF051946; and Cribbs et al. (1998) Circ. Res. 83:103–109) revealed two genomic clones from human chromosome 22 with extensive homology to $\alpha 1_H$. (GenBank Accesion Nos. AL022319 and AL008716.) BLAST results showed that these clones represented the same sequence, potentially a novel T-type Calcium channel as the $\alpha 1_G$ subunit was shown to be localized to human chromosome 17 and $\alpha 1_H$ to human chromosome 16. Additionally a further search of GenBank with the rat $\alpha 1_G$ sequence also revealed less extensive homology to the two clones above, as well as a human chromosome 17 genomic clone (GenBank Accession No. AC004590), which appeared to contain the entire human $\alpha 1_G$ sequence within 34 exons.

Comparison of the deduced exon structure of $\alpha 1_G$ with the alignments from the $\alpha 1_H$ BLAST against GenBank Accession Nos. AL022319 and AL008716 allowed the identification of many potential exons, from approximately the beginning of domain I to the end of domain IV. Due to insufficient homology with r$\alpha$1G or h$\alpha$1H, several exons could not initially be identified, in particular, exons corresponding to the interdomain regions. Similarly, the amino- and carboxyterminal exons could not be initially identified.

Example II

PCR Cloning and Assembly of TCCVs

PCR primers based on GenBank Accession No. AL022319 sequence were designed to clone the region from domain I to domain IV:

Sense 5' GGGCGCCATCAACTTTGACAACATC 3' (SEQ ID NO:6); and

Antisense 5' CTCACGAAGTACAGCGGCGACAC 3' (SEQ ID NO:7)

Optimized reaction conditions to produce the expected 4 kb product, per 50 μl reaction, were: each primer at 0.2μM, 1×ADVANTAGE-GC cDNA reaction buffer (Clontech, Palo Alto, Calif.), 0.2mM dNTPs, 1 μl ADVANTAGE-GC cDNA polymerase (Clontech), 1×GC MELT (Clontech), and 5 μl MARATHON-READY human brain cDNA (Clontech). Temperature and time parameters were 94°, 1 min; 95°, 10 sec, 68°, 6 min, 42 cycles; 68°, 10 min.

A band at 4 kb was excised from low-melt agarose gel, melted at 65° C. for 5 min, and subsequently ligated into the pCR2.1 TOPO vector (Invitrogen, Mountain View, Calif.) following kit instructions. The ligated vector was transformed into *E. coli* DH5α competent cells (Life Technologies, Bethesda, Md.) according to the manufacturers protocol. Two of the resulting clones, KC-1 and KC-4 were fully sequenced.

BLAST comparison of these sequences with the novel human genomic sequences AL022319 and AL008716 revealed the true exon structure for this region of the gene. This sequence was not identical to that predicted by homology with the other channels. Additionally, KC-1 had 4 mutations and KC-4 had 8 mutations relative to the genomic sequences. Of note, none of the apparent mutations in the KC-1 sequence occurred between the unique AvrII and HindIII sites. Compensation for these mutations revealed a continuous reading frame, whose deduced amino acid sequence was homologous to the $r\alpha 1_G$ and $h\alpha 1_H$ amino acid sequences corresponding to exons 6 to 31 of the $r\alpha 1_G$ sequence. Additional homology comparisons revealed that genomic clone AL008716 only contained exons 2 to 25 and genomic clone AL022319 contained, at least, exons 5 to 31.

The sequence for exons 2–7 (using the $r\alpha 1_G$ numbering of exons) was assembled electronically from the genomic sequences and used to BLAST the GenBank databases. A new chromosome 22 genomic clone was found (GenBank Accession No. AL022312), which contained exon 2 near to its 3' end. In cloning exon 1, a comparison of ral $r\alpha 1_G$ and $h\alpha 1_H$ exon 1 amino acid sequences was made, revealing a short region of amino acid homology at the 3' end. The sequence of the last 30 amino acids from $r\alpha 1_G$ exon 1 was used as query in a TFASTA search of the GenBank databases. This search found a match in the new chromosome 22 genomic clone, AL022312, approximately 27 kb in the 5' direction from exon 2. This potential exon 1 had a reading frame containing the matching homology, as well as additional homology, extending to a potential initiating methionine residue. The large potential intron between exons 1 and 2 had atypical splice sites, AT . . . AC, instead of the usual GT . . . AG. The first intron of r$\alpha 1_G$ also has a similar atypical splice site. Electronic splicing of exon 1 to the previously identified exons resulted in a sequence with a continuous open reading frame.

PCR primers, described below, were designed to amplify the region from about 190 bp 5' of the likely start codon to about 120 bp 3' of the unique AvrII site:

Sense 5' CTGGGCCCTCAGCTGTTTCGTAATC 3' (SEQ ID NO:8); and

Antisense 5' GCGCTGGTCATAGCTCATCCTCCCTA-GAGA 3' (SEQ ID NO:9)

Reaction conditions were the same as above, except 2.5 µl MARATHON-READY human brain cDNA (Clontech) was used as template in a 25 µl reaction, but in the absence of GC-MELT (Clontech). PCR reaction conditions were: 95° C., 1 min; 95° C., 10 sec, 68° C., 20 sec, 72° C., 4 min, 42 cycles; 72°C., 7 min. A portion of this reaction was run into a low-melt agarose gel and a band at 3 kb was excised and cloned as described above. Of four isolates sequenced, KZ-2 was found to have only one silent mutation between the 5' end and the AvrII site.

In order to identify the 3' most exons, 16 kb of genomic clone AL022319 sequence, beginning near exon 26, was run on the GENIE gene finder program, (Lawrence Berkeley National Laboratory) which predicted exons 29, 30, 31 as well as four new additional exons following exon 31. The last exon contained a stop codon in the reading frame and appeared to lack additional splice consensus sites. An additional analysis of 10 kb in the 3' direction predicted no additional exons.

PCR primers, as described below, were designed to overlap the KC-1 sequence (about 200 bp 5' of the HindIII site) and to include the coding region of the possible 3' most exon, including about 100 bp of 3' non-coding sequence:

Sense 5' GCGCTTCTTCAAGGACCGATGG 3' (SEQ ID NO:10); and Antisense 5' CCCAGGTGTGGAC-GAAGTATTGCT 3' (SEQ ID NO:11)

Reaction conditions for amplifying the highly GC-rich sequence were the same as above, except 2.5 µl MARATHON-READY human brain cDNA (Clontech) was used as template in a 25 µl reaction, including 1×GC-MELT (Clontech). PCR reaction conditions were: 95° C., 1 min; 95° C., 10 sec, 62° C., 20 sec, 72° C., 4 min, 42 cycles; 72° C., 5 min. A portion of this reaction was run into a low-melt agarose gel and a band at 2.1 kb was excised and cloned as above. Sequence analysis of several of these clones revealed the correct exon structure for this region, which was not entirely as predicted, and the presence of alternative 3' splice site usage in some clones, resulting in a 39 bp difference in exon 32. All clones had one or more base-substitution mutations. However, KS-6, containing the short form of exon 32, had only one silent mutation in the 5' half of the gene bounded by the unique HindIII and BamHI sites. KS-18, containing the longer form of exon 32, also had no mutations between HindIII and BamHI, whereas KS-13 was mutation free only from the BamHI site to the 3' end. Thus, two versions of the 3' end region of the gene from the HindIII site to the stop codon, differing only in the exon 32 splice variation, could be assembled from these three clones. All three clones were digested with HindIII and BamHI and the reaction products run on a low-melt agarose gel. The desired bands were excised from the gel, melted briefly at 65° C., ligated together and transformed into E. coli DH5α competent cells as above. The 0.9 kb fragments from KS-6 and KS-18 were separately ligated to the 5 kb fragment from KS-13 to give isolates LD-1 and LE-1 respectively.

To assemble full-length coding sequences for the two human $\alpha 1I$ splice variants, the 3 kb KZ-2 EcoRI-AvrII fragment, the 2 kb KC-1 AvrII-HindIII fragment, either the 2 kb LD-1 or LE-1 HindIII-NotI fragment, and the 5.5 kb pClneo (Promega) mammalian cell expression vector EcoRI-NotI fragment were prepared and ligated together as above. Of the products of these clonings, isolate LF-1 (TCCV-1) contains the full-length short exon 32 form and isolate LG-1 (TCCV-2) contains the full length long exon 32 form of the human $\alpha 1_I$ subunit.

Example III

Analysis of Splicing Patterns

Patterns of splicing at the 3' end of human and rat $\alpha 1_I$ subunit genes were investigated by PCR. Primers were designed to amplify the entire region as well as to amplify specific splice products. Primer locations were chosen, in part, to minimize differences in the rat and human sequences, so that a single primer set could be used to amplify from both templates. Primers 6066 and 6831 were designed to amplify the region from exon 31 to 35 containing the rat and human splice variations. (See FIGS. 2A–2C.)

Four forward primers (Primer Numbers 6352, 6344/88, 6495, and 6495/37) were designed from the human DNA sequences to examine specifically splicing at exon 32 and at exon 33 and to be used with reverse primer 6831. As shown in FIGS. 2A–2C, these primers were designed to span the splice sites, so that only one specific product could be amplified for each primer. The human intron sequence was considered in designing these primers to reduce the possibility of amplifying unspliced sequences.

Optimum PCR conditions were established, using plasmid templates containing the long and short forms of exon 32 and the rat and human forms of exon 33, for which the specific PCR product for each primer set was obtained only from the specific template: 94° C., 30 sec; 94° C., 10 sec, 62° C., 15 sec, 68° C., 1 min, 30 cycles; 68° C., 3 min. PCR reaction conditions were as follows: 1×ADVANTAGE cDNA PCR reaction buffer (Clontech), 0.2 mM dNTPs, 1×PCRX reagent (Life Technologies), 0.2 µM each primer, 0.2 µl 50×ADVANTAGE cDNA polymerase mix (Clontech) and 0.5 ng plasmid template in a 20 µl reaction.

To examine the presence of the various splice products in MARATHON-READY human brain cDNA (Clontech), 2.5 µl template was used in 25 µl reactions as above with 0.25 µl 50×ADVANTAGE cDNA polymerase mix (Clontech). Cycling conditions were identical, except that the annealing temperature was 63° C. for 36 or 42 cycles. Similar results were obtained at 36 or 42 cycles. The long form of exon 32 (TCCV-1) was somewhat more abundant (2 to 5 fold) than the short form (TCCV-2). In addition, only the "human" form of exon 33 was found. A PCR product corresponding to the rat $\alpha 1_I$ subunit was not detected in the human brain cDNA (See FIG. 3).

Example IV

Transfection of TSA201 Cells

TSA201 cells were plated into wells of BIOCOAT poly-D-lysine coated 6 well dishes (Becton-Dickinson, Mountain View, Calif.) at a density of $3\times10^5$ cells/well two days prior to transfection or $7.5\times10^5$ cells/well one day prior to transfection. The medium was either the usual culture medium but without antibiotics, or, in some cases, a special low-calcium medium.

The vectors containing TCCV-1 or TCCV-2 were transfected into TSA201 cells using the LIPOFECTAMINE 2000 (Life Technologies, Bethesda, Md.) transfection kit and accompanying protocols. For each well of transfected cells, 4 μg of TCCV-1 or TCCV-2 plasmid DNA and 0.8 μg of pHook-1 DNA were combined in a tube with 250 μl of OPTI-MEM serum free medium (Life Technologies). An equal volume of diluted LIPOFECTAMINE 2000 reagent was added to each tube of diluted DNA and the mixtures were mixed and allowed to incubate at room temperature in the dark for 20 minutes. During the incubation, the medium on the cells was changed to 2.5 ml/well of DMEM with 0.1 mM MEM non-essential amino acids (Life Technologies), without serum and without antibiotics. The DNA/LIPOFECTAMINE 2000/OPTI-MEM mixture was added dropwise to cell wells while swirling the microtiter plate. The plate was returned to 37° C., 5% $CO_2$ for 4 to 5 hours.

Cells were resuspended and plated immediately after stopping the transfection reaction. Medium was removed from the cell wells and replaced with 2 ml of Dulbecco's Phosphate Buffered Saline (Life Technologies) without calcium or magnesium. The dish was returned to the incubator for four minutes. Cell monolayers were rinsed from the surface of the wells by trituration with a 2 ml pipet, directing the stream at the surface of the well to dislodge the cells. The resuspended cells were plated at 1:20 dilution in either regular culture medium or low calcium medium in 35 mm dishes that had been pre-coated with poly-D-lysine.

Alternatively, following the 4–5 hour incubation described above, the medium was replaced with either regular culture medium or low calcium medium and the cells were incubated overnight at 37° C. The cells were subsequently resuspended and plated as described above.

Although the foregoing invention has been described in some detail by way of illustration and example for purposes of clarity and understanding, it will be obvious that certain changes and modifications may be practiced within the scope of the appended claims.

What is claimed is:

1. A polynucleotide encoding a polypeptide comprising the amino acid sequence of SEQ ID NO:2 or 4.

2. The polynucleotide of claim 1, wherein the polynucleotide is detectably labeled.

3. An isolated polynucleotide which is the complement of the polynucleotide of claim 1.

4. The isolated polynucleotide of claim 3, wherein the polynucleotide is detectably labeled.

5. The polynucleotide of claim 1, wherein the polynucleotide comprises the nucleic acid sequence of SEQ ID NOs:1 or 3.

6. An expression vector comprising the polynucleotide of claim 1.

7. A host cell comprising the expression vector of claim 6.

8. The host cell of claim 7, wherein the host cell is a prokaryotic cell.

9. The host cell of claim 7, wherein the host cell is a eukaryotic cell.

10. A method of producing an TCCV-1 or TCCV-2 polypeptide, the method comprising:

a) culturing the host cell of claim 7 under conditions suitable for expression of the polypeptide; and b) recovering the polypeptide from the host cell.

11. A method of detecting a polynucleotide encoding an TCCV-1 or TCCV-2 polypeptide in a sample containing nucleic acid material, the method comprising:

a) contacting the sample with the polynucleotide of claim 3 under conditions suitable for formation of a hybridization complex; and b) detecting the complex, wherein the presence of the complex is indicative of the presence of the polynucleotide encoding the polypeptide in the sample.

12. A test kit comprising a polynucleotide of claim 5.

* * * * *